United States Patent [19]

Donson et al.

[11] Patent Number: 5,316,931

[45] Date of Patent: May 31, 1994

[54] PLANT VIRAL VECTORS HAVING HETEROLOGOUS SUBGENOMIC PROMOTERS FOR SYSTEMIC EXPRESSION OF FOREIGN GENES

[75] Inventors: Jon Donson, Davis, Calif.; William O. Dawson, Winter Haven, Fla.; George L. Granthan, Riverside, Calif.; Thomas H. Turpen, Vacaville, Calif.; Ann M. Turpen, Vacaville, Calif.; Stephen J. Garger, Vacaville, Calif.; Laurence K. Grill, Vacaville, Calif.

[73] Assignee: Biosource Genetics Corp., Vacaville, Calif.

[21] Appl. No.: 923,692

[22] Filed: Jul. 31, 1992

Related U.S. Application Data

[63] Continuation-in-part of Ser. No. 600,244, Oct. 22, 1990, abandoned, Ser. No. 641,617, Jan. 16, 1991, abandoned, Ser. No. 737,899, Jul. 26, 1991, abandoned, and Ser. No. 739,143, Aug. 1, 1991, abandoned, said Ser. No. 600,244, is a continuation of Ser. No. 310,881, Feb. 17, 1989, abandoned, which is a continuation-in-part of Ser. No. 160,766, Feb. 26, 1988, abandoned, and Ser. No. 160,771, Feb. 26, 1988, abandoned, said Ser. No. 641,617, is a continuation of Ser. No. 347,637, May 5, 1989, abandoned, said Ser. No. 737,899, is a continuation of Ser. No. 363,138, Jun. 8, 1989, abandoned, which is a continuation-in-part of Ser. No. 219,279, Jul. 15, 1988, abandoned.

[51] Int. Cl.⁵ .................. C12N 15/83; A01H 5/00; C07H 21/04
[52] U.S. Cl. .................. 435/172.3; 435/69.1; 435/70.1; 435/320.1; 536/23.72; 536/24.1; 800/205; 935/25; 935/57; 935/64; 935/67
[58] Field of Search ............ 435/69.1, 70.1, 172.3, 435/320.1; 536/23.72, 24.1; 800/205; 935/25, 57, 64, 67

[56] References Cited

U.S. PATENT DOCUMENTS 4,855,237 8/1989 Morinaga et al. .............. 435/320
5,128,460 7/1992 Piatak, Jr. et al. .............. 536/27

FOREIGN PATENT DOCUMENTS 0278667 2/1987 European Pat. Off. ...... C12N 15/00

OTHER PUBLICATIONS

Lehto et al 1990 Virology 175:30–40.
Gallie et al 1987 Science 236:1122–1124.
Matthews 1991 In Plant Virology 3rd Ed. (Academic Press) pp. 143–195.
Goldbach 1990 In New Aspects of Positive-Stand RNA Viruses; Brinton et al (eds), Am Soc. Microbiol publisher; pp. 3–11.
Kumagai et al 1993 Proc Natl Acad Sci USA 90:427–430.
Alquist and Janda, "cDNA Cloning and In Vitro Transcription of the Complete Brome Mosaic Virus Genome", *Mol. and Cell. Biol.* 4: 2876–2882 (1984).
Dawson, et al., "cDNA cloning of the complete genome of tobacco mosaic virus and production of infectious transcripts", *Proc. Natl. Acad. Sci. USA* 83: 1832–1836 (1986).
Lebeurier, et al., "Infectivities of native and cloned DNA of cauliflower mosaic virus", *Gene* 12: 139–146 (1980).
Brisson and Hohn, "Plant virus Vectors: Cauliflower Mosaic Virus", *Methods in Enzymology* 118: 659–668 (1986).

(List continued on next page.)

Primary Examiner—Patricia R. Moody
Attorney, Agent, or Firm—Albert P. Halluin

[57] ABSTRACT

The present invention is directed to recombinant plant viral nucleic acids and to hosts infected thereby. The recombinant plant viral nucleic acids comprise a native plant viral subgenomic promoter, at least one non-native plant viral subgenomic promoter, a plant viral coat protein coding sequence, and optionally, at least one non-native nucleic acid sequence to be transcribed or expressed in the infected host plant. The recombinant plant viral nucleic acids are stable, capable of systemic infection and capable of stable transcription or expression in the plant host of the non-native nucleic acid sequences.

38 Claims, 8 Drawing Sheets

OTHER PUBLICATIONS

Dawson, et al., "A Tobacco Mosaic Virus-Hybrid Expresses and Loses an Added Gene", *Virology* 172: 285–292 (1989).

Takamatusu, et al., "Expression of bacterial chloramphenicol acetyltransferase gene in tobacco plants mediated by TMV-RNA", *The EMBO Journal* 6: 307–311 (1987).

French, et al., "Bacterial Gene Inserted in an Engineered RNA Virus: Efficient Expression in Monocotyledonous Plant Cells", *Science* 231: 1294–1297 (1986).

Takamatsu, et al., "Production of enkephalin in tobacco protoplasts using tobacco mosaic virus RNA vector", *FEBS Letters* 269: 73–76 (1990).

Ooshika, et al., "Identification of the 30K Protein of TMV by Immunoprecipitation with Antibodies Directed against a Synthetic Peptide", *Virology* 132: 71–78 (1984).

Deom, et al., "The 30-Kilodalton Gene Product of Tobacco Mosaic Virus Potentiates Virus Movement", *Sicence* 237: 389–394 (1987).

Nozu, et al., "Chemical and Immunological Characterization of Cucumber Green Mottle Mosaic Virus (Watermelon Strain) Protein", *Virology* 45: 577–585 (1971).

Kurisu, et al., "Biochemical Characterization of Cucumber Green Mottle Mosaic Virus Ribonucleic Acid", *Virology* 70: 214–216 (1976).

Fukuda, et al., "Correlation between particle multiplicity and location on virion RNA of the assembly initiation site for viruses of the tobacco mosaic virus group", *Proc. Natl. Acad. Sci. USA* 78: 4231–4235 (1981).

Otsuki, et al., "Reconstitution of tobacco mosaic virus rods occurs bidirectionally from an internal initiation region: Demonstration by electron microscopic serology", *Proc. Natl. Acad. Sci. USA* 74: 1913–1917 (1977).

Fukuda, et al., "The Site of Initiation of Rod Assembly on the RNA of a Tomato and a Cowpea Strain of Tobacco Mosaic Virus", *Virology* 101: 492–502 (1980).

Meshi, et al., "Nucleotide Sequence of the Coat Protein Cistron and the 3' Noncoding Region of cucumber Green Mottle Mosaic Virus (Watermelon Strain) RNA", *Virology* 127: 54–64 (1983).

Ahlquist, et al., "Complete Nucleotide Sequence of Brome Mosaic Virus RNA3", *J. Mol. Biol.* 153: 23–28 (1981).

Hedgpeth, et al., "Lambda Phage Promoter Used to Enhance Expression of a Plasmid-Cloned Gene", *Mol. Gen. Genet.* 163: 197–203 (1978).

Bernard, et al., "Construction of Plasmid Cloning Vehicles that Promote Gene Expression From the Bacteriophage Lambda $p_L$ Promoter", *Gene* 5: 59–76 (1979).

Remaut, et al., "Plasmid vectors for high-efficiency expression controlled by the $p_L$ promoter of coliphage lambda", *Gene* 15: 81093 (1981).

Grimsley, et al., "Agrobacterium-mediated delivery of infectious maize streak virus into maize plants", *Nature* 325: 177–179 (1987).

Gardner, et al., "Potato spindle tuber viroid infections mediated by the Ti plasmid of *Agrobacterium tumefaciens*", *Plant Mol. Biol.* 6: 221–228 (1986).

Grimsley, et al., "'Agroinfection,' and alternative route for viral infection of plants by using the Ti plasmid", *Proc. Natl. Acad. Sci. USA* 83: 3282–3286 (1986).

Larowitz, Sondra, "Infectivity and complete nucleotide sequence of the genome of a South African isolate of maize streak virus", *Nucleic Acids Research* 16: 229–249 (1988).

Donson et al., "*Agrobacterium*-Mediated Infectivity of Cloned Digitaria Streak Virus DNA", *Virology* 162: 248–250 (1988).

Hayes, et al., "Agroinfection of *Triticum aestivum* with Cloned DNA of Wheat Dwarf Virus", *J. Gene Virol.* 69: 891–896 (1988).

Elmer, et al., "*Agrobacterium*-mediated inoculation of plants with tomato golden mosaic virus DNA's", *Plant Molecular Biology* 10: 225–234 (1988).

Gardiner, et al., "Genetic analysis of tomato golden mosaic virus: the coat protein is not required for systemic spread of symptom development", *The EMBO Journal* 7: 899–904 (1988).

Huber, et al., "Primary Structure of tyrosinase from *Streptomyces glaucescens*", *Biochemistry* 24: 6038–6044 (1985).

Tanksley and Zamir, "Double Tagging of a Male-sterile Gene in Tomato using a Morphological and Enzymatic Marker Gene", *Hort Science* 23: 387–388 (1988).

Rao and Devi, "Variation in expression of genic male sterility in pearl millet", *Journal of Heredity* 74: 34–38 (1983).

(List continued on next page.)

OTHER PUBLICATIONS

Dewey, et al., "Novel recombinations in the Maize Mitochondrial Genome Produce a Unique Transcriptional Unit in the Texas Male-Sterile Cytoplasm", *Cell* 44: 439-449 (1986).

Pearson, O. H., "Nature and Mechanisms of cytoplasmic Male Sterility in Plants: a Review 1", *Hort Science* 16(4): 482-486 (1981).

Konvicka, et al., "Untersuchungen Uber die Ursachen der Pollenstrilitat bei *Allium sativum* L.", *Z. Pfanzenzychtung* 80: 265-276 (1978).

Remy and Ambard-Bretteville, "Two Dimensional Analysis of Chloroplast Proteins from Normal and Cytoplasmic Male Sterile *Brassica napus*", *Theor. Appl. Genet.* 64: 249-253 (1983).

Padmaja, et al., "Cytogenetical Investigations on Genic Male Sterility in *Petunia axillaris* (Lam.) B.S.P.", *Cytologia* 53: 585-589 (1988).

Ebert, et al., "Genetic Polymorphism of Self-Incompatibility in Flowering Plants", *Cell* 56: 255-262 (1989).

Dawson, et al., "Modifications of the Tobacco Mosaic Virus coat Protein Gene Affecting Replication, Movement, and Symptomatology", *Phytopathology* 78: 783-789 (1988).

Goelet, et al, "Nucleotide sequence of tobacco mosaic virus RNA", *Proc. Natl. Acad. Sci. USA* 79: 5818-5822 (1982).

Shaw, W. V., "Chloramphenicol Acetyltransferase from Chloramphenicol-Resistant Bacteria", *Meth. Enzymology* 53: 737-755 (1975).

Logemann, et al., "Improved Method for the Isolation of RNA", *Anal. Biochem.* 163: 16-20 (1987).

Zagursky, et al., "Rapid and Easy Sequencing of Large Linear Double-stranded DNA DNA and Supercoiled Plasmid DNA", *Gene Anal. Tech.* 2: 89-94 (1985).

Goelet and Karn, "Tobacco Mosaic Virus Induces the Synthesis of a Family of 3' Coterminal Messenger RNA's and their Complements", *J. Mol. Biol.* 154: 541-550 (1982).

Dougherty, William, "Analysis of viral RNA Isolated from Tobacco Leaf Tissue Infected with Tobacco Etch Virus", *Virology* 131: 473-481 (1983).

Kirkegaard and Baltimore, "The Mechanism of RNA REcombination in Poliovirus", *Cell* 47: 433-443 (1986).

Bujarski and Kaesberg, "Genetic recombination between RNA components of a multipartite plant virus", *nature* 321: 528-531 (1986).

Keen, et al., "Improved broad-host-range plasmids for DNA cloning in Gram-negative bacteria", *gene* 70: 191-197 (1988).

Beck, et al., "Nucleotide sequence and exact localization of the neomycin phosphotransferase gene from transposon Tn5", *Gene* 19: 327-336 (1982).

Brisson, et al., "Expression of a bacterial gene in plants by using a viral vector", *Nature* 310: 511-514 (1984).

Rogers, et al., "Evidence for Ribosome Scanning During Translation Initiation of mRNA's in Transformed Plant Cells", *Plant Mol. Biol. Rep.* 3: 111-116 (1985).

Gooding and Hebert, "A Simple Technique of Purification of Tobacco Mosaic Virus in Large Quantities", *Phytopathology* 57: 1285 (1967).

Feinberg and Vogelstein, "A Technique for Radiolabeling DNA Restriction Endonuclease Fragments to High Specific Activity", *Anal. Biochem.* 137: 6-13 (1983).

Feinberg and Vogelstein ADDENDUM "A Technique for Radiolabeling DNA Restriction Endonuclease Fragments to High Specific Activity", *Anal. Biochem.* 137: 266-267 (1984).

Bradford, Marion "A Rapid and Sensitive Method for the Quantitation of Microgram Quantities of Protein Utilizing the Principle of Protein-Dye Binding", *Anal. Biochem.* 72: 248-254 (1976).

McDonnell, et al., "A Simplified Method for the Detection of Neomycin Phosphotransferase II Activity in Transformed Plant Tissues", *Plant Mol. Biol. Rep.* 5: 380-386 (1987).

French and Alhquist, "Characterization and Engineering of Sequences Controlling In Vivo synthesis of Brome Mosaic Virus Subgenomic RNA", *J. Virol.* 62: 2411-2420 (1988).

Kumagai, et al., "Expression and secretion of rice α-amylase by *Saccharomyces cerevisiae Gene* 94: 209-216 (1990).

O'Neill, et al., "The α-amylase genes in *Oryza sativa:* Characterization of cDNA clones and mRNA expression during seed germination", Mol. Gen. Genet. 221: 235-244 (1990).

Hamamoto, et al., "Nucleotide Sequence of the Cyclomaltodextrin Glucano-transferase (CGTase) Gene (List continued on next page.)

OTHER PUBLICATIONS from Alkalophilic *Bacillus* sp. Strain No. 38-2", *Agric. Biol. Chem.* 51: 2019-2022 (1987).

Henikoff, Steven "Unidirectional digestion with exonuclease III creates targeted breakpoints for DNA sequencing", *Gene* 28: 351-359 (1984).

Nilsson, et al., "An improved positive selection plasmid vector constructed by oligonucleotide mediated mutagenesis", *Nucleic Acids Research* 11: 8019-8030 (1983).

Gergan, et al., "Filter replicas and permanent collections of recombinant DNA plasmids", *Nucleic Acids Research* 7: 2115-2136 (1979).

Higerd and Spizizen "Isolation of Two Acetyl Esterases from Extracts of *Bacillus subtilis*", *J. Bacteriol.* 114; 1184-1192 (1973).

Ounissi and Courvalin "Nucleotide sequence of the gene ereA encoding the erythromycin esterase in *Escherichia coli*", *Gene* 35: 271-278 (1985).

Ohashi, et al., "Molecular Cloning of the Penicillin G Acylase Gene from *Arthrobacter viscosus*", *Appl. Environ. Microbiol.* 54: 2603-2607 (1988).

Wang, et al., "scientific evaluation of Tian Hua Fen (THF)-history, chemistry and application", *Pure Appl. Chem.* 58: 789-798 (1986).

Jimenez and Vazquez "Plant and Fungal Proteins and Glycoprotein Toxins Inhibiting Eukaryote Protein Synthesis", *Ann. Rev. Microbiol.* 39: 649-672 (1985).

Endo, et al., "The Mechanism of Action of Ricin and Related Toxic Lectins on Eukaryotic Ribosomes", *J. Biol. Chem.* 262: 5908-5912 (1987).

Maraganore, et al., "Purification and Characterization of Trichosanthin", *J. Biol. Chem.* 262: 11628-11633 (1987).

Collins, et al., "Primary Amino Acid Sequence of α--Trichosanthin and Molecular Models for Abrin A--chain and α-Trichosanthin", *J. Biol. Chem.* 265: 8665-8669 (1990).

McGrath, et al., "GLQ223: An inhibitor of human immunodeficiency virus replication in acutely and chronically infected cells of lymphocyte and mononuclear phagocyte lineage", *Proc. Natl. Acad. Sci. USA* 86: 2844-2848 (1989).

Shaw, et al., "Cloning of trichosanthin cDNA and its expression in *Escherichia coli*", *Gene* 97: 267-272 (1991).

Ahlquist and French, "Multicomponent RNA plant virus infection derived from clones viral cDNA", *Proc. Natl. Acad. Sci. USA* 81: 7066-7070 (1984).

Miller, et al. "synthesis of brome mosaic virus subgenomic RNA in vitro by internal initiation on (−)-sense genomic RNA", *Nature* 313: 68-70 (1985).

Takamatusu, et al., "Production of enkephalin in tobacco protoplasts using tobacco mosaic virus RNA vector", *FEBS Letters* 269: 73-76 (1990).

Dawson, et al, "A Tobacco Mosaic virus-Hybrid Expresses and Loses an Added Gene", *Virology* 172: 285-292 (1989).

Donson, et al., "Systemic expression of a bacterial gene by a tobacoo mosaic virus-based vector", *Proc. Natl. Acad. Sci. USA* 88: 7204-7208 (1991).

Chow, et al., "Isolation and DNA Sequence of a Gene Encoding α-Trichosanthin, a Type I Ribosome-inactivating Protein", *J. Biol. Chem.* 265: 8670-8674 (1990).

Saiki, et al., "enzymatic Amplification of β-Globin Genomic sequences and Restricition site Analysis for Diagnosis of Sickle Cell Anemia", *Science* 230: 1350-1354 (1985).

Hiatt, et al., "Production of antibodies in transgenic plants", *Nature* 342: 76-78 (1989).

Sijmons, et al., "Production of Correctly Processes Human Serum Albumin in Transgenic Plants", *Bio/Technology* 8: 217-221 (1990).

Hewick, et al., "A Gas-Liquid Sold Phase Peptide and Protein Sequenator", *J. Biol. Chem.* 256: 7990-7997 (1981).

von Heijne, Gunnar "A new method for predicting signal sequence cleavage sites", *Nucleic Acids Research* 14: 4683-4690 (1986).

Dawson, et al., "cDNA cloning of the complete genome of tobacco mosaic virus and production of infectious transcripts", *Proc. Natl. Acad. Sci. USA* 83: 1832-1836 (1986).

Laemmli, U. K., "Cleavage of Strucutral Proteins during the Assembly of the Head of Bacteriophage T4", *Nature* 227: 680-685 (1970).

Towbin, et al., "Electrophoretic transfer of proteins from polyacrylamide gels to nitrocellulose sheets: Procedure and some applications", *Proc. Natl. Acad. Sci. USA* 76: 4350-4354 (1979).

a  b  c          d

← UNPROCESSED TRICHOSANTHIN
← PROCESSED TRICHOSANTHIN a: SIZE MARKERS
b: YEAST ENGINEERED TO PRODUCE TRICOSANTHIN
d: PURIFIED EXTRACT OF PLANTS THAT HAVE BEEN INDUCED TO PRODUCE TRICHOSANTHIN USING THE GENEWARE SYSTEM

α-trichosanthin pBGC152 (11.2 kb)

Labels around plasmid: ClaI, XhoI, 30K, XhoI, XbaI, Ocp, TMV RNA (+7492), KpnI, 183/54K, BamHI, 126K, pBR322, TMV RNA (+1)

Inset: 126K — 68 nt — SP6 promoter

FIG. 3a

.tsp
GTTTAAATACGCTCGAGG ATG ATC AGA TTC TTA GTC CTC TCT TTG CTA ATT CTC ACC CTC TTC
      XhoI   Start codon  Met Ile Arg Phe Leu Val Leu Ser Leu Leu Ile Leu Thr Leu Phe Signal peptide  -1  +1  Mature α-trichosanthin
CTA ACA ACT CCT GCT GTG GAG GGC | GAT GTT AGC TTC CGT TTA TCA
Leu Thr Thr Pro Ala Val Glu Gly | Asp Val Ser Phe Arg Leu Ser TO FIG. 3a

FIG. 3b

PLANT VIRAL VECTORS HAVING HETEROLOGOUS SUBGENOMIC PROMOTERS FOR SYSTEMIC EXPRESSION OF FOREIGN GENES

SUMMARY OF FUNDING

The present invention was funded in part by a grant from the National Science Foundation (NSF).

CROSS-REFERENCE TO RELATED APPLICATIONS

The present application is a continuation-in-part of applications Ser. No. 600,244, filed Oct. 22, 1990, Ser. No. 641,617, filed Jan. 16, 1991, Ser. No. 737,899 filed Jul. 26, 1991 and Ser. No. 739,143 filed Aug. 1, 1991 (all now abandoned). Ser. No. 600,244 is a continuation of application Ser. No. 310,881, filed Feb. 17, 1989, now abandoned, which is a continuation-in-part of applications Ser. No. 160,766 and 160,771, both filed on Feb. 26, 1988 and now abandoned. Ser. No. 641,617 is a continuation of application Ser. No 347,637, filed May 5, 1989, now abandoned. Ser. No. 737,899 is a continuation of application, Ser. No. 363,138, filed Jun. 8, 1989, now abandoned, which is a continuation-in-part of application Ser. No. 219,279, filed Jul. 15, 1988 and now abandoned. The disclosures of all of the foregoing are incorporated by reference.

BACKGROUND OF THE INVENTION

The present invention relates to plant viral vectors which are (a) self-replicating; (b) capable of systemic infection in a host; (c) contain, or are capable of containing, nucleic acid sequences foreign to the native virus, which are transcribed or expressed in the host plant; and (d) stable, especially for the transcription and expression of foreign nucleic acid sequences.

Viruses are a unique class of infectious agents whose distinctive features are their simple organization and their mechanism of replication. In fact, a complete viral particle, or virion, may be regarded mainly as a block of genetic material (either DNA or RNA) capable of autonomous replication, surrounded by a protein coat and sometimes by an additional membranous envelope such as in the case of alpha viruses. The coat protects the virus from the environment and serves as a vehicle for transmission from one host cell to another.

Unlike cells, viruses do not grow in size and then divide, because they contain within their coats few (or none) of the biosynthetic enzymes and other machinery required for their replication. Rather, viruses multiply in cells by the synthesis of their separate components, followed by assembly. Thus, the viral nucleic acid, after shedding its coat, comes into contact with the appropriate cell machinery where it specifies the synthesis of proteins required for viral reproduction. The viral nucleic acid is then itself replicated through the use of both viral and cellular enzymes. The components of the viral coat are formed and the nucleic acid and coat components are finally assembled. With some viruses, replication is initiated by enzymes present in virions.

A given plant virus may contain either DNA or RNA, which may be either single- or double-stranded. The portion of nucleic acid in a virion varies from about 1% to about 50%. The amount of genetic information per virion varies from about 3 kb to 300 kb per strand. The diversity of virus-specific proteins varies accordingly. One example of double-stranded DNA containing plant viruses includes, but is not limited to, caulimoviruses such as Cauliflower mosaic virus (CaMV). Representative plant viruses which contain single-stranded DNA are Cassava latent virus, bean golden mosaic virus (BGMV), and Chloris striate mosaic virus. Rice dwarf virus and wound tumor virus are examples of double-stranded RNA plant viruses. Single-stranded RNA plant viruses include tobacco mosaic virus (TMV), turnip yellow mosaic virus (TYMV), rice necrosis virus (RNV) and brome mosaic virus (BMV). The RNA in single-stranded RNA viruses may be either a plus (+) or a minus (−) strand. For general information concerning plant viruses, see Grierson, D. et al. (1); Gluzman, Y. et al. (2).

One means for classifying plant viruses is based on the genome organization. Although many plant viruses have RNA genomes, organization of genetic information differs between groups. The genome of most monopartite plant RNA viruses is a single-stranded molecule of (+)-sense. There are at least 11 major groups of viruses with this type of genome. An example of this type of virus is TMV. At least six major groups of plant RNA viruses have a bipartite genome. In these, the genome usually consists of two distinct (+)-sense single-stranded RNA molecules encapsidated in separate particles. Both RNAs are required for infectivity. Cowpea mosaic virus (CPMW) is one example of a bipartite plant virus. A third major group, containing at least six major types of plant viruses, is tripartite, with three (+)-sense single-stranded RNA molecules. Each strand is separately encapsidated, and all three are required for infectivity. An example of a tripartite plant virus is alfalfa mosaic virus (AMV). Many plant viruses also have smaller subgenomic mRNAs that are synthesized to amplify a specific gene product. One group of plant viruses having a single-stranded DNA genome are the geminiviruses, such as Cassava latent virus (CLV) and maize streak virus (MSV). Several plant viruses have been cloned to study their nucleic acid, in anticipation of their use as plant transformation vectors. Examples of viruses cloned include BMV, Ahlguist, P. and Janda, M. (3); TMV, Dawson W. O. et al. (4); CaMV, Lebeurier, G. et al. (5); and BGMV, Morinaga, T. et al. (6).

Techniques have been developed which are utilized to transform many species of organisms. Hosts which are capable of being transformed by these techniques include bacteria, yeast, fungus, animal cells and plant cells or tissue. Transformation is accomplished by using a vector which is self-replicating and which is compatible with the desired host. The vectors are generally based on either a plasmid or a virus. Foreign DNA is inserted into the vector, which is then used to transform the appropriate host. The transformed host is then identified by selection or screening. For further information concerning the transformation of these hosts, see *Molecular Cloning* (7) *DNA Cloning* (8); Grierson, D. et al. (1), and *Methods in Enzymology*, (9).

Viruses that have been shown to be useful for the transformation of plant hosts include CaV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV), Brisson, N. et al. (10) (CaV), and Guzman et al. (2). Pseudovirus particles for use in expressing foreign DNA in many hosts, including plants, is described in WO 87/06261.

When the virus is a DNA virus, the constructions can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression of non-viral foreign genes in plants is demonstrated by the above references as well as by Dawson, W. O. et al. (11); Takamatsu, N. et al. (12); French, R. et al. (13); and Takamatsu, N. et al. (14). However, none of these viral vectors have been capable of systemic spread in the plant and expression of the non-viral foreign genes in the majority of the plant cells in the whole plant. Another disadvantage of many of the prior art viral vectors is that they are not stable for the maintenance of non-viral foreign genes. See, for example, Dawson, W. O. et al. (11). Thus, despite all of this activity to develop plant viral vectors and viruses, a need still exists for a stable recombinant plant virus capable of systemic infection in the host plant and stable expression of the foreign DNA.

SUMMARY OF THE INVENTION

The present invention is directed to recombinant plant viral nucleic acids and recombinant viruses which are stable for maintenance and transcription or expression of non-native (foreign) nucleic acid sequences and which are capable of systemically transcribing or expressing such foreign sequences in the host plant. More specifically, recombinant plant viral nucleic acids according to the present invention comprise a native plant viral subgenomic promoter, at least one non-native plant viral subgenomic promoter, a plant viral coat protein coding sequence, and optionally, at least one non-native, nucleic acid sequence.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted.

The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters.

Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) in the host to produce the desired product. Such products include therapeutic and other useful polypeptides or proteins such as, but not limited to, enzymes, complex biomolecules, ribozymes, or polypeptide or protein products resulting from antisense RNA expression.

BRIEF DESCRIPTION OF THE FIGURES

FIG. 2 is an autoradiograph of a Western analysis of the production of α-trichosanthin in $N.$ $benthamiana$ infected in accordance with the present invention. Lane a is molecular size markers, lanes b and c are extracts from yeast engineered to produce α-trichosanthin and lane d is a extract from *N. benthamiana.*

FIGS. 3A and 3B illustrate the α-trichosanthin expression vector, pBGC152. This plasmid contains the TMV-U1 126-, 183-, and 30-kDa open reading frames (ORFs), the ORSV coat protein gene (Ocp), the SP6 promoter, the α-trichosanthin gene, and part of the pBR322 plasmid. The TAA stop codon in the 30K ORF is underlined and a bar (:) divides the putative signal peptide from the mature peptide. The TMV-U1 subgenomic promoter located within the minus strand of the 30K ORF controls the expression of α-trichosanthin. The putative transcription start point (tsp) of the subgenomic RNA is indicated with a period(.).

DETAILED DESCRIPTION OF THE INVENTION

Figure 1:
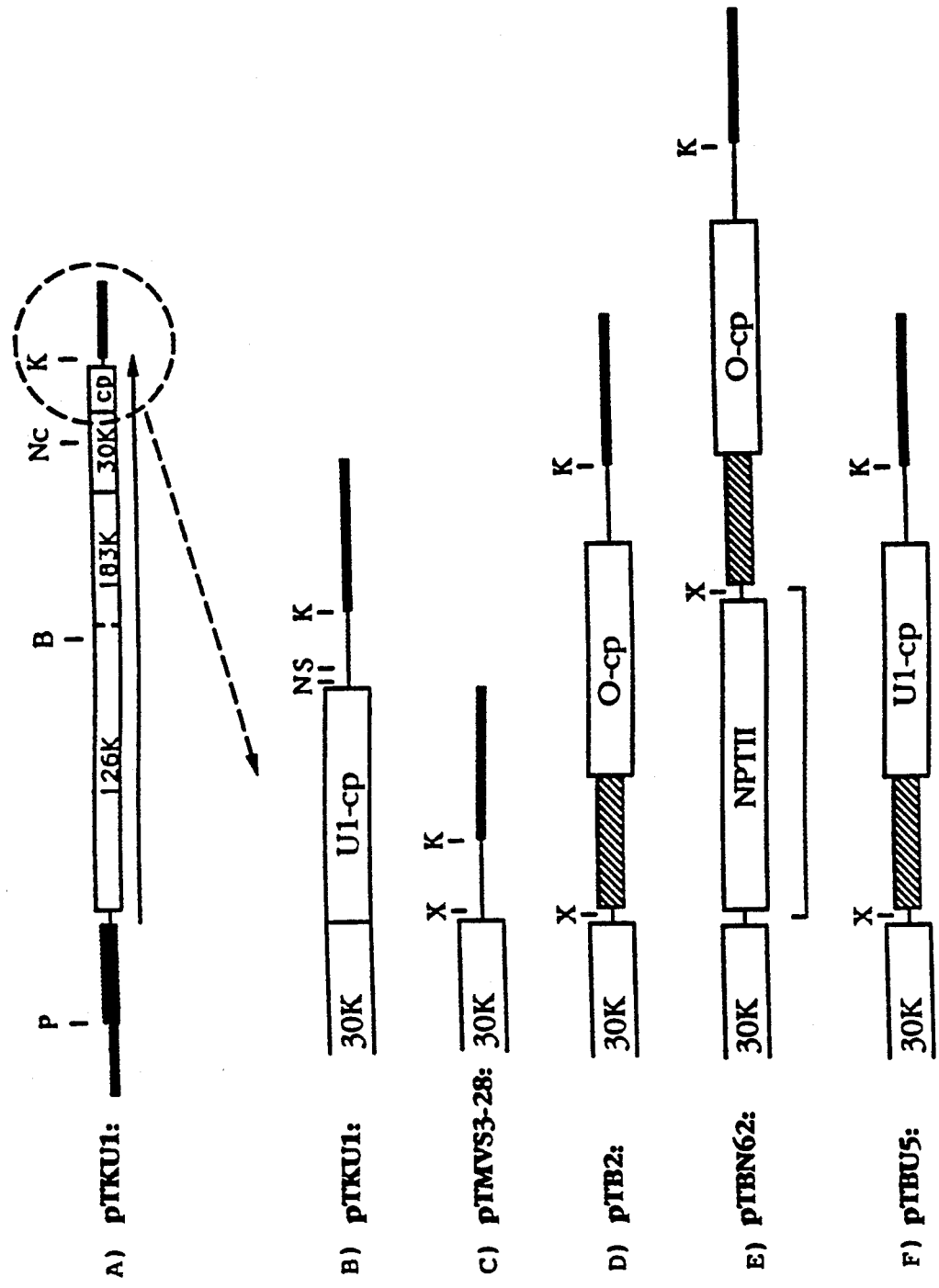
FIG. 1 illustrates several vectors prepared in accordance with the present invention and restriction sites. U1 is the native plant viral nucleic acid, O is a non-native plant viral nucleic acid, and the hatched area is a non-native plant viral subgenomic promoter. The restriction sites are: X-XhoI, N-NsiI, K-KpnI, S-SplI, B-BamHI, No-NcoI, P-PstI. The hatched box (e.g., in TB2) represents the promoter of TMV-O, i.e., 203 bp upstream of the coat protein initiation codon, and the stipled box represents a phage promoter. The open boxes represent open reading frames, and the solid boxes represent cloning vector sequences. The vectors are as follows: A) and B) pTKU1, C) pTMVS3-28, D) pTB2, E) pTBN62 and F) pTBU5.

The present invention is directed to recombinant plant viral nucleic acids and recombinant viruses which are stable for maintenance and transcription or expression of non-native (foreign) nucleic acid sequences and which are capable of systemically transcribing or expressing such foreign sequences in the host plant. More specifically, recombinant plant viral nucleic acids according to the present invention comprise a native plant viral subgenomic promoter, at least one non-native plant viral subgenomic promoter, a plant viral coat protein coding sequence, and optionally, at least one non-native, nucleic acid sequence.

In one embodiment, a plant viral nucleic acid is provided in which the native coat protein coding sequence has been deleted from a viral nucleic acid, a non-native plant viral coat protein coding sequence and a non-native promoter, preferably the subgenomic promoter of the non-native coat protein coding sequence, capable of expression in the plant host, packaging of the recombinant plant viral nucleic acid, and ensuring a systemic infection of the host by the recombinant plant viral nucleic acid, has been inserted. Alternatively, the coat protein gene may be inactivated by insertion of the non-native nucleic acid sequence within it, such that a fusion protein is produced. The recombinant plant viral nucleic acid may contain one or more additional non-native subgenomic promoters. Each non-native subgenomic promoter is capable of transcribing or expressing adjacent genes or nucleic acid sequences in the plant host and incapable of recombination with each other and with native subgenomic promoters. Non-native (foreign) nucleic acid sequences may be inserted adjacent the native plant viral subgenomic promoter or the native and a non-native plant viral subgenomic promoters if more than one nucleic acid sequence is included. The non-native nucleic acid sequences are transcribed or expressed in the host plant under control of the subgenomic promoter to produce the desired products.

In a second embodiment, a recombinant plant viral nucleic acid is provided as in the first embodiment except that the native coat protein coding sequence is placed adjacent one of the non-native coat protein subgenomic promoters instead of a non-native coat protein coding sequence.

In a third embodiment, a recombinant plant viral nucleic acid is provided in which the native coat protein gene is adjacent its subgenomic promoter and one or more non-native subgenomic promoters have been inserted into the viral nucleic acid. The inserted non-native subgenomic promoters are capable of transcribing or expressing adjacent genes in a plant host and are incapable of recombination with each other and with native subgenomic promoters. Non-native nucleic acid sequences may be inserted adjacent the non-native subgenomic plant viral promoters such that said sequences are transcribed or expressed in the host plant under control of the subgenomic promoters to produce the desired product.

In a fourth embodiment, a recombinant plant viral nucleic acid is provided as in the third embodiment except that the native coat protein coding sequence is replaced by a non-native coat protein coding sequence.

The viral vectors are encapsidated by the coat proteins encoded by the recombinant plant viral nucleic acid to produce a recombinant plant virus. The recombinant plant viral nucleic acid or recombinant plant virus is used to infect appropriate host plants. The recombinant plant viral nucleic acid is capable of replication in the host, systemic spread in the host, and transcription or expression of foreign gene(s) in the host to produce the desired product.

In order to provide a clear and consistent understanding of the specification and the claims, including the scope given herein to such terms, the following definitions are provided:

Adjacent: A position in a nucleotide sequence immediately 5' or 3' to a defined sequence.

Anti-Sense Mechanism: A type of gene regulation based on controlling the rate of translation of mRNA to protein due to the presence in a cell of an RNA molecule complementary to at least a portion of the mRNA being translated.

Cell Culture: A proliferating mass of cells which may be in either an undifferentiated or differentiated state.

Chimeric Sequence or Gene: A nucleotide sequence derived from at least two heterologous parts. The sequence may comprise DNA or RNA.

Coding Sequence: A deoxyribonucleotide sequence which, when transcribed and translated, results in the formation of a cellular polypeptide or a ribonucleotide sequence which, when translated, results in the formation of a cellular polypeptide.

Compatible: The capability of operating with other components of a system. A vector or plant viral nucleic acid which is compatible with a host is one which is capable of replicating in that host. A coat protein which is compatible with a viral nucleotide sequence is one capable of encapsidating that viral sequence.

Gene: A discrete nucleic acid sequence responsible for a discrete cellular product.

Host: A cell, tissue or organism capable of replicating a vector or plant viral nucleic acid and which is capable of being infected by a virus containing the viral vector or plant viral nucleic acid. This term is intended to include procaryotic and eukaryotic cells, organs, tissues or organisms, where appropriate.

Infection: The ability of a virus to transfer its nucleic acid to a host or introduce viral nucleic acid into a host, wherein the viral nucleic acid is replicated, viral proteins are synthesized, and new viral particles assembled. In this context, the terms "transmissible" and "infective" are used interchangeably herein.

Non-Native: Any RNA sequence that promotes production of subgenomic mRNA including, but not limited to, 1) plant viral promoters such as ORSV and vrome mosaic virus, 2) viral promoters from other organisms such as human sindbis viral promoter, and 3) synthetic promoters.

Phenotypic Trait: An observable property resulting from the expression of a gene.

Plant Cell: The structural and physiological unit of plants, consisting of a protoplast and the cell wall.

Plant Organ: A distinct and visibly differentiated part of a plant, such as root, stem, leaf or embryo.

Plant Tissue: Any tissue of a plant in planta or in culture. This term is intended to include a whole plant, plant cell, plant organ, protoplast, cell culture, or any group of plant cells organized into a structural and functional unit.

Production Cell: A cell, tissue or organism capable of replicating a vector or a viral vector, but which is not necessarily a host to the virus. This term is intended to include prokaryotic and eukaryotic cells, organs, tissues or organisms, such as bacteria, yeast, fungus and plant tissue.

Promoter: The 5'-flanking, non-coding sequence adjacent a coding sequence which is involved in the initiation of transcription of the coding sequence.

Protoplast: An isolated plant cell without cell walls, having the potency for regeneration into cell culture or a whole plant.

Recombinant Plant Viral Nucleic Acid: Plant viral nucleic acid which has been modified to contain nonnative nucleic acid sequences.

Recombinant Plant Virus: A plant virus containing the recombinant plant viral nucleic acid.

Subgenomic Promoter: A promoter of a subgenomic mRNA of a viral nucleic acid.

Substantial Sequence Homology: Denotes nucleotide sequences that are substantially functionally equivalent to one another. Nucleotide differences between such sequences having substantial sequence homology will be de minimus in affecting function of the gene products or an RNA coded for by such sequence.

Transcription: Production of an RNA molecule by RNA polymerase as a complementary copy of a DNA sequence.

Vector: A self-replicating DNA molecule which transfers a DNA segment between cells.

Virus: An infectious agent composed of a nucleic acid encapsidated in a protein. A virus may be a mono-, di-, tri- or multi-partite virus, as described above.

The present invention provides for the infection of a plant host by a recombinant plant virus containing recombinant plant viral nucleic acid or by the recombinant plant viral nucleic acid which contains one or more non-native nucleic acid sequences which are transcribed or expressed in the infected tissues of the plant host. The product of the coding sequences may be recovered from the plant or cause a phenotypic trait, such as male sterility, in the plant.

The present invention has a number of advantages, one of which is that the transformation and regeneration of target organisms is unnecessary. Another advantage is that it is unnecessary to develop vectors which integrate a desired coding sequence in the genome of the target organism. Existing organisms can be altered with a new coding sequence without the need of going through a germ cell. The present invention also gives the option of applying the coding sequence to the desired organism, tissue, organ or cell. Recombinant plant viral nucleic acid is also stable for the foreign coding sequences, and the recombinant plant virus or recombinant plant viral nucleic acid is capable of systemic infection in the plant host.

Chimeric genes and vectors and recombinant plant viral nucleic acids according to this invention are constructed using techniques well known in the art. Suitable techniques have been described in *Molecular Cloning* (7); *Methods in Enzymol.* (9); and *DNA Cloning* (8). Medium compositions have been described in Miller, J. H. (15), as well as the references previously identified. DNA manipulations and enzyme treatments are carried out in accordance with manufacturers' recommended procedures.

An important feature of the present invention is the preparation of recombinant plant viral nucleic acids (RPVNA) which are capable of replication and systemic spread in a compatible plant host, and which contain one or more non-native subgenomic promoters which are capable of transcribing or expressing adjacent nucleic acid sequences in the plant host. The RPVNA may be further modified to delete all or part of the native coat protein coding sequence and to contain a non-native coat protein coding sequence under control of the native or one of the non-native subgenomic promoters, or put the native coat protein coding sequence under the control of a non-native plant viral subgenomic promoter. The RPVNA have substantial sequence homology to plant viral nucleotide sequences. A partial listing of suitable viruses has been described above. The nucleotide sequence may be an RNA, DNA, cDNA or chemically synthesized RNA or DNA.

The first step in achieving any of the features of the invention is to modify the nucleotide sequences of the plant viral nucleotide sequence by known conventional techniques such that one or more non-native subgenomic promoters are inserted into the plant viral nucleic acid without destroying the biological function of the plant viral nucleic acid. The subgenomic promoters are capable of transcribing or expressing adjacent nucleic acid sequences in a plant host infected by the recombinant plant viral nucleic acid or recombinant plant virus. The native coat protein coding sequence may be deleted in two embodiments, placed under the control of a non-native subgenomic promoter in a second embodiment, or retained in a further embodiment. If it is deleted or otherwise inactivated, a non-native coat protein gene is inserted under control of one of the non-native subgenomic promoters, or optionally under control of the native coat protein gene subgenomic promoter. The non-native coat protein is capable of encapsidating the recombinant plant viral nucleic acid to produce a recombinant plant virus. Thus, the recombinant plant viral nucleic acid contains a coat protein coding sequence, which may be native or a nonnative coat protein coding sequence, under control of one of the native or non-native subgenomic promoters. The coat protein is involved in the systemic infection of the plant host.

Some of the viruses which meet this requirement, and are therefore suitable, include viruses from the tobacco mosaic virus group such as Tobacco Mosaic virus (TMV), Cowpea Mosaic virus (CMV), Alfalfa Mosaic virus (AMV), Cucumber Green Mottle Mosaic virus watermelon strain (CGMMV-W) and Oat Mosaic virus (OMV) and viruses from the brome mosaic virus group such as Brome Mosaic virus (MBV), broad bean mottle virus and cowpea chlorotic mottle virus. Additional suitable viruses include Rice Necrosis virus (RNV), and geminiviruses such as tomato golden mosaic virus (TGMV), Cassava latent virus (CLV) and maize streak virus (MSV). Each of these groups of suitable viruses is characterized below.

Tobacco Mosaic Virus Group

Tobacco Mosaic virus (TMV) is a member of the Tobamoviruses. The TMV virion is a tubular filament, and comprises coat protein sub-units arranged in a single right-handed helix with the single-stranded RNA intercalated between the turns of the helix. TMV infects tobacco as well as other plants. TMV is transmitted mechanically and may remain infective for a year or more in soil or dried leaf tissue.

The TMV virions may be inactivated by subjection to an environment with a pH of less than 3 or greater than 8, or by formaldehyde or iodine. Preparations of TMV may be obtained from plant tissues by $(NH_4)_2SO_4$ precipitation, followed by differential centrifugation.

The TMV single-stranded RNA genome is about 6400 nucleotides long, and is capped at the 5′ end but not polyadenylated. The genomic RNA can serve as mRNA for a protein of a molecular weight of about 130,000 (130K) and another produced by read-through of molecular weight about 180,000 (180K). However, it cannot function as a messenger for the synthesis of coat protein. Other genes are expressed during infection by the formation of monocistronic, 3′-coterminal subgenomic mRNAs, including one (LMC) encoding the 17.5K coat protein and another ($I_2$) encoding a 30K protein. The 30K protein has been detected in infected protoplasts (16), and it is involved in the cell-to-cell transport of the virus in an infected plant (17). The functions of the two large proteins are unknown.

Several double-stranded RNA molecules, including double-stranded RNAs corresponding to the genomic, $I_2$ and LMC RNAs, have been detected in plant tissues infected with TMV. These RNA molecules are presumably intermediates in genome replication and/or mRNA synthesis processes which appear to occur by different mechanisms.

TMV assembly apparently occurs in plant cell cytoplasm, although it has been suggested that some TMV assembly may occur in chloroplasts since transcripts of ctDNA have been detected in purified TMV virions. Initiation of TMV assembly occurs by interaction between ring-shaped aggregates ("discs") of coat protein (each disc consisting of two layers of 17 subunits) and a unique internal nucleation site in the RNA; a hairpin region about 900 nucleotides from the 3′ end in the common strain of TMV. Any RNA, including subgenomic RNAs containing this site, may be packaged into virions. The discs apparently assume a helical form on interaction with the RNA, and assembly (elongation) then proceeds in both directions (but much more rapidly in the 3′- to 5′-direction from the nucleation site).

Another member of the Tobamoviruses, the Cucumber green mottle mosaic virus watermelon strain (CGMMV-W) is related to the cucumber virus. Noru, Y. et al. (18). The coat protein of CGMMV-W interacts with RNA of both TMV and CGMMV to assemble viral particles in vitro. Kurisu et al. (19).

Several strains of the tobamovirus group are divided into two subgroups, on the basis of the location of the assembly of origin. Fukuda, M. et al. (20). Subgroup I, which includes the vulgare, OM, and tomato strain, has an origin of assembly about 800–1000 nucleotides from the 3′ end of the RNA genome, and outside the coat protein cistron. Lebeurier, G. et al. (21); and Fukuda, M. et al. (22). Subgroup II, which includes CGMMV-W and cornpea strain (Cc) has an origin of assembly about 300–500 nucleotides from the 3′ end of the RNA genome and within the coat-protein cistron. Fukuda, M. et al. (22). The coat protein cistron of CGMMV-W is located at nucleotides 176–661 from the 3′ end. The 3′ noncoding region is 175 nucleotides long. The origin of assembly is positioned within the coat protein cistron. Meshi, T. et al. (23).

Brome Mosaic Virus Group

Brome mosaic virus (BV) is a member of a group of tripartite, single-stranded, RNA-containing plant viruses commonly referred to as the bromoviruses. Each member of the bromoviruses infects a narrow range of plants. Mechanical transmission of bromoviruses occurs readily, and some members are transmitted by beetles. In addition to BV, other bromoviruses include broad bean mottle virus and cowpea chlorotic mottle virus.

Typically, a bromovirus virion is icosahedral, with a diameter of about 26 mm, containing a single species of coat protein. The bromovirus genome has three molecules of linear, positive-sense, single-stranded RNA, and the coat protein mRNA is also encapsidated. The RNAs each have a capped 5′ end, and a tRNA-like structure (which accepts tyrosine) at the 3′ end. Virus assembly occurs in the cytoplasm. The complete nucleotide sequence of BMV has been identified and characterized as described by Alquist et al. (24).

Rice Necrosis Virus

Rice Necrosis virus is a member of the Potato Virus Y Group or Potyviruses. The Rice Necrosis virion is a flexuous filament comprising one type of coat protein (molecular weight about 32,000 to about 36,000) and one molecule of linear positive-sense single-stranded RNA. The Rice Necrosis virus is transmitted by *Polvmvxa araminis* (a eukaryotic intracellular parasite found in plants, algae and fungi).

Geminiviruses

Geminiviruses are a group of small, single-stranded DNA-containing plant viruses with virions of unique morphology. Each virion consists of a pair of isometric particles (incomplete icosahedra), composed of a single type of protein (with a molecular weight of about $2.7-3.4 \times 10^4$). Each geminivirus virion contains one molecule of circular, positive-sense, single-stranded DNA. In some geminiviruses (i.e., Cassava latent virus and bean golden mosaic cirus) the genome appears to be bipartite, containing two single-stranded DNA molecules.

The nucleic acid of any suitable plant virus can be utilized to prepare the recombinant plant viral nucleic acid of the present invention. The nucleotide sequence of the plant virus is modified, using conventional techniques, by the insertion of one or more subgenomic promoters into the plant viral nucleic acid. The subgenomic promoters are capable of functioning in the specific host plant. For example, if the host is tobacco, TMV will be utilized. The inserted subgenomic promoters must be compatible with the TMV nucleic acid and capable of directing transcription or expression of adjacent nucleic acid sequences in tobacco.

The native coat protein gene could also be retained and a non-native nucleic acid sequence inserted within it to create a fusion protein as discussed below. In this example, a non-native coat protein gene is also utilized.

The native or non-native coat protein gene is utilized in the recombinant plant viral nucleic acid. Whichever gene is utilized may be positioned adjacent its natural subgenomic promoter or adjacent one of the other available subgenomic promoters. The non-native coat protein, as is the case for the native coat protein, is capable of encapsidating the recombinant plant viral nucleic acid and providing for systemic spread of the recombinant plant viral nucleic acid in the host plant. The coat protein is selected to provide a systemic infection in the plant host of interest. For example, the TMV-O coat protein provides systemic infection in *N. benthamiana*, whereas TMV-U1 coat protein provides systemic infection in *N. tabacum*.

The recombinant plant viral nucleic acid is prepared by cloning viral nucleic acid in an appropriate production cell. If the viral nucleic acid is DNA, it can be cloned directly into a suitable vector using conventional techniques. One technique is to attach an origin of replication to the viral DNA which is compatible with the production cell. If the viral nucleic acid is RNA, a full-length DNA copy of the viral genome is first prepared by well-known procedures. For example, the viral RNA is transcribed into DNA using reverse transcriptase to produce subgenomic DNA pieces, and a double-stranded DNA made using DNA polymerases. The DNA is then cloned into appropriate vectors and cloned into a production cell. The DNA pieces are mapped and combined in proper sequence to produce a full-length DNA copy of the viral RNA genome, if necessary. DNA sequences for the subgenomic promoters, with or without a coat protein gene, are then inserted into the nucleic acid at non-essential sites, according to the particular embodiment of the invention utilized. Non-essential sites are those that do not affect the biological properties of the plant viral nucleic acid. Since the RNA genome is the infective agent, the cDNA is positioned adjacent a suitable promoter so that the RNA is produced in the production cell. The RNA is capped using conventional techniques, if the capped RNA is the infective agent.

A second feature of the present invention is a recombinant plant viral nucleic acid which further comprises one or more non-native nucleic acid sequences capable of being transcribed in the plant host. The non-native nucleic acid sequence is placed adjacent one or the non-native viral subgenomic promoters and/or the native coat protein gene promoter depending on the particular embodiment used. The non-native nucleic acid is inserted by conventional techniques, or the non-native nucleic acid sequence can be inserted into or adjacent the native coat protein coding sequence such that a fusion protein is produced. The non-native nucleic acid sequence which is transcribed may be transcribed as an RNA which is capable of regulating the expression of a phenotypic trait by an anti-sense mechanism. Alternatively, the non-native nucleic acid sequence in the recombinant plant viral nucleic acid may be transcribed and translated in the plant host, to produce a phenotypic trait. The non-native nucleic acid sequence(s) may also code for the expression of more than one phenotypic trait. The recombinant plant viral nucleic acid containing the non-native nucleic acid sequence is constructed using conventional techniques such that non-native nucleic acid sequence(s) are in proper orientation to whichever viral subgenomic promoter is utilized.

Useful phenotypic traits in plant cells include, but are not limited to, improved tolerance to herbicides, improved tolerance to extremes of heat or cold, drought, salinity or osmotic stress; improved resistance to pests (insects, nematodes or arachnids) or diseases (fungal, bacterial or viral) production of enzymes or secondary metabolites; male or female sterility; dwarfness; early maturity; improved yield, vigor, heterosis, nutritional qualities, flavor or processing properties, and the like. Other examples include the production of important proteins or other products for commercial use, such as lipase, melanin, pigments, antibodies, hormones, pharmaceuticals, antibiotics and the like. Another useful phenotypic trait is the production of degradative or inhibitory enzymes, such as are utilized to prevent or inhibit root development in malting barley. The phenotypic trait may also be a secondary metabolite whose production is desired in a bioreactor.

A double-stranded DNA of the recombinant plant viral nucleic acid or a complementary copy of the recombinant plant viral nucleic acid is cloned into a production cell. If the viral nucleic acid is an RNA molecule, the nucleic acid (cDNA) is first attached to a promoter which is compatible with the production cell. The RPVNA can then be cloned into any suitable vector which is compatible with the production cell. In this manner, only RNA copies of the chimeric nucleotide sequence are produced in the production cell. For example, if the production cell is *E. coli,* the lac promoter can be utilized. If the production cell is a plant cell, the CaMV promoter can be used. The production cell can be a eukaryotic cell such as yeast, plant or animal, if viral RNA must be capped for biological activity. Alternatively, the RPVNA is inserted in a vector adjacent a promoter which is compatible with the production cell. If the viral nucleic acid is a DNA molecule, it can be cloned directly into a production cell by attaching it to an origin of replication which is compatible with the production cell. In this manner, DNA copies of the chimeric nucleotide sequence are produced in the production cell.

A promoter is a DNA sequence that directs RNA polymerase to bind to DNA and to initiate RNA synthesis. There are strong promoters and weak promoters. Among the strong promoters are lacuv5, trp, tac, trp-lacuv5, λpl, ompF, and bla. A useful promoter for expressing foreign genes in *E. coli* is one which is both strong and regulated. The λp1 promoter of bacteriophage λ is a strong, well-regulated promoter. Hedgpeth, J. M. et al. (25); Bernard, H. M. et al. (26); Remaut, E. P. et al. (27).

A gene encoding a temperature-sensitive λ repressor such as λcIts 857 may be included in the cloning vector. Bernard et al. (26). At low temperature (31° C.), the $p_l$ promoter is maintained in a repressed state by the cI-gene product. Raising the temperature destroys the activity of the repressor. The $p_l$ promoter then directs the synthesis of large quantities of mRNA. In this way, *E. coli* production cells may grow to the desired concentration before producing the products encoded within the vectors. Similarly, a temperature-sensitive promoter may be activated at the desired time by adjusting the temperature of the culture.

It may be advantageous to assemble a plasmid that can conditionally attain very high copy numbers. For example, the pAS2 plasmid containing a lac or tac promoter will achieve very high copy numbers at 42° C. The lac repressor, present in the pAS2 plasmid, is then inactivated by isopropyl-β-D-thiogalactoside to allow synthesis of mRNA.

A further alternative when creating the RPVNA is to prepare more than one nucleic acid (i.e., to prepare the nucleic acids necessary for a multipartite viral vector construct). In this case, each nucleic acid would require its own origin of assembly. Each nucleic acid could be prepared to contain a subgenomic promoter and a non-native nucleic acid.

Alternatively, the insertion of a non-native nucleic acid into the nucleic acid of a monopartite virus may result in the creation of two nucleic acids (i.e., the nucleic acid necessary for the creation of a bipartite viral vector). This would be advantageous when it is desirable to keep the replication and transcription or expression of the non-native nucleic acid separate from the replication and translation of some of the coding sequences of the native nucleic acid. Each nucleic acid would have to have its own origin of assembly.

A third feature of the present invention is a virus or viral particle. The virus comprises a RPVNA as described above which has been encapsidated. The resulting product is then capable of infecting an appropriate plant host. The RPVNA sequence is transcribed and/or translated within the plant host to produce the desired product.

In one embodiment of the present invention, the recombinant plant viral nucleic acid is encapsidated by a heterologous capsid. Most commonly, this embodiment will make use of a rod-shaped capsid because of its ability to encapsidate a longer RPVNA than the more geometrically constrained icosahedral capsid or spherical capsid. The use of a rod-shaped capsid permits incorporation of a larger non-native nucleic acid to form the RPVNA. Such a rod-shaped capsid is most advantageous when more than one non-native nucleic acid is present in the RPVNA.

Another feature of the invention is a vector containing the RPVNA as described above. The RPVNA is adjacent a nucleotide sequence selected from the group consisting of a production cell promoter or an origin of replication compatible with the production cell. The vector is utilized to transform a production cell which will then produce the RPVNA in quantity. The production cell may be any cell which is compatible with the vector, and may be prokaryotic or eukaryotic. However, if the viral RNA (RPVNA) must be capped in order to be active, the production cell must be capable of capping the viral RNA, such as a eukaryotic production cell.

A further feature of the present invention is a host which has been infected by the recombinant plant virus or viral nucleic acid. After introduction into a host, the host contains the RPVNA which is capable of self-replication, encapsidation and systemic spread. The host can be infected with the recombinant plant virus by conventional techniques. Suitable techniques include, but are not limited to, leaf abrasion, abrasion in solution, high velocity water spray and other injury of a host as well as imbibing host seeds with water containing the recombinant plant virus. More specifically, suitable techniques include:

(a) Hand Inoculations. Hand inoculations of the encapsidated vector are performed using a neutral pH, low molarity phosphate buffer, with the addition of celite or carborundum (usually about 1%) One to four drops of the preparation is put onto the upper surface of a leaf and gently rubbed.

(b) Mechanized Inoculations of Plant Beds. Plant bed inoculations are performed by spraying ($CO_2$-propelled) the vector solution into a tractor-driven mower while cutting the leaves. Alternatively, the plant bed is mowed and the vector solution sprayed immediately onto the cut leaves.

(c) High Pressure Spray of Single Leaves. Single plant inoculations can also be performed by spraying the leaves with a narrow, directed spray (50 psi, 6–12 inches from the leaf) containing approximately 1% carborundum in the buffered vector solution.

An alternative method for introducing a RPVNA into a plant host is a technique known as agroinfection or Agrobacterium-mediated transformation (sometimes called Agro-infection) as described by Grimsley, N. et al. (28). This technique makes use of a common feature of Agrobacterium which colonizes plants by transferring a portion of their DNA (the T-DNA) into a host cell, where it becomes integrated into nuclear DNA. The T-DNA is defined by border sequences which are 25 base pairs long, and any DNA between these border sequences is transferred to the plant cells as well. The insertion of a RPVNA between the T-DNA border sequences results in transfer of the RPVNA to the plant cells, where the RPVNA is replicated, and then spreads systemically through the plant. Agro-infection has been accomplished with potato spindle tuber viroid (PSTV) (Gardner, R. C. et al. (29)); CaV (Grimsley, N. et al. (30)); MSV (Grimsley, N. et al. (28), supra) and Lazarowitz, S. C. (31)), digitaria streak virus (Donson, J. et al. (32)), wheat dwarf virus (Hayes, R. J. et al. (33)) and tomato golden mosaic virus (TGMV) (Elmer, J. S. et al. (34) and Gardiner, W. E. et al. (35)). Therefore, agro-infection of a susceptible plant could be accomplished with a virion containing a RPVNA based on the nucleotide sequence of any of the above viruses.

A still further feature of the invention is a process for the production of a specified polypeptide or protein product such as, but not limited to, enzymes, complex biomolecules, a ribozyme, or polypeptide or protein products resulting from anti-sense RNA. Such products include, but not limited to: IL-1, IL-2, IL-3, . . . IL-12, etc.; EPO; CSF including G-CSF, GM-CSF, hPG-CSF, M-CSF, etc; Factor VIII; Factor IX; tPA; hGH; receptors and receptor antagonists; antibodies; neuro-polypeptides; melanin; insulin; vaccines and the like.

The non-native nucleic acid of the RPVNA comprises the transcribable sequence which leads to the production of the desired product. This process involves the infection of the appropriate plant host with a recombinant virus or recombinant plant viral nucleic acid such as those described above, the growth of the infected host to produce the desired product, and the isolation of the desired product, if necessary. The growth of the infected host is in accordance with conventional techniques, as is the isolation of the resultant product.

For example, a coding sequence for a protein such as neomycin phosphotransferase (NPTII) α-trichosanthin, rice α-amylase, human α-hemoglobin or human β-hemoglobin, is inserted adjacent the promoter of the TMV coat protein coding sequence, which has been deleted. In another example, a tyrosinase coding sequence such as isolated from *Streptomyces antibioticus* is inserted adjacent the same promoter of TMV, oat mosaic virus (OMV) or rice necrosis virus (RNV). Recombinant virus can be prepared as described above, using the resulting recombinant plant viral nucleic acid. Tobacco or germinating barley is infected with the recombinant virus or recombinant plant viral nucleic acid. The viral nucleic acid self-replicates in the plant tissue to produce the enzymes amylase or tyrosinase. The activity of this tyrosinase leads to the production of melanin. See, for example, Huber, M. et al. (36).

In a further example, a cyclodextrin glucanotransferase coding sequence, such as isolated from Bacillus sp. No. 17-1 (see U.S. Pat. No. 4,135,977) is inserted adjacent the promoter of the viral coat protein of a nucleotide sequence derived from OMV, RNV, PVY or PVX in which the coat protein coding sequence has been removed, and which then contains a non-native promoter and coat protein gene. Corn or potato is infected with the appropriate recombinant virus or recombinant plant viral nucleic acid to produce the enzyme cyclodextrin glucotransferase. The activity of this enzyme leads to the production of cyclodextrin, which is useful as a flavorant or for drug delivery.

In some plants, the production of anti-sense RNA as a product can be useful to prevent the expression of certain phenotypic traits. Particularly, some plants produce substances which are abused as drugs (e.g., cocaine is derived from the coca plant, and tetrahydrocannabinol (THC) is the active substance of abuse derived from cannabis or marijuana plants). An anti-sense RNA complementary to the plant RNA necessary for the production of an abusable substance would prevent the production of the substance. This could prove to be an effective tool in reducing the supply of illegal drugs.

A still further feature of the invention is a process for the production of an enzyme suitable for the stereospecific catalysis of an organic compound. The non-native nucleic acid comprises the transcribable sequence which leads to the production of the desired product. This process involves the infection of the appropriate host with a recombinant virus or recombinant plant viral nucleic acid such as those described above, the growth of the infected host to produce the desired product and the isolation of the desired product. The growth of the infected host is in accordance with conventional techniques, as is the isolation of the resultant product. The stereospecific enzyme is then utilized to catalyze the desired reaction. One use of stereospecific enzymes is in the separation of racemate mixtures.

In one example, a suitable esterase or lipase coding sequence such as isolated from an appropriate microorganism is inserted adjacent the promoter of the viral coat protein of a nucleotide sequence derived from TMV, oat mosaic virus (OMV) or rice necrosis virus (RNV) in which the coat protein coding sequence has been removed and which then contains a non-native promoter and coat protein gene. Tobacco or germinating barley is infected with the recombinant virus or recombinant plant viral nucleic acid to produce the esterase or lipase enzyme. This enzyme is isolated and used in the stereospecific preparation of a compound such as naproxen, as described in EP-A 0233656 or EP-A 0227078.

An esterase coding sequence is isolated from the appropriate microorganism, such as *Bacillus subtilis, Bacillus licheniformis* (a sample of this species is deposited with the American Type Culture Collection, Rockville, Md. (ATCC) under Accession No. 11945), *Pseudomonas fluorescens, Pseudomonas putida* (a sample of this species is deposited with the Institute for Fermentation (IFO), Osaka, Japan, under Accession No. 12996), *Pseudomonas riboflavina* (a sample of this species is deposited with IFO under Accession No. 13584), *Pseudomonas ovalis* (a sample of this species is deposited with the Institute of Applied Microbiology (SAM), University of Tokyo, Japan, under Accession No. 1049), *Pseudomonas aeruainosa* (IFO 13130), *Mucor angulimacrosporus* (SAM 6149), *Arthrobacter paraffineus* (ATCC 21218), Strain is III-25 (CBS 666.86), Strain LK 3-4 (CBS 667.86), Strain Sp 4 (CBS 668.86), Strain Thai III 18-1 (CBS 669.86), and Strain Thai VI 12 (CBS 670. 86).

Advantageously, cultures of species *Bacillus subtilis* include cultures of species Bacillus species Thai 1-8 (CBS 679.85), species Bacillus species In IV-8 (CBS 680.85), species Bacillus species Nap 10-M (CBS 805.85), species Bacillus species Sp 111-4 (CBS 806.85), *Bacillus subtilis* 1-85 (Yuki, S. et al., Japan J. Gen. 42:251 (1967)), *Bacillus subtilis* 1-85/pNAPT-7 (CBS 673.86), *Bacillus subtilis* 1A-40/pNAPT-8 (CBS 674.86), and *Bacillus subtilis* 1A-40/pNAPT-7 (CBS 675. 86). Advantageously, cultures of *Pseudomonas fluorescens* include a culture of species Pseudomonas species Kpr 1-6 (CBS 807.85), and *Pseudomonas fluorescens* species (IFO 3081).

A lipase coding sequence is isolated from the appropriate microorganism such as the genera Candida, Rhizopus, Mucor, Aspergilus, Penicillium, Pseudomonas, Chromobacterium, and Geotrichium. Particularly preferred is the lipase of *Candida cylindracea* (Qu-Ming et al., Tetrahedron Letts. 27, 7 (1986)).

A fusion protein can be formed by incorporation of the non-native nucleic acid into a structural gene of the viral nucleic acid, e.g., the coat protein gene. The regulation sites on the viral structural gene remain functional. Thus, protein synthesis can occur in the usual way, from the starting codon for methionine to the stop codon on the foreign gene, to produce the fusion protein. The fusion protein contains at the amino terminal end a part or all of the viral structural protein, and contains at the carboxy terminal end the desired material, e.g., a stereospecific enzyme. For its subsequent use, the stereospecific enzyme must first be processed by a specific cleavage from this fusion protein and then further purified. A reaction with cyanogen bromide leads to a cleavage of the peptide sequence at the carboxy end of methionine residues (5.0. Needleman, "Protein Sequence Determination", Springer Publishers, 1970, N.Y.). Accordingly, it is necessary for this purpose that the second sequence contain an additional codon for methionine, whereby a methionine residue is disposed between the N-terminal native protein sequence and the C-terminal foreign protein of the fusion protein. However, this method fails if other methionine residues are present in the desired protein. Additionally, the cleavage with cyanogen bromide has the disadvantage of evoking secondary reactions at various other amino acids.

Alternatively, an oligonucleotide segment, referred to as a "linker," may be placed between the second sequence and the viral sequence. The linker codes for an amino acid sequence of the extended specific cleavage site of a proteolytic enzyme as well as a specific cleavage site (see, for example, U.S. Pat. Nos. 4,769,326 and 4,543,329). The use of linkers in the fusion protein at the amino terminal end of the non-native protein avoids the secondary reactions inherent in cyanogen bromide cleavage by a selective enzymatic hydrolysis. An example of such a linker is a tetrapeptide of the general formula Pro-Xaa-Gly-Pro(SEQ ID NO: 1) (aminoterminal end of non-native protein), wherein Xaa is any desired amino acid. The overall cleavage is effected by first selectively cleaving the xaa-Gly bond with a collagenase (E.C. 3.4.24.3., Clostridiopeptidase A) then removing the glycine residue with an aminoacyl-proline aminopeptidase (aminopeptidase-P, E.C. 3.4.11.9.) and removing the proline residue with a proline amino peptidase (E.C. 3.4.11.5). In the alternative, the aminopeptidase enzyme can be replaced by postproline dipeptidylaminopeptidase. Other linkers and appropriate enzymes are set forth in U.S. Pat. No. 4,769,326.

A still further feature of the invention is a process for the induction of male sterility in plant. Male sterility can be induced by several mechanisms, including, but not limited to, an anti-sense RNA mechanism, a ribozyme mechanism, or a protein mechanism which may induce male sterility or self-incompatibility or interfere with normal gametophytic development. The second nucleotide sequence of the chimeric nucleotide sequence comprises the transcribable sequence which leads to the induction of male sterility. This process involves the infection of the appropriate plant with a virus, such as those described above, and the growth of the infected plant to produce the desired male sterility. The growth of the infected plant is in accordance with conventional techniques.

Male sterility can be induced in plants by many mechanisms including, but not limited to (a) absence of pollen formation, (b) formation of infertile and/or non-functional pollen, (c) self-incompatibility, (d) inhibition of self-compatibility, (e) perturbation of mitochondrial function(s), (f) alteration of the production of a hormone or other biomolecule to interfere with normal gametophytic development, or (g) inhibition of a developmental gene necessary for normal male gametophytic tissue. These mechanisms may be accomplished by using anti-sense RNA, ribozymes, genes or protein products. The recombinant plant viral nucleic acids of the present invention contain one or more nucleotide sequences which function to induce male sterility in plants. To accomplish this function, the recombinant plant viral nucleic acids may contain a nucleotide sequence, a single gene or a series of genes.

Male sterility traits could be formed by isolating a nuclear-encoded male sterility gene. Many of these genes are known to be single genes. For example, Tanksley et al. (37) placed ms-10 in CIS with a rare allele of the tightly linked enzyme-coding gene Prx-2.

The Prx-2 allele is codominant, allowing selection for heterozygous plants carrying the recessive ms-10 allele in backcross populations and eliminating the need for progeny testing during transfer of the gene into parents for hybrid production. A male-sterile anthocyaninless plant (ms-10 aa/ms-10aa) was crossed to a heterozygous, fertile plant in which a rare peroxidase allele was in cis with the recessive male-sterile allele (ms-10 Prx-2'/+Prx-2+). Male sterile plants were selected from the progeny (ms-10 Prx-2'/ms-10aa). Once the male-sterile gene has been transferred into a prospective parental line, sterile plants can be selected at the seedling stage either from backcross or $F_2$ seed lots.

In pearl millet, recessive male sterile genes were found in vg 272 and IP 482. Male sterility in pearl millet line Vg 272 and in IP 482 is essentially controlled by a single recessive gene. Male sterility in Vg 272 is due to a recessive gene, ms, which has no effect on meiosis in pollen mother cells, but acts after separation of microspores from tetrads but before onset of the first mitotic division.

Dewey et al. (39) isolated and characterized a 3547 bp fragment from male sterile (cms-T) maize mitochondria, designated TURF 243. TURF 243 contains two long open reading frames that could encode polypeptides of 12,961 Mr and 24,675 Mr. TURF 243 transcripts appeared to be uniquely altered in cms-T plants restored to fertility by the nuclear restorer genes Rf1 and Rf2. A fragment of maize mtDNA from T cytoplasm was characterized by nucleotide sequence analysis. To obtain isolation of nucleic acids, mitochondrial RNA (mtRNA), and mtDNA were prepared from six- to seven-day-old dark grown seedlings of Zea Mays L. by conventional techniques.

Another means by which male sterile traits could be formed is by the isolation of a male sterility gene from a virus. There are several viruses or virus-like particles that induce male sterility in plants. Recent work suggests that viroid-like agents in male sterile beets may occur. (40). Cytoplasmic male sterility may be conditioned by a discrete particle such as a plasmid or an inclusion. Viruses are not seed transmitted with the regularity of cytosterile systems. Viroids can be transmitted through pollen. Transfer of a factor of some kind across a graft union has been demonstrated in petunia, beet, sunflower, and alfalfa. There is no direct effect on the fertility of the scion, but selfs or crosses by a maintainer on the grafted scion produced male sterile plants in the next generation. Cms beets grown at 36° C. for 6 weeks, then at 25° C., produced fertile plants from new shoots possibly due to elimination of "cytoplasmic spherical bodies", but progenies from the plants reverted to sterility after three generations at normal growing conditions. Cytoplasmic male sterility in the broad bean plant (*Vicia fabal*) was found to be caused by the presence of virus or virus-like particles. Possibly a case similar to a cms-system occurs in garlic. Pollen degeneration typical of sporophytic cms plants was found, but electron microscope studies showed richettsia-like inclusions in the anthers, which could be eliminated with antibiotics, causing the pollen to become fertile (41).

Male sterile traits could be formed by a third method of introducing an altered protein, using a transit peptide sequence so that it will be transported into the mitochondria, and perturbing the mitochondrial functions. This protein could work to overwhelm normal mitochondrial function or reduce a metabolite required in a vital pathway. It is widely believed that slight perturbations in the mitochondria will lead to male sterility. Remy et al. (42) conducted a two dimensional analysis of chloroplast proteins from normal and cytoplasmic male-sterile *B. napus* lines. Chloroplast and mitochondrial DNAs of N and cms lines of *B. napus* were characterized and compared using restriction enzyme analysis. Identical restriction patterns were found for chloroplastic DNAs from the cms *B. napus* lines and the cms lines of the Japanese radish used to transfer the cms trait into *B. napus*. In Remy's study, chloroplast proteins from stroma and thylakoids of N and cms lines of *B. napus* were characterized and compared using a 2-D polyacrylamide gel separation. It was shown that (1) stromal compartments of the two lines were very similar, and (2) the lines could be distinguished by the spots corresponding to the $\beta$ subunits of coupling factor CP, from the ATPase complex.

A fourth method for inducing male sterility in plants is by inducing or inhibiting a hormone that will alter normal gametophytic development—for example, inhibiting the production of gibberellic acid prior to or at the flowering stage to disturb pollen formation, or modifying production of ethylene prior to or at the flowering stage to alter flower formation and/or sex expression.

A fifth method for inducing male sterility in plants is by inhibiting a developmental gene required for the normal male gametophytic tissue, for example, using anti-sense RNA that is complementary to the developmental signal RNA or mRNA. Padmaja et al. (43) discusses cytogenetical investigations on a spontaneous male-sterile mutant isolated from the Petunia inbred lines. Male sterility was found to be associated with atypical behavior of tapetum, characterized by prolonged nuclear divisions and untimely degeneration as a result of conversion from glandular to periplasmodial type.

A sixth method for inducing male sterility in plants is by isolating a self-incompatibility gene and using the gene in the vector of the present invention. Self-incompatibility (S) gene systems that encourage out-breeding are present in more than 50% of the angiosperm plant families (44). Multiple S gene systems are known in some species. In several systems, abundant style glycoproteins (S glycoproteins) have been identified. These glycoproteins are polymorphic and can be correlated with identified S alleles. S genes, corresponding to the style glycoproteins of *N. alaba* and *B. oleraceae* have been cloned and sequenced. Amino acid substitutions and deletions/insertions, although present throughout the sequences, tend to be clustered in regions of hypervariability that are likely to encode allelic specificity.

A seventh method for inducing male sterility in plants is by blocking self incompatibility, by the engineering of a protein that will bind and inactivate the compatibility site or by turning off self-compatibility, by the engineering of an anti-sense RNA that will bind with the mRNA to a self-compatibility protein.

Specific effects resulting in male sterility can range from the early stages of sporogenous cell formation right through to a condition in which anthers containing viable pollen do not dehisce. Some or all of the developmental stages within this range may be affected. Some of the more obvious specific effects include, the following examples:

1) Meiosis is disrupted, leading to degeneration of the pollen mother cells or early microspores in which case pollen aborts and anther development is arrested at an early stage.

2) Exine formation is disrupted and microspores are thin-walled, perhaps distorted in shape, and nonviable. Anthers are generally more developed than the exines, but still not normal.

3) Microspore vacuole abnormalities, decreased starch deposition and tapetum persistence are evident. Pollen is nonviable and anthers are still not normal.

4) Pollen is present and viable, and anthers appear normal but either do not dehisce or show much delayed dehiscence.

5) Self incompatibility mechanisms disrupt or prevent enzymatic digestion of the style by the pollen grain.

Male sterility in plants may be induced by the mechanisms listed above at any stage prior to pollen shed. The male sterility mechanism selected may be applied to plants in the field (or in the greenhouse) at any time after seedling emergence and before pollen shed. The exact time of application will depend on the male sterility mechanism used and the optimum effectiveness in producing male sterile plants.

EXAMPLES

In the following examples, enzyme reactions were conducted in accordance with manufacturers recommended procedures, unless otherwise indicated. Standard techniques, such as those described in *Molecular Cloning* (7), *Meth. in Enzymol.* (9) and *DNA Cloning* (8), were utilized for vector constructions and transformation unless otherwise specified.

COMPARATIVE EXAMPLES

The following comparative examples demonstrate either the instability of prior art recombinant viral nucleic acid during systemic infection of host plants or the inability to systemically infect plants and to efficiently produce the product of the inserted nonnative gene.

Comparative Example 1

Recombinant plant viral nucleic acid was prepared by inserting the chloramphenical acetyltransferase (CAT) gene which had been fused behind a TMV subgenomic RNA promoter between the 30K and coat protein genes of TMV. pTMV-CAT-CP was prepared as described by Dawson, W. O. et al. (11). Briefly, pTMV-CAT-CP was constructed by cutting pTMV204, a full-genomic cDNA clone of TMV strain U1 (4) with NcoI (nt. 5460), blunting with Klenow fragment of DNA polymerase I, adding PstI linkers (CCTGCACG from Boehringer-Mannheim Biochemicals), excising with PstI and NsiI (nt. 6207), and ligating this 747-bp fragment into the NsiI site (nt. 6207) of pTMV-S3-CAT-28, a modified TMV with the CAT ORF substituted for the coat protein ORF (45). TMV nucleotide numbering is that of Goelet et al. (46). Correct ligation and orientation of each construct were checked by restriction mapping and sequencing.

Inoculations. In vitro transcription of plasmid DNA constructs and inoculation procedures were as described previously (3). Virus was propagated systemically in Xanthi tobacco (*Nicotiana tabacum* L.) and *Nicotiana svlvestris*: Xanthi-nc tobacco was used as a local lesion host. Plants were grown in a greenhouse prior to inoculations and then subsequently maintained in plant growth chambers at 25° with a 16-hour photoperiod of approximately 2000 lx.

CAT Assays. Amounts of CAT activity were assayed essentially by the procedures described (47), 200 mg of leaf tissue were macerated in assay buffer followed by addition of 0.5 mM acetyl CoA and 0.1 μCi [$^{14}$C]-chloramphenicol, incubation for 45 minutes at 37°, extraction and resolution by thin-layer chromatography, and finally autoradiography.

RNA Analysis. Four days after inoculation, total RNA from infected leaves was extracted as described (47a). For blot hybridization analysis, RNA was electrophoresed in 1.2% agarose gels, transferred to nitrocellulose, and hybridized with nick-translated cDNA of TMV (nts. 5080-6395) in pUC119 or pCM1 (Pharmacia) which contains the CAT ORF. Total RNA from infected leaves also was analyzed by RNase protection assays for wild-type sequences essentially as described in Ausubel et al. (48). The 3' half (BamHI:nt. 3332-PstI:nt. 6401) of pTMV204 was cloned into pT7/T3-19 (from BRL). After EcoRI digestion (nt. 4254), $^{32}$P-labeled transcripts complementary to the 3' viral sequencs were produced with T7 RNA polymerase. An excess amount of the probe was hybridized to RNA samples, treated with 40 μg/ml RNase A (Sigma) and 300 U RNase T1 (BRL) extracted, denatured with DMSO and glyoxal, and electrophoresed in 1.2% agarose gels which were subsequently dried and exposed to Kodak X-ray film.

Construction of cDNA Clones of ProgenY Virus. RNA was extracted from purified virions and cDNA was prepared as previously described (4) Double-stranded cDNA was digested with BamHI (nt. 3332) and SacI (nt. 6142) and cloned into BamHI- and SacI-digested pUC19. Nucleotide sequencing of DNA was by the dideoxynucleotide chain terminating procedure (49).

Results. In vitro transcripts of pTMC-CAT-CP, which had the CAT cartridge inserted upstream of the coat protein gene, resulted in CAT-CP, a hybrid virus 7452 nucleotides in length and a gene order of 126K, 183K, 30K, CAT and coat protein. In vitro transcripts were used to inoculate leaves of *N. tabacum* L. varieties Xanthi and Xanthi-nc and *N. sylvestris*. Results were compared to those from plants infected with wild-type virus, TMV 204, or the free-RNA virus, S30CAT-28, that expresses CAT as a replacement for coat protein (45) CAT-CP replicated effectively and moved from cell to cell in inoculated leaves similarly to TMV 204. Necrotic lesions developed on Xanthi-nc tobacco at approximately the same time and were of the same size as those caused by TMV 204 and S3-CAT-2B. CAT-CP induced no symptoms in inoculated leaves of the systemic hosts, Xanthi tobacco and *N. sylvestris*, but produced mosaic symptoms in developing leaves similar to those produced by TMV 204. The concentration of virions in cells infected with CAT-CP, estimated by yields obtained after virion purification and by transmission electron microscopy of thin sections of inoculated leaves, appeared to be approximately equal to that from a TMV 204 infection.

CAT-CP is 7452 nucleotides long, compared to 6395 nucleotides for TMV 204, whih would result in CAT-CP virions 350 nm in length, compared to the 300 nm virions of wild-type TMV. Virus was purified from inoculated leaves of CAT-CP-infected plants and analyzed by transmission electron microscopy. Most of the virions from the CAT-CP infections were 350 nm in length. One problem in assessing the length of virions of TMV UI viewed by electron microscopy is that preparations normally contain fragmented and end-to-end aggregated virions in addition to individual genomic-length virions. To determine the proportion of 350- to 300-nm virions, distinct, individual virions of each size were counted. The ratio of 350/300 nm virions in leaves inoculated with CAT-CP was 191:21, compared to 12:253 from the wild-type infection. The 350-nm virions in wild-type TMV infection probably resulted from the end-to-end aggregation of fragmented virions, since TMV UI has a propensity to aggregate end-to-end and all length virions can be found. These data suggest that the extra gene of CAT-CP was maintained and encapsidated in these inoculated leaves.

CAT activity was detected in leaves inoculated with CAT-CP using in vitro RNA transcripts or the subsequent first or second passage local lesions. From more than one hundred samples assayed, a range of variation was found among different positive samples. Similar levels of CAT were found in CAT-CP-infected leaves as those infected with the coat protein-less mutant, S3-CAT-2 B. Only background amounts were detected in TMV 204-infected or healthy leaves.

The host range of CAT-CP was compared to that of wild-type TMV by inoculating a series of hosts known to support replication of TMV and by screening for CAT activity. CAT activity was detected in inoculated leaves of *Zinnia eleaans* Jacq., *Lunaria annua* L., *Beta vulaaris* L., *Calendula officinalis* L., and *Spinacia oleracea* L., which represent three plant families in addition to the Solanaceae. This indicated that this alteration of the TMV genome did not appear to alter the host range.

In order to determine whether CAT-CP produced an additional subgenomic RNA as a result of the inserted sequences, total RNA from infected leaves was extracted and compared to that of wild-type TMV by blot hybridization analysis, using a TMV or a CAT DNA probe. Xanthi tobacco leaves infected with CAT-CP previously passaged twice in xanthi-nc tobacco were chosen because they contained a population of CAT-CP and progeny virus with deletions to be compared to wild-type TMV. Two distinct genomic RNAs were detected. The largest hybridized to both TMV and CAT probes, whereas the smaller genomic RNA hybridized only to the TMV probe and comigrated with wild-type Tv genomic RNA. Three distinct, small RNAs were found in RNA from CAT-CP-infected leaves, compared to two from TMV 204-infected leaves. The smaller RNAs that comigrated with the subgenomic messages for the coat and 30K proteins of wild-type TMV hybridized only to the Tv-specific probe. A larger subgenomic RNA from CAT-CP-infected leaves hybridized to both the CAT and TMV probes. Assuming that as for the subgenomic mRNAs of wild-type TMV, this larger subgenomic RNA is 3' coterminal with the genomic RNA (50), these results are consistent with the extra CAT-CP mRNA predicted for expression of CAT. The putative CAT-CP subgenomic RNA for 30K protein, containing the 30K, CAT, and coat protein ORFs was not observed, possibly because bands in the region between 2.4 and 4.4 kb were obscured by viral RNAs adhering during electrophoresis to host rRNAs and were difficult to resolve (50, 51).

The amounts of CAT activity in upper, systemically infected leaves were variable and much lower than in inoculated leaves, and in many cases none was detected. Hybridizations with Tv and CAT probes demonstrated that the proportion of virus-retaining CAT sequences was quickly reduced to undetectable levels. The transition from CAT-CP to a population of virus with the inserted CAT ORF deleted occurred during systermic invasion of the plant and sometimes in inoculated leaves. In contrast, CAT sequences and CAT activity often were detected in leaves inoculated with virus that had been passaged through single lesions three or four times.

CAT-CP virions were examined from systemically infected Xanthi tobacco leaves approximately 30 days after inoculation. Quantification of virions from the uppermost leaves of the plants infected with CAT-CP produced a ratio of 350-/300-nm virions of 78:716. This was compared to a ratio of 191:21 in inoculated leaves, indicating that the major component of the population shifted to 300-nm virions during systemic infection. The deleted progeny virus recovered after continued replication of CAT-CP was identical in host range and symptomatology to wild-type TMV.

cDNA of the region that encompassed the CAT insertion (nts. 3332-6142) was cloned from the progeny CAT-CP virion RNA from systemically infected Xanthi leaves to sample the virus population. Characterization of nine cDNA clones by size and restriction mapping indicated that eight were identical with wild-type TMV.

One cDNA clone appeared to be the size predicted for the CAT-CP construct, but the restriction map varied from that predicted for CAT-CP. Five clones that were evaluated by size and restriction analysis as wild-type were sequenced through the region of the CAT insertion and also through a portion of the coat protein gene, and found to be identical to the parental wild-type virus. This suggested the inserted sequences could be excised, giving rise to wild-type TMV.

To corroborate this possible excision, samples of the total leaf RNA used in the blot hybridization analysis were analyzed by RNase protection assays using T7-produced minus-strand RNA complementary to in-inoculated leaves. In contrast, CAT sequences and CAT activity often were detected in leaves inoculated with virus that had been passaged through single lesions three or four times.

CAT-CP virions were examined from systemically infected Xanthi tobacco leaves approximately 30 days after inoculation. Quantification of virions from the uppermost leaves of the plants infected with CAT-CP produced a ratio of 350-/300-nm virions of 78:716. This was compared to a ratio of 191:21 in inoculated leaves, indicating that the major component of the population shifted to 300-nm virions during systemic infection. The deleted progeny virus recovered after continued replication of CAT-CP was identical in host range and symptomatology to wild-type TMV.

cDNA of the region that encompassed the CAT insertion (nts. 3332-6142) was cloned from the progeny CAT-CP virion RNA from systemically infected Xanthi leaves to sample the virus population. Characterization of nine cDNA clones by size and restriction mapping indicated that eight were identical with wild-type TMV.

One cDNA clone appeared to be the size predicted for the CAT-CP construct, but the restriction map varied from that predicted for CAT-CP. Five clones that were evaluated by size and restriction analysis as wild-type were sequenced through the region of the CAT insertion and also through a portion of the coat protein gene, and found to be identical to the parental wild-type virus. This suggested the inserted sequences could be excised, giving rise to wild-type TMV.

To corroborate this possible excision, samples of the total leaf RNA used in the blot hybridization analysis were analyzed by RNase protection assays using T7-produced minus-strand RNA complementary to nucleotides 4254-6395 of wild-type TMV. The presence of wild-type sequences in this region would result in a protected RNA of 2140 nucleotides. A band this size from the CAT-CP RNAs comigrated with a similar band produced suing wild-type RNA to protect the probe. These data confirmed that the inserted sequences of CAT-CP could be precisely deleted. Taking into consideration the presence of repeated sequences in CAT-CP RNA that allow the bulge loop in the hybrid between CAT-CP and the wild-type TMV probe RNA to occur over a range of positions within the repeats, the RNase protection of wild-type probe by CAT-CP RNA should produce sets of bands that would fall within two nucleotide size ranges, 683-935 and 1202-1458. The other two major bands seen are of these sizes, corroborating the presence of CAT-CP RNA in these samples.

The loss of the inserted sequences of CAT-CP appeared to be due to two sequential processes. First was the loss of inserted sequences in individual molecules, as shown by the sequence analysis of cDNA clones of progeny virus. Since the deletion occurred between repeated sequences, it is possible that this occurred by homologous recombination as described for other plus-sense RNA viruses (52-54) The second process resulted in a selected shift in the virus population. The RNase protection assays, in which the virus population was sampled, demonstrated that both CAT-CP and wild-type virus could be components of the population in inoculated leaves. The lack of CAT-CP in systemically infected leaves was probably due to a shift in the virus population, possibly because the original hybrid could not effectively compete with the deleted progeny wild-type virus in terms of replication and systemic movement.

Comparative Example 2

A recombinant plant viral nucleic acid was prepared by inserting the CAT gene which had been fused behind a TMV subgenomic RNA promoter between the coat protein gene and the nontranslated 3' region of TMV. pTMV-CP-CAT was prepared as described by Dawson et al. (II) Briefly, pTMV-CP-CAT was constructed by cutting pTMV-S3-CAT-28 with HindIII (nt. 5081), blunting with Klenow fragment of DNA polymerase I, adding PstI and NsiI (nt. 6207), and ligating this 1434-bp fragment in the NsiI site (nt. 6207) of pTMV204. Correct ligation and orientation of each construct were checked by restriction mapping and sequencing.

Plant inoculations, CAT assays, RNA analysis and construction of cDNA clones of progeny were performed as described in Comparative Example I. pTMV-CP-CAT, the larger hybrid virus construct, contained a 628-nucleotide repeat of that portion of the 30K gene containing the coat protein subgenomic promoter and the origin of assembly. This construct should produce a virus, CP-CAT, 7822 nt long with a gene order of 126K, 183K, 30K, coat protein, and CAT. CP-CAT replicated poorly. It produced necrotic lesions in Xanthi-nc that were small, approximately one-half the diameter of wild-type virus lesions, and their appearance was delayed by two days. Transmissibility of CP-CAT from these lesions was at a level approximately one-hundredth that of CAT-CP or wild-type TMV. No systemic symptoms appeared in Xanthi or *N. svlvestris* plants and the virus infection was transferrable only from inoculated leaves. Low but reproducible levels of CAT activity were found in CP-CAT-infected leaves. Since the replication of this chimeric virus was so impaired, characterization did not proceed any further.

In contrast to CAT-CP, when CP-CAT was allowed to replicate for extended periods in the systemic hosts, no wild-type-like virus symptoms ever were observed in upper leaves of plants and virus was never recovered from them, suggesting that this hybrid virus did not delete the inserted sequences in a manner to create a wild-type-like virus.

Comparative Example 3

A full-length DNA copy of the TMV genome is prepared and inserted into the PSTI site of pBR322 as described by Dawson, W. O. et al. (t). The viral coat protein gene is located at position 5711 of the TMV genome adjacent the 30k protein gene. The vector containing the DNA copy of the TMV genome is digested with the appropriate restriction enzymes and exonucleases to delete the coat protein coding sequence. For example, the coat protein coding sequence removed by partial digestion with ClaI and NsiI, followed by religation to reattach teh 3'-tail of the virus. Alternatively, the vector is cut at the 3' end of the viral nucleic acid. The viral DNA is removed by digestion with Bal31 or exonuclease III up through the start codon of the coat protein coding sequence. A synthetic DNA sequence containing the sequence of the viral 3'-tail is then ligated to the remaining 5'-end. The deletion of the coding sequence for the viral coat protein is confirmed by isolating TMV RNA and using it to infect tobacco plants. The isolated TMV RNA is found to be non-infective under natural conditions.

The 314-bp Sau3A fragment (NH$_2$ terminus of the Tn5 NPTII gene) from pNEO was filled in with Klenow polymerase and ligated to SalI (pd[GGTCGACC]) linkers. It was then digested with SalI and PstI and inserted into PstI/SalI-digested pUC128 (55) to give pNU10. The pNEO plasmid was digested with AsuII, filled in with Klenow polymerase and ligated to XhoI linkers (pd[CCTCGAGG]) to give pNX1. The pNX1 was digested with XhoI, filled in with Klenow polymerase, digested with PstI and ligated into PstI/SmaI-digested pNU10 to give pNU116.

The XhoI/SalI fragment from pNU116 (NPTII sequences) is ligated adjacent the coat protein promoter. The resultant RFVNA containing the NPTII gene insert was applied to twelve *Nicotiana tabacum* (cv. Xanthi-NC), a cultivar that has been backcrossed to contain the N gene for TMV resistance and to twelve *N. tabacum* (cv. Xanthi), a cultivar that does not contain the N gene. In both tobacco cultivars, no systemic spread was observed in any inoculated plant. The *N. tabacum* (cv. Xanthi NC) showed the characteristic flecking spots on the inoculate leaf indicating resistance to the virus. The *N. tabacum* (cv. Xanthi) exhibited no flecking or systemic symptoms.

Comparative Example 4

A recombinant plant viral nucleic acid containing the NFTII coding sequence was prepared as described in Comparative Examples 1 and 3. The NFTII and coat protein coding sequences were each adjacent an "O" coat protein promoter. The presence of the coat protein gene should render the vector capable of being systemically spread.

The resultant RFVNA containing the NPTII-inserted gene was inoculated on twelve *N. tabacum* (cv. Xanthi NC) and twelve *N. tabacum* (cv. Xanthi NC) showed the flecking in each of the twelve plants, as with Comparative Example 1. The *N. tabacum* (cv. Xanthi) plants showed systemic spread of the vector in all twelve plants.

Leaf discs from *N. tabacum* (cv. Xanthi) leaves were cultured on media containing kanamycin. None of the tissue survived in culture, indicating a loss or disfunction of the NFTII gene. Subsequent electron photomicroscopy of the present vector containing the NFTII gene recovered from the leaves of treated *N. tabacum* (cv. Xanthi) plants showed that the present vector had lost a section of the vector corresponding to the NPTII gene, indicating a breakage and recombination of the vector.

EXAMPLES OF THE PREFERRED EMBODIMENTS

The following examples further illustrate the present invention. These examples are intended merely to be illustrative of the present invention and are not to be construed as being limited.

Example 1

Construction of Bacterial Plasmids. Numbers in parentheses refer to the TMV-U1 sequence (46). DNA manipulations were performed essentially as described in (48). All plasmids were propagated in *E. coli* strain JM109 except for pTBN62 (DH5α; Gibco BRL; and H8101).

pTKU1 (Fia. 1). The 7.3 kb pTMV204 (4) PstI fragment (TMV-U1 genome and λ phage promoter from pPM1 (3) was subcloned into pUC19 to give pTP5. pTMV204 ApaI fragment (5455-6389) was ligated to oligonucleotides pd[CAGGTACCC] and d[GGGTACCTGGGCC], (SEQ ID No: 2), digested with KpnI (underlined within nucleotide sequence) and NcoI (5459) and ligated into NcoI/KpnI digested pTP5 to produce pTPK10. pTKU1 was constructed by subcloning the 7.3 kb PstI/KpnI fragment from pTPK10 into PstI/KpnI-digested pUC118. pTKU1 contained a DNA copy of the entire TMV-VI genome downstream of the λ phage promoter from pPM1. KpnI digestion and in vitro transcription of pTKUI gave infectious TMV RNA. pTKUI was constructed because PstI sites in the odotoglossum ring spot virus (ORSV, sometimes referred to as TMV-O) coat protein, DHFR and NFTII ORFs prohibited the use of this restriction enzyme (employed to linearize pTMV204; 4) to digest plasmid DNA of the hybrid constructs and produce infectious in vitro transcripts.

pT82 (FIG. 1). pTMVS3-28 (45) was a derivative of pTMV204 in which the coat protein initiation codon was mutated to ACG and a XhoI site replaced the entire coat protein coding sequence. The 1.9 kb NcoI/SalI fragment (5459-SalI site in p8R322) from pTMVS3-28 was ligated into NcoI/SalI-digested pNEO (56) to give pNS283. pBabsI was a 2.4 kb EcoRI cDNA clone from ORSV virion RNA with nucleotide, ORF and amino acid sequence similarities to TMV-UI (nts 4254-6370). A 680 bp pBabsl HincII/EarI (Klenow polymerase infilled) fragment (containing the ORSV coat protein ORF and 203 bases upstream of its AUG) was ligated into the NstI site (6202; blunt-ended with T4 DNA polymerase) of pNS283 to produce pB31. The NcoI/-SalI fragment from p831 was then ligated into the NcoI/SalI-digested pTMV204 (replacing the corresponding wild-type fragment 5459-SalI site in pBR322) to give pTB281. pTB2 was constructed by ligating the BamHI/SplI fragment from pTB281 into BamHI/SplI-digested pTKUI (replacing the corresponding wild-type fragment 3332-6245).

pNC4X (57). pNC4X consisted of the R67 DHFR gene cloned into pUC8X. The plasmid contained a XhoI site eight bases upstream of the initiation codon for the DHFR gene. In addition, the stop codon and five bases of carboxy-terminal DHFR sequence were deleted and replaced by a SalI site.

pNU116. A 315 bp pNEO Sau3S (Klenow polymerase infilled) fragment ($NH_2$ terminus of Tn5 NPTII gene) was ligated to SalI (pd[GGTCGACC]) linkers, SalI/FstI digested, and inserted into FstI/SalI-digested pUC128 (55) to give pNU10. pNEO was digested with AsuII, infilled with Klenow polymerase and ligated to XhoI linkers (pd[CCTCGAGG]) to generate pNX1. pNUII6 was constructed by digesting pNX1 with XhoI, infilling with Klenow polymerase, digesting with PstI and ligating the resulting 632 bp fragment (COOH terminus of the Tn5 NPTII gene) into PstI/SmaI-digested pNU10. This manipulation of the NFTII gene removed an additional ATG codon 16 bases upstream of the initiation codon, the presence of which decreased NFTII activity in transformed plant cells (58).

pTBD4 and pTBN62 (Fia. 1). XhoI/SalI fragments from pNC4X (DHFR sequence) and pNU116 (NPTII sequence) respectively were ligated into the XhoI site of pT82 in the same sense as the TMV coding sequences.

In Vitro Transcription and Inoculation of Plants. Plants grown as in (45) were inoculated with in vitro transcripts TB2 (nt. 6602), T8D4 (nt. 6840) and TBN62 (nt. 7434) from KpnI digested pTBD2, pTBD4 and pTBN62, respectively. The in vitro transcription method was as previously described.

Analysis of Progeny Virion RNA. Virus purification was essentially as described by Gooding and Hebert (59) with one precipitation with polyethylene glycol (8% PEG, 0.1M NaCl; 0° C. 1 hr) and one ultracentrifugation (151,000-235,000×g; 90 min). Virion RNA was extracted by digesting 1 mg virus with 0.2 μg Froteinase K in 10 mM Tris HCl, pH 7.5 1 mM EDTA, 0.1% SDS at 37° C. for 1 hr, followed by phenol/chloroform extractions. RNA samples were DMSO-denatured, glyoxalated, electrophoresed in 1% agarose gels and transferred to nitrocellulose (pore size 0.45 μm; Schleicher and Schull; 48). The transfers were probed with [$\alpha-^{35}S$]-dATP (New England Nuclear) labelled (50) restriction fragments. RNase protection assays were as described in (48). TBD4-38 and pTBN62-38 contained BamHI/KpnI fragments (nts. 3332-6396) from pTBD4 and pTBN62, respectively, cloned into BamHI/KpnI-digested pBluescript SKI$^-$ (Stratagene).

Immunological Detection of NPTII. Sample preparation and Western analysis were as described previously (45). Leaf samples were ground in liquid $N_2$ and extraction buffer (10% glycerol, 62.5 mM Tris HCl pH 7, 5% mercaptoethanol, 5 mM phenylmethylsulfonyl fluoride). Equivalent protein concentrations were determined and absolute concentrations estimated by Bradford assey (Strategene; 61), with bovine serum albumin as standard. Western transfers were probed with antiserum to NPTII (1:500; 5 Prime, 3 Prime, Inc.) and then with alkaline phosphatase-conjugated goad anti-rabbit IgG (1:1000).

NFIII Activity Assays. NPTII activity was detected by its phosphorylation of neomycin sulphate. Enzyme assays were as described in (62) except the extraction buffer was as described above and dilution series of purified NPTII (5 Prime, 3 Prime, Inc.) in healthy tissue were included.

Leaf Disc Assays to Screen for Resistance to Kanamycin Sulphate. NPTII confers resistance to the aminoglycoside kanamycin (56). Young systemic leaves 12 days post-inoculation were surface-sterilized and washed in approximately 0.01% Tween 20 (5 min), 0.25% sodium hypochlorite (2 min), 70% ethanol (30 sec), distilled water (4×10 sec). Leaf discs were cut from a leaf in pairs; one was placed on Murashige and Skoog (MS) medium alone and the other on kanamycin sulphate-supplemented MS medium. Plates were incubated at 32° C. with a photoperiod of 16 hours. Leaf discs were transferred to freshly prepared medium every seven days.

Mechanical inoculation of *N. benthamiana* plants with in vitro transcripts derived from DNA constructs pTB2, pTBD4 and pTBN62, respectively, resulted in symptomatic infection with virus of typical TMV shape and yield (1.5-5.8 mg virus/g tissue). Symptoms were less severe compared to TMV-UI-infected plants and consisted of plant stunting with mild chlorosis and distortion of systemic leaves. The sizes of virion RNA from systemically infected tissue of plants inoculated with TB2, TBD4 and TBN62, respectively, were consistent with predicted lengths of RNA transcribed in vitro from the respective plasmids. These RNA species contained TMV sequences plus their respective bacterial gene inserts. Probes complementary to the manipulated portion of the respective genomes were protected in RNase protection assays by progeny TBD4 and TBN62 viral RNAs. This indicated that the precise and rapid deletion of inserted sequences which had been a problem with previous constructs (11) did not occur with TBD4 or TBN62. It was hypothesized that with the prevously reported constructs, foreign inserts were deleted due to recomb ination between repeated subgenomic promoter sequences (11) With TBD4 and TBN62, such repeated sequences were reduced by employing heterologous subgenomic mRNA promoters. Additional bands that were seen and were smaller than the probe and smaller than the full-length viral RNA might represent alterations within a portion of the TBN62 population, although in this case the relative proportion of full-length and additional smaller bands was unchanged following a subsequent passage.

The sequence stability of TBD4 and TBN62 virion RNA was examined in serial passages through *N. benthamiana*. Plants were inoculated with two and four independent in vitro transcript ion reactions from pTBD4 and pTBN62, respectively, and systemically infected leaf tissue was serially passaged every 11-12 days. After 48 days of systemic infection, full-length virion RNA of TBD4 including the DHFR sequences was still detected by Northern transfer hybridization, and still protected probes complementary to the manipulated portion of the genome in RNase protection assays. Five clonal populations of virion RNA were derived from TBD4-infected plants propagated for 170 days (one series involving 10 passages) by isolation of local lesions on *N. tabacum* Xanthi-nc. The concensus DHFR sequence for three of the populations corresponded with the published DHFR sequence except for a translationally silent third base change (U→C) at nucleotide 72 of the coding sequence. The nucleotide change at position 72 of the DHFR coding sequence was not evident in progeny RNA from TBD4 infected plants propagated for 48 days. Virion RNA from plants serially infected with TBN62 was less stable with different portions of the NPTII sequence being deleted in each of the independent series of passages The time of loss of these sequences varied between after the first passage (12-24 days) and the third passage (36→47 days). The reason for the occurrence of deletions in the NPTII sequence of TBN62 is not known. However, on the basis of the stability of the DHFR sequences in TBD4, such instability of inserted foreign sequences would not seem to be an intrinsic feature of the expression vector TB2. In contrast, such deletions might be dictated by the nucleotide composition of the inserted foreign sequences themselves. Similar instabilities among DNA plant virus vectors have been seen.

A commercial source of antiserum and sensitive enzymatic assays for the extensively used selectable marker NPTII (62) allowed further analysis of tissue infected with TBN62. Western blot analysis, enzyme activity, and leaf disc assays demonstrated the presence of functional NPTII enzyme and its phenotypic expression in plant tissue systemically infected with TBN62 but not in TB2-infected or healthy plants. NPTII protein and enzyme activity was even detected in some TBN62-infected plants propagated for 36 days.

It was evident that the levels of extractable NPTII protein were considerably lower than coat protein, the most highly expressed TMV protein. Such low levels could be a reflection of the relative stabilities or partitioning of the respective proteins in plant cells, or might be due to one or more aspects of the vector or foreign gene sequences affecting the synthesis of subgenomic mRNA or post-transcriptional expression of the reporter gene. The relatively high yield of virus from plants infected with the vector constructs would seem to preclude a dramatic reduction in the efficiency of virus replication. However, one possibility for low expression might be the position of the reporter gene relative to the 3' terminus of the genome. The amount of the 30 kDa protein produced by different mutants of TMV has been shown to be inversely proportional to the distance the 30 kDa protein ORF was from the 3' terminus of the genome. This relationship was consistent with the observations of French and Ahlquist (63), i.e., that the level of subgenomic RNA from brome mosaic virus RNA 3 was progressively greater the closer the promoter was inserted to the 3' terminus.

Example 2

Although the RPM of Example 1 is capable of systemic spread in *N. benthaniana*, it is incapable of systemic spread in *N. tabacum*. This example describes the synthesis of RPM which is capable of systemic spread in *N. tabacum*.

The O-coat protein coding sequence contained in pTB2 was cut from pTB2 by digestion with AhaIII. The UI-coat protein coding sequence was removed from pTMV204 by digestion with AhaIII and inserted into AhaIII-digested pTB2 to produce vector pT8U5 (FIG. I)

The XhoI/SalI fragments from pNC4X (DHFR sequence) and pNU116 (NPTII sequence), respectively, are ligated into the XhoI site of pTBU5 in the same sense as the TMV coding sequences. *N. tabacum* plants are inoculated and analyzed as described in Example 1. Functional enzymes are seen in the systemically infected plants but not in the control plants.

Example 3

This example describes the synthesis of RPVNA in which the native coat protein gene is under control of its native subgenomic promoter and a non-native subgenomic promoter has been inserted to drive the expression of non-native nucleic acid.

The TMV-O promoter and the TMV-UI coat protein sequence are removed from pTB2 by digesting with XhoI and KpnI. The XhoI end is converted to a PstI site by blunt-ending and adding a PstI linker. This PstI/KpnI fragment is subcloned into a Bluescript vector. Two subclones of this Bluescript vector are created by site-directed mutagenesis as follows:

Bluescript Sub I is prepared by using PCT techniques to create a site-specific fragment that will force a mutation at the ATG (coat protein) start site and create a XhoI site near the ATG site. Bluescript Sub 2 is prepared by using PCR techniques to create a site-specific fragment that will force a mutation at the TAA (coat protein) stop site and create a XhoI site near the TAA site. A PstI/XhoI cut of the Bluescript Sub I and a XhoI/KpnI cut of the Bluescript Sub 2 will give two fragments that can be ligated, giving a PstI/KpnI fragment that has a XhoI cloning insert site that is downstream from the TMV-O promoter. This PstI/KpnI fragment is inserted into the pTKUI vector that has had a NsiI/KpnI fragment removed. (PstI end can be ligated to NsiI). The resulting clone will be pTKU1-a with a TMV-O promoter on the 3' side and a XhoI insert site, into which can be inserted a gene-of-choice, that will be driven by the TMV-O promoter.

The XhoI/SalI fragments from pNC4X (DHFR sequence) and pNU116 (NPTII sequence), respectively, are ligated into the XhoI site of pTBU1-a in the same sense as the TMV coding sequences. *N. tabacum* plants are inoculated and analyzed as described in Example 1. Functional enzymes are seen in the systemically infected plants but not in the control plants.

Example 4

Additional DNA coding sequences were prepared for insertion into RVPNAs having either the O-coat protein (Example 1) or the U1-coat protein gene (Example 2). In each instance, the coding sequence was synthesized to contain the XhoI site of pTB2 (Example 1) or pTBU5 (Example 2), in the same sense as the coding sequence.

Standard procedures were used to transform the plasmids into *E. coli* and to isolate the DNA from an overnight culture. Following extraction of the plasmid DNA, an RNA copy of the TB2 or TBV5 vector (with or without the gene of choice) was made using a DNA-directed RNA polymerase. The RNA was capped during the reaction by adding $m^7GpppG_4$ during the transcription reaction, as previously published. This RNA was then used to inoculate a tobacco plant. Standard virus isolation techniques can be used to purify large concentrations of the transient vector for inoculations of multiple numbers of plants.

A coding sequence for Chinese cucumber α-trichosanthin containing XhoI linkers is shown in SEQ ID NO: 3, with the corresponding protein as SEQ ID NO: 4.

A coding sequence for rice α-amylase containing XhoI linkers is shown in SEQ ID NO: 5, with the corresponding protein as SEQ ID NO: 6. This sequence was prepared as follows:

The yeast expression vector pEno/I03 64 was digested with HindIII and treated with mung bean exonuclease to remove the single-stranded DNA overhang. The 0.16 kb HindIII (blunt end) fragment containing the entire rice α-amylase cDNA 05103 65 1990; GenBank accession number M24286) was digested with ScaI and linkered with a XhoI oligonucleotide (5'CCTCGAGG 3'). The modified α-amylase cDNA fragment was isolated using low-melt agarose gel electrophoresis, subcloned into an alkaline phosphatase treated XhoI site in pBluescript KS+(Stratagene, La Jolla, Calif.), and maintained in E. coli K-12 strain C-600.

A rice α-amylase coding sequence containing a short 3α-untranslated region was prepared as follows:

The E. coli vector pVC18/13 (64) was digested with KpnI, XhoI and treated with ExoIII and mung bean exonuclease. The modified plasmid was treated with DNA polI, DNA ligase, and transformed into C-600. An isolate, clone pUC18/3 #8, had a 3' deletion that was very close to the stop codon of 05103. This plasmid was digested with EcoRI, treated with mung bean exonuclease, and linkered with a XhoI oligonucleotide (5'CCTCGAGG 3'). A 1.4 Kb HindIII-XhoI fragment from the resulting plasmid (pUC18/3 #8X) was isolated using low melt agarose gel electrophoresis, subcloned into pBluescript KS- (Stratagene, La Jolla, Calif.) and maintained in E. coli K-12 strains C-600 and JM109. The deletion was sequenced by dideoxy termination using single-stranded templates. The deletion was determined to reside 14 bp past the rice a-amylase stop codon. Plasmid pUC18/3 #8X was digested with HindIII, treated with mung bean exonuclease, and linkered with a XhoI oligonucleotide (5 'CCTCGAGG 3') A 1.4 Kb XhoI fragment was isolated by trough elution, subcloned into an alkaline phosphatase-treated XhoI site in pBluescript KS+, and maintained in JM109.

A sequence listing containing the coding sequence for human α-hemoglobin or β-hemoglobin and transit peptide of petunia EFSP synthase is shown in SEQ ID NO: 7 or SEQ ID NO: 8, and corresponding protein sequences as SEQ ID NO: 9 and SEQ ID NO: 10, respectively.

Purified protein extracts from N. benthamiana treated with a recombinant plant viral nucleic acid containing the gene for α-trichosanthin, prepared in accordance with Example 1, were separated using polyacrylamide gel electrophoresis and probed with antibodies specific for α-trichosanthin using standard procedures for Western analysis. FIG. 2 is an autoradiograph of the gels which demonstrates production of processed α-trichosanthin protein in plants treated with a recombinant plant viral nucleic acid containing the gene for α-trichosanthin.

Example 5

Field Tests

The field site design contained two experiments (1 and 2). Experiment 1 was a typical row crop configuration that contained untreated border rows (8) of tobacco on all outside perimeter rows as well as internal rows. In addition, every fourth row was a spacer row (S) that was left unplanted in order to allow large farm equipment to access the field (e.g., for spraying pesticides) without coming into direct contact with any of the treated rows (T) Each inoculation was administered by direct hand application of the vector to a single leaf of an individual plant. No spray inoculum was used.

Experiment 2 was a typical plantbed configuration. A high density of plants per square foot was grown at a uniform height by frequent clipping of the plantbed using a modified mower attached to a tractor power takeoff. This experiment contained a complete perimeter border of plantbeds that was not inoculated with the vectors. Inoculation of the treated plantbeds was made using a downward-directed spray through the modified mower blade assembly and administered so as to prevent overspray to adjacent plantbeds.

Experiment 1 was a split-plot design using row culture with seven genotypes as main plots in randomized blocks and four replications. Each plot was 13 feet long and consisted of three rows, with only the middle three or four plants of each center row used for testing. Rows were four feet on center and plants spaced 20 to 22 inches in the row.

Experiment 2 was a randomized complete block design using plantbed culture with four genotypes and three replications. Each plot consisted of a 4-foot by 12-foot plantbed.

Genotypes. Experiment 1: (Nicotiana tabacum) K-326, Sp G-28, TI-560, Md-609, Galpao, Wisc-503B and Nicotiana benthamiana.

Experiment 2: (Nicotiana tabacum) K-326, TI-560, Md-609, Galpao.

Chemical Fertilization. Experiment 1: 800 lbs 6-12-18 after transplanting; 100 lbs 33-0-0 after first harvest; 200 lbs 15-0-14 after second harvest.

Experiment 2: 2400 labs 12-6-6 at time of plantbed formation; 300 labs 33-0-0 after first harvest; 670 lbs 15-0-14 after second harvest.

Clipping. Experiment 2 was clipped twice a week for two weeks, to impart uniformity to the plants.

Weed, Insect and Disease Control. Experiment 1: Prior to forming rows, Paarlan 6B (1 qt/A), Temik 15G (20lb/A) and Ridomil (2 qts/A) were broadcast-applied and incorporated by disking. During row formation, Telone C-17 (10.5 gal/A) was applied. After transplanting, Dipel (¼ lb/A) was applied to control budworms and hornworms. Orthene (⅜ lb/A) was applied to control aphids and hornworms as necessary.

Experiment 2: Ridomil 2G (1 qt/A; 1 oz/150 sq yds) was applied at seeding and at weekly intervals beginning 60-70 days after seeding (as needed). Carbamate 76WP (3 lb/100 gal water) was also used as foliar spray as needed in the initial plantbed stage, to control Anthracnose and Damping-off diseases. At normal transplanting size, Dipel (¼ lb/A) was applied. Orthene (⅜ lb/A) was applied to control aphids and hornworms as necessary.

Transplanting. Experiment 1 was transplanted using seedlings pulled from the plantbeds of Experiment 2.

Inoculation. Experiment 1: A single leaf on each non-control plant was hand-inoculated with a selected recombinant plant viral nucleic acid containing NPT II, α-trichosanthin or rice α-amylase. Each individual plant was inoculated with a single vector.

Experiment 2: The plants were inoculated with the vectors described in Experiment 1, using a spray applied through the deck of the clipping mower while the plants are being clipped a final time. Each non-control plot received only a single vector construct. Control plants received no inoculation with any vector.

Data Collection. Experiment 1: Sampling of both inoculated and control plant leaves was conducted on a schedule (approximately weekly) during first growth until plants were approximately 30 inches tall. Plants were then cut (harvest 1) with a rotary brush blade to leave six inches of stalk exposed above the ground. The plants were then allowed to continue growth (second growth) to a height of approximately 30 inches. Leaf samples were taken just before harvest 2. This procedure for cutting, growth and sampling was repeated for third growth and for fourth growth, if detectable amounts of the genes of interest inserted into the vectors were found.

Experiment 2: Sampling of 10 plants from each plot was conducted on a schedule (approximately weekly) from inoculation to harvest 1 and from harvest 1 until harvest 2. Following harvest 2, sampling was conducted only at harvest 3.

Sample Size and Analytical Methods. A 1.6 cm disk was excised from a single leaf near the apex of the plant. Each leaf disk was placed either in a 25 ml glass vial with screw cap and containing absolute ethanol or in a sealable plastic bag.

Leaf discs were either preserved in absolute ethanol or lyophilized. Depending on the specific gene product to be detected, leaf samples were prepared according to standard techniques for Northern or Western blot analyses or specific enzyme activity.

During first growth, visual monitoring of the pI ants treated with the RPVNA were conducted to observe any external phenotypic expression of the vector system. In some cases, the phenotypic expression was typical of Tobacco Mosaic Virus infections (lighter and darker "mosaic" patterns in the leaf). In other cases, the only symptoms seen were on the inoculated leaf, which included white or brown speckels of approximately 2 mm in diameter and/or suppression of the central vein elongation of the leaf.

Example 6

A full-length DNA copy of the OMV genome is prepared as described by Dawson, W. O. et al. (4). The vector containing the DNA copy of the OMV genome is digested with the appropriate restriction enzymes or suitable exonucleases to delete the coat protein coding sequence. The deletion of the coding sequence for the viral coat protein is confirmed by isolating OMV and using it to infect germinating barley plants. The isolated OMV RNA is incapable of spreading beyond the lesion under natural conditions. A vector containing the OMV sequences is prepared as described in Examples 1–3.

Example 7

A full-length DNA copy of the genome is prepared as described by Dawson, W. O. et al. (4). The vector containing the DNA copy of the ENV genome is digested with the appropriate restriction enzymes or suitable exonucleases so as to delete the coat protein coding sequence. The deletion of the coding sequence for the viral coat protein is confirmed by isolating RNV RNA and using it to infect germinating barley plants. The isolated is incapable of spreading beyond the lesion under natural conditions. A vector containing the OMV sequences is prepared as described in Examples 1–3.

Example 8

A full-length DNA copy of the PVY or PVX genome is prepared as described by Dawson, W. O. et al. (4). The vector containing the DNA copy of the PVY or PVX genome is digested with the appropriate restriction enzymes or suitable exonucleases to delete the coat protein coding sequence. The deletion of the coding sequence for the viral coat protein is confirmed by isolating PVY or PVX ENA and using it to infect potato plants. The isolated PVY or PVX RNA is incapable of spreading beyond the lesion under natural conditions. A vector containing the OMV sequences is prepared as described in Examples 1–3.

Example 9

A full-length DNA copy of the maize streak virus (MSV) genome is prepared as described by Dawson, W. O. et al. (4). The vector containing the DNA copy of the Msv genome is digested with appropriate restriction enzymes or suitable exonucleases to delete the coat protein coding sequence. Deletion of the coding sequence for the viral coat protein is confirmed by isolating MSV and using it to infect potato plants. The isolated MSV is incapable of spreading beyond the lesion under natural conditions. A vector containing the OMV sequences is prepared as described in Examples 1–3.

Example 10

A full-length DNA copy of the TGMV genome is prepared as described by Dawson, W. O. et al. (4). The vector containing the DNA copy of the TGMV genome is digested with the appropriate restriction enzymes or suitable exonucleases to delete the coat protein coding sequence. The deletion of the coding sequence for the viral coat protein is confirmed by isolating TGMV RNA and using it to infect potato plants. The isolated TGMV RNA is incapable of spreading beyond the lesion under natural conditions. A vector containing the TGMA sequences is prepared as described in Examples 1–3.

Example 11

The coding sequence for beta-cyclodextrin glucotransferase is isolated from alkalophilic Bacillus sp. strain No. 38-2 in the following manner:

The chromosomal DNA of strain No. 38-2 (66) is partially cleaved with Sau3AI, and the fragments ligated in BamHI-digested pBR322. A transformant carrying plasmid pCS115, which contains a 3.2 kb DNA fragment from the genome of the producing strain, has the CGT activity. The CGT produced by this transformant gives one line of precipitation which fuses completely with that for the No. 38-2 CGT by an Ouchterlony double-diffusion test. The nucleotide sequence of the fragment is found by the dideoxy chain termination reaction using pUC19, and the exonuclease deletion method (67). The nucleotide sequence of the fragment shows a single open reading frame corresponding to the CGT gene. A protein with a molecular mass of 66 kDal could be translated from this open reading frame of 1758 bp. For the detailed nucleotide sequence, see Hanamoto, T. et al. (66).

The sequence of the N-terminal amino acids of the extracellular form of CGT is found with a peptide sequencer. $NH_2$-Ala-Pro-Asp-Thr-Ser-Val-Ser-A5n-Lys-Gln-Asn-Phe-Ser-Thr-Asp-Val-Ile (SEQ ID NO: 6) is identical to that deduced from the DNA sequence (residues 1 to 17). This result suggests that 27 amino acid residues (residues -27 to -1) represent a signal peptide which is removed during secretion of CGT. The molecular weight of the matured CGT calculated from the DNA sequence is 63,318.

A probe is prepared based on a portion of the amino acid sequence of cyclodextrin glucanotransferase and used to isolate the coding sequence for this enzyme. Alternatively, the beta cyclodextrin glucotransferase coding sequence is isolated following reverse transcription. The fragment containing the coding sequence is isolated and cloned adjacent the subgenomic promoter of the native viral coat protein gene in the vectors prepared in Examples 6–10.

Example 12

The RPVNA of Example 11 is used to infect corn plants (viruses based on OMV, RNV, or TGMV) or potato plants (viruses based on PVY or PVX). The infected plants are grown under normal growth conditions. The plants produce cyclodextrin glucotransferase which catalyzes the conversion of starch to cyclodextrin in the plant tissue. The cyclodextrin is isolated by conventional techniques.

Example 13

A. The coding sequence for an esterase is isolated from *Bacillus subtilis* Thai 1-8 (CBS 679.85) as follows. The positive selection vector pUN121 (68) is used. This vector carries an ampicillin resistance gene, a tetracycline resistance gene and a $C_1$-repressor gene. Transcription of the tetracycline gene is prevented by the gene product of the $C_1$-repressor gene. Insertion of foreign DNA into the BclI site of the $C_1$-repressor gene results in activation of the tetracycline gene. This allows positive selection of recombinants on ampicillin/tetracycline agar plates.

Partially Sau3a-digested *Bacillus subtillis* Thai 1-8 DNA is mixed with BclI-digested pUN121 DNA. After recirculation by the use of polynucleotide ligase, the DNA mixture is introduced into *E. coli* DH1 (ATCC No. 33849) using the $CaCl_2$ transformation procedure. One thousand *E. coli* colonies are obtained which are resistant to ampicillin and tetracycline. All transformants are stored and replica-plated according to Gergan et al. (69). Replicated colonies are screened using a soft agar overlay technique, based on a previously described procedure to detect esterase activity (70). Essentially, a mixture of 0.5% low-melting agarose, 0.5M potassium phosphate (pH 7.5), 0.5 mg/l β-naphthyl acetate and 0.5 mg/ml fast-blue is spread over the transformants. Within a few minutes, colonies with esterase or lipase activity develop purple color. Such colonies are grown overnight in $2^x$ YT (16 g/l Bactotryptone, 10 g/l yeast extract, 5 g/l NaCl) medium and subsequently assayed for their ability to convert S-naproxen ester to S-naproxen (the method of Example 1 of EP-A 0233656). One *E. coli* transformant is able to convert S-naproxen ester. The plasmid isolated from this transformant, which is called pNAPT-2 (CBS 67186). Its size is 9.4 kb.

HindIII restriction enzyme fragments of pNAPT-2 are ligated into pPNEO/ori. This is performed as described below. pPNeo/ori is constructed by ligating the 2.7 kb EcoRI/SmaI restriction fragment of pUC19 to the 2.5 kb EcoRI-SnaBI restriction fragment of pUB110. The resulting shuttle plasmid, pPNeo/ori (5.2 kb) has the capacity to replicate both in *E. coli* and in Bacillus species due to the presence of the pUC19 origin, and the pUB110 origin. In addition, pPNeo/ori carries a gene encoding ampicillin resistance and a gene encoding neomycin resistance.

For subcloning, HindIII-digested pNAPT-2 is mixed with HindIII-digested pPNeo/ori and ligated. The mixture is transformed to *E. coli* JM101 hsds as described (Maniatis et al., supra). *E. coli* JM101 hsds is obtained from the Phabagen collection (Accession No. PC 2493, Utrecht, The Netherlands). Colonies capable of hydrolyzing β-naphthyl acetate are selected as described in Example 56 of EPA 0 233 656. From two positive colonies, pNAPT-7 and pNAPT-8 plasmid DNA is isolated and characterized in detail by determining several restriction enzyme recognition positions.

B. The coding sequence for an *E. coli* esterase is prepared as follows:

Plasmids pIP1100 (isolated from *E. coli* BM 2195) and pBR322 are mixed, digested with AvaI, ligated and transformed into *E. coli*, and clones are selected on Em (200 /g/ml). Transformants resistant to Ap and Em but also to Sm are analyzed by agarose gel electrophoresis of crude lysates. The transformant harboring the smallest hybrid plasmid is selected, its plasmid DNA is digested with AvaI, and the 3.5 kb pIP1100 insert is purified and partially digested with Sau3A. The restriction fragments obtained are cloned into the BamHI site of pBR322 and transformants selected on Em are replica-plated on Sm. The plasmid content of transformants resistant only to Ap and Em is analyzed by agarose gel electrophoresis. DNA from the smallest hybrid, pAT63, is purified and analyzed by agarose gel electrophoresis after digestions with Sau3A, EcoRI, PstI or HindIII-BamHI endonucleases (not shown). Plasmid pAT63 consists of pBR322 plus a 1.66 kb pIP1100 DNA insert. Purified EcoRI-HindIII (1750-bp) and BamHI-PstI (970-bp) fragments of pAT63 are subcloned into pUC8 and found not to confer resistance to Em.

The HpaII-BamHI fragment of pAT63 is sequenced according by the Sanger technique. The complete sequence is shown in Ounissi, H. et al. (71).

C. The coding sequence from acylase is isolated from *Arthrobacter viscosus* 8895GU, ATCC 27277 follows.

A gene library of *A. viscosus* 8895GU is constructed by inserting EcoRI-cleaved *A. viscosus* chromosomal DNA into the EcoRI cleavage site of pACYC184. The vector DNA and *A. viscosus* DNA are both digested with EcoRI. The 5′ end of the vector DNA is dephosphorylated with calf intestinal alkaline phosphatase. Dephosphoroylated vector DNA and digested *A. viscosus* DNA are incubated with T4 DNA ligase and transformed into *E. coli* HB101. Transformed colonies of *E. coli* were screened by the *Serratia marcescens* overlay technique. Penicillin G was added to the medium. *S. marcescens* is sensitive to the deacylation product of penicillin G, 6-aminopenicillamic acid (6-APA). Colonies of transformed *E. coli* will produce areas of *S. marcescens* inhibition in overnight cultures. The plasmid carried by transformed *E. coli* is referred to as pHYM-1. The plasmid having opposite DNA orientation is designated pHYM-2 (72).

D. A coding sequence for human gastric lipase mRNA is prepared by guanidinium isothiocyanate extraction of frozen tissue. Polyadenylated RNA is isolated by oligo(dT)-cellulose chromatography. cDNA is prepared from human stomach mRNA by procedures well known in the art. cDNA is annealed to PstI-cut dG-tailed pBR322. The hybrid plasmid is transformed into *E. coli* DH1. Transformants are screened by colony hybridization on nitrocellulose filters. The probe used is synthesized from the rat lingual lipase gene and labeled by nick translation. Positive colonies are grown up and plasmids are analyzed by restriction endonuclease mapping.

An exterase acylase or lopase gene prepared as described above is removed from the appropriate vector, blunt-ended using mung bean nuclease or DNA polymerase I, and XhoI linkers added. This esterase with XhoI linkers is cleaved with XhoI and inserted into the vertors described in Examples 1-3 or 6-10 Infection of the appropriate host plants by the RPVNA prepared in accordance with Example 2 results in the synthesis of esterase, acylase or lipase in the plant tissue. The enzyme is isolated and purified by conventional techniques and used to prepare stereo-specific compounds.

Example 14

The coding sequence for CMS-T is isolated from a BamHI maize mtDNA library as described by Dewey, R. E., et al. (73). The ORF-13 coding sequence is isolated by restriction endonucleuse digestion followed by 5'-exonuclease digestion to the start codon. Alternatively, a restriction site is engineered adjacent the start codon of the ORF-13 coding sequence by site-directed oligonucleotide mutagenesis. Digestion with the appropriate restriction enzyme yields the coding sequence for ORF-13. The fragment containing the ORF-13 coding sequence is isolated and cloned adjacent the promoter of the native viral coat protein gene in the vectors prepared in Examples 6, 7 and 10.

Maize plants are infected by teh RPVNA prepared in accordance with Example 1. The infected plants are grown under normal growth conditions. The plants produce cms-T which induces male sterility in the infected maize plants.

Example 15

The coding sequence of $S_2$-protein (for self-incompatibility) is isolated from *Nicotiana alata* as described in EP-A 0 222 526. The $S_2$-protein coding sequence is isolated by restriction endonucleuse digestion followed by 5'-exonuclease digestion to the start codon. Alternatively, a restriction site is engineered adjacent the start codon of the $S_2$-protein coding sequence by site-directed oligonucleotide mutagenesis. Digestion with the appropriate restriction enzyme yields the coding sequence for $S_2$-protein. The fragment containing the $S_2$-protein coding sequence is isolated and cloned adjacent the promoter of the viral coat protein gene in the vectors prepared in Examples 1-3.

Tobacco plants are infected by the RPVNA prepared in accordance with Example 1, prior to pollen formation. The infected plants are grown under normal growth conditions. The plants produce S-protein which induces male sterility via the self-incompatibility mechanism.

The following example demonstrates that high levels of therapeutic proteins can be expressed using the plant RNA viral vectors of the present invention.

Example 16

Rapid and High Level Expression of Biologically Active α-trichosanthin in Transfected Plants Using a Novel RNA Viral Vector Trichosanthin is a eukaryotic ribosome inactivating protein found in the roots of a Chinese medicinal plant (74). In *Trichosanthes kirilowii* Maximowicz, α-trichosanthin is a monomeric protein which catalyzes the cleavage of an N-glycosidic bond in 28S rRNA (75,76). This reaction inhibits protein synthesis by affecting the ability of the 60S ribosomal subunit to interact with elongation factors. The mature compound has an approximate relative molecular mass of 27 kDa and is initially produced as a preprotein (77). During its biosynthesis, a putative 23 amino acid secretory signal peptide is removed and a 19 amino acid peptide is probably excised from the carboxy terminus.

Purified *T. kirilowii* derived α-trichosanthin causes a concentration-dependent inhibition of HIV replication in acutely infected CD4+ lymphoid cells, and in chronically infected macrophages (78,79). This compound is currently being evaluated in clinical studies as a potential therapeutic drug in the treatment for HIV infection (80). The exact mechanism of anti-HIV infection by α-trichosanthin is not known. Amino acids involved in catalysis and inhibition of HIV replication may be identified using site directed mutagenesis. Detailed structure/function analysis will require an abundant source of recombinant protein as well as a rapid method for generating and analyzing mutants. Although the expression of α-trichosanthin in *E. coli* has been reported previously (81, 97), the amount synthesized was low (approximately 0.01% total cellular protein), the carboxy terminal extension was not removed, and the biological activity of the compound was not determined.

Tobamoviruses, whose genomes consist of one plus-sense RNA strand of approximately 6.4 kb, have been used to produce heterologous proteins. RNA transcripts from viral cDNA clones serve as infectious templates, encoding proteins involved in RNA replication, movement, and encapsidation (82). Subgenomic RNA for messenger RNA synthesis is controlled by internal promoters located on the minus-sense RNA strand (83). TMV RNA viruses have been used previously to express Leu-enkephlin in tobacco protoplasts (84) and bacterial chloramphenicol acetyltransferase in inoculated tobacco leaves (85,86). These previous attempts to express foreign genes have resulted in either unstable constructs or loss of long distance viral movement. Recently, *Nicotiana benthamiana* plants transfected with a hybrid virus consisting of tobacco mosaic virus, strain U1 (TMV-U1) and an additional RNA subgenomic promoter from odontoglossum ringspot virus (ORSV) produce a systemic and stable expression of neomycin phosphotransferase (87).

Construction of pBGC152

The plasmid pSP6-TKUI contains the entire TMV-U1 genome fused to the SP6 promoter by oligonucleotide directed mutagenesis and inserted into pUC118 as a XhoI/KpnI fragment. The sequence of the mutagenesis primer used to attach the SP6 promoter sequence to the TMV genome is: 5'-GGGCTCGAGATTTAGGT-GACACTATAGTATTTTTACAACAATTACCA-3' wherein the XhoI site is in italics, the SP6 promoter is in boldface and the TMV sequence is underlined. The primer was attached to a TMV subclone called pC48 (Raffo, et al., *Virology* 184: 277-289 (1991)). The promoter was attached by PCR using the above primer and a primer complementary to TMV sequences 5673 to 5692. This amplification produced a fragment of ca. 614 bp, which was then digested with XhoI and EcoRI (TMV 270) to produce a ca. 292 bp fragment which was then subcloned into similarly cut pUC129 resulting in plasmid pSP6-T1.

pSP6-T1 was cut with XhoI and XmaI (a SmaI isoschizomer which cuts at TMV 256) and the resulting ca. 278 bp fragment was ligated into pTKU1 (Donson, et al. Proc. Natl. Acad. Sci. U.S.A. 88:7204–7208 (1991)) which had been modified by cutting at the unique PstI site at the 5' end of the genome, blunting with T4 DNA polymerase, followed by the addition of XhoI linkers. This resulted in the infectious clone pSP6-TKU1 and XmaI digested.

Figure 7:
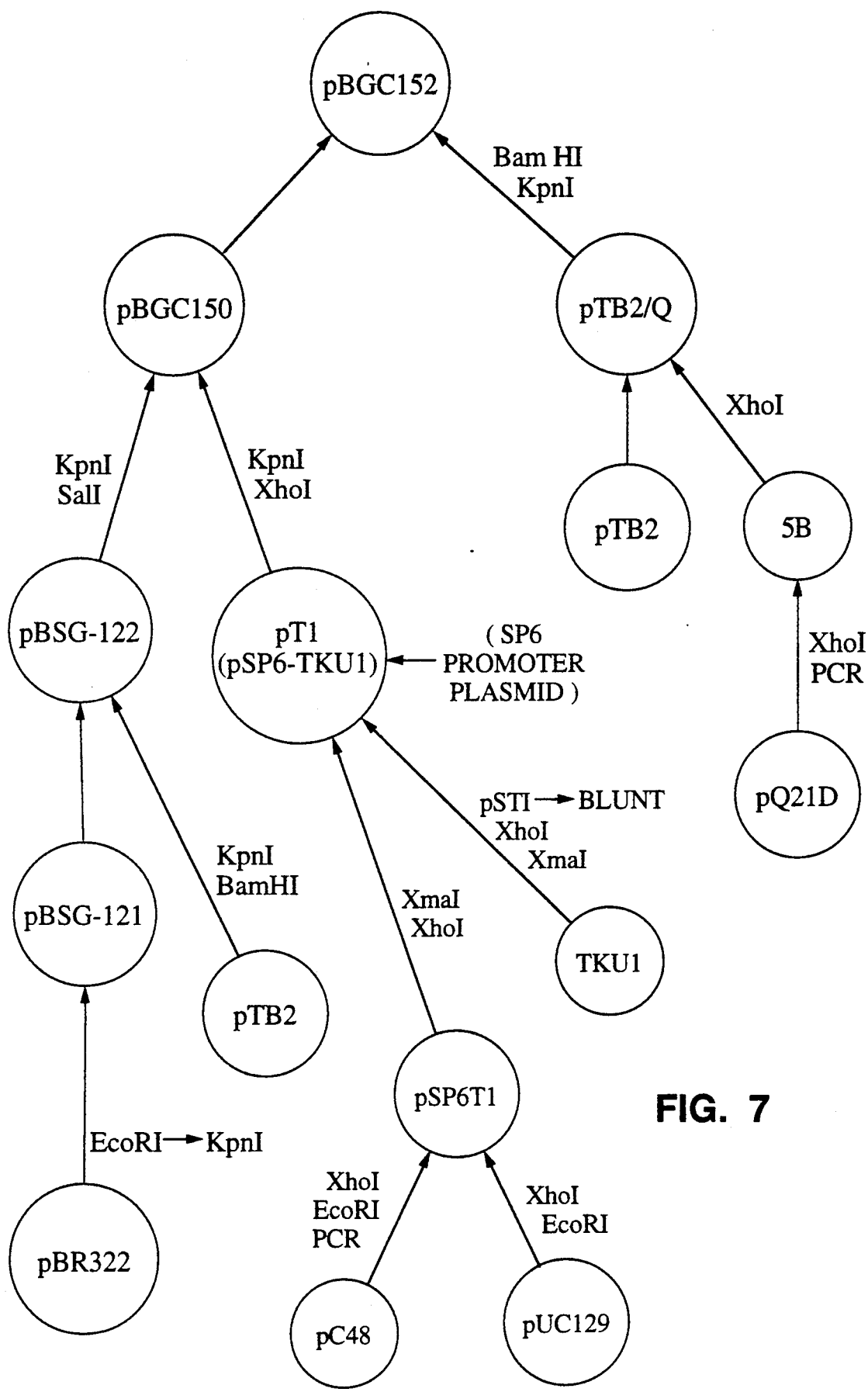
FIG. 7 illustrates the construction of the pBGC152 plasmid.

As shown in FIG. 7, the EcoRI site in pBR322 was mutagenized to a KpnI site using EcoRI, DNA polymerase (Klenow), and KpnI linkers. A KpnI BamHI fragment of the resulting plasmid, pBSG121, was substituted with a KpnI BamHI fragment of pTB2 (ATCC No. 75,280 deposited Jul. 24, 1992). A SalI/KpnI fragment of the resulting plasmid, pBSG122, was substituted with a XhoI/KpnI fragment of pSP6-TKUI (also known as T1) which resulted in plasmid pBGC150.

A BamHI/KpnI fragment of pBGC150 was substituted with a BamHI/-KpnI fragment of pTB2/Q resulting in plasmid pBGC152. pTB2/Q was constructed beginning with plasmid pQ21D (ATCC No. 67907) described in Piatak, Jr., et al. U.S. Pat. No. 5,128,460, the contents of which are incorporated herein by reference. The plasmid "clone 5B" containing a PCR amplified 0.88 kb XhoI fragment of the TCS sequence in pQ21D was obtained using oligonucleotide mutagenesis to introduce XhoI cloning sites at the start and stop codons of pQ21D such that the following sequence was obtained: 5'-CTCGAGGATG ATC --- ---//--- --- ATT TAG TAA CTCGAG-3' (XhoI site in italics). A 0.88 kb XhoI fragment from "clone B" was subcloned into the XhoI site of plasmid pTB2 in the sense orientation to create plasmid pTB2/Q.

In vitro transcriptions, inoculations, and analysis of transfected plants

N. benthamiana plants were inoculated with in vitro transcripts of KpnI digested pBGC152 as described previously (89). Virions were isolated from N. benthamiana leaves infected with BGC152 transcripts, stained with 2% aqueous uranyl acetate, and transmission electron micrographs were taken using a Zeiss CEM902 instrument.

Purification, immunological detection, and in vitro assay of α-trichosanthin

Two weeks after inoculation, total soluble protein was isolated from 3.0 grams of upper, non-inoculated N. benthamiana leaf tissue. The leaves were frozen in liquid nitrogen and ground in 3 mls of 5% 2-mercaptoethanol, 10 mM EDTA, 50 mM potassium phosphate, pH 6.0. The suspension was centrifuged and the supernatant, containing recombinant α-trichosanthin, was loaded on to a Sephadex G-50 column equilibrated with 2 mM NaCl, 50 mM potassium phosphate, pH 6.0. The sample was then bound to a Sepharose-S Fast Flow ion exchange column. Alphatrichosanthin was eluted with a linear gradient of 0.002–1M NaCl in 50 mM potassium phosphate, pH 6.0. Fractions containing α-trichosanthin were concentrated with a Centricon-20 (Amicon) and the buffer was exchanged by diafiltration (Centricon-10, 50 mM potassium phosphate, pH 6.0, 1.7M ammonium sulfate). The sample was then loaded on a HR5/5 alkyl superose FPLC column (Pharmacia) and eluted with a linear ammonium sulfate gradient (1.7–0M ammonium sulfate in 50 mM potassium phosphate, pH 6.0). Total soluble plant protein concentrations were determined (90) using BSA as a standard. The concentration of α-trichosanthin was determined using the molar extinction coefficient of $E_{280} = 1.43$. The purified proteins were analyzed on a 0.1% SDS, 12.5% polyacrylamide gel (91) and transfered by electroblotting for 1 hour to a nitrocellulose membrane (92). The blotted membrane was incubated for 1 hour with a 2000-fold dilution of goat anti-α-trichosanthin antiserum. The enhanced chemiluminescence horseradish peroxidase-linked, rabbit anti-goat IgG (Cappel) was developed according to the manufacturer's (Amersham) specifications. The autoradiogram was exposed for < 1 second. The quantity of total recombinant α-trichosanthin in an extracted leaf sample was determined by comparing the crude extract autoradiogram signal to the signal obtained from known quantities of purified GLQ223. The ribosome inactivating activity was determined by measuring the inhibition of protein synthesis in a rabbit reticulocyte lysate system.

Confirmation of High Level Expression of Bilogically Active α-trichosanthin

Figure 4:
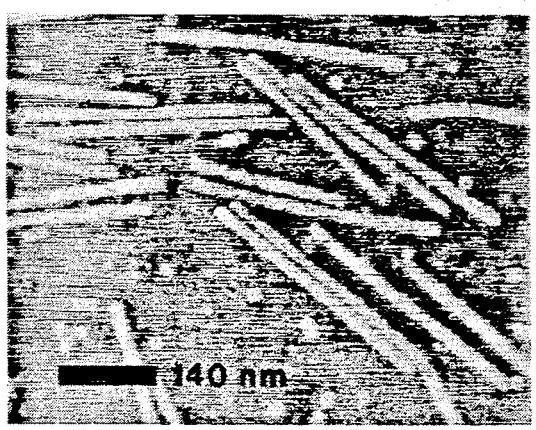
FIG. 4 illustrates an electron micrograph of virions from systemically infected leaves of *N. benthamiana* transfected with in vivo pBGC152 transcripts. The length of the black bar located in the bottom left corner of the micrograph represents approximately 140 nm.
Figure 5A:
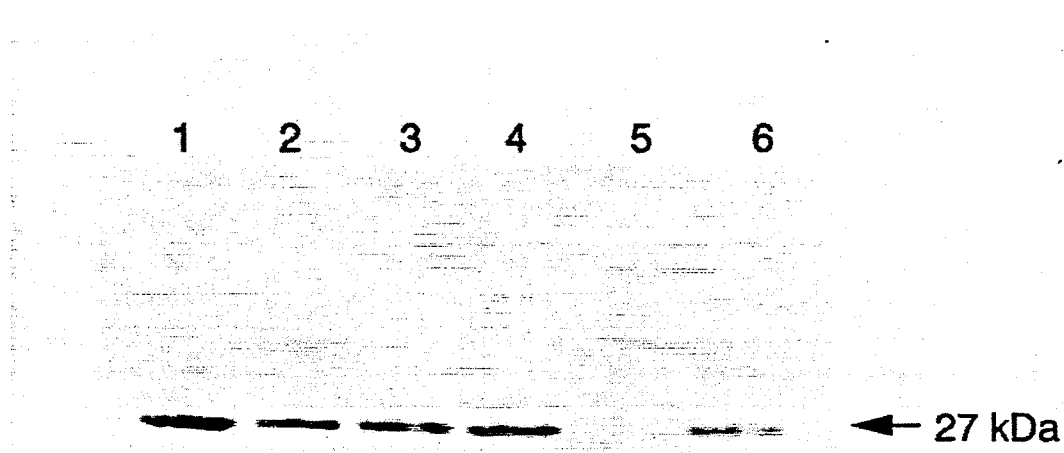
FIG. 5a is a protein analysis of a transfected *N. benthamiana* plant two weeks after inoculation. a, Western blot analysis. Lane 1: 200 ng of GLQ223; 2: 50 ng of GLQ223; 3: 7 μg of total soluble protein from *N. benthamiana* infected with pBGC152 transcripts; 4: peak fraction from alkyl superose FPLC chromatography; 5: 7 μg of total soluble protein from noninfected *N. benthamiana;* 6: 7 μg of total soluble protein from noninfected *N. benthamiana* and 100 ng of GLQ223.
Figure 5B:
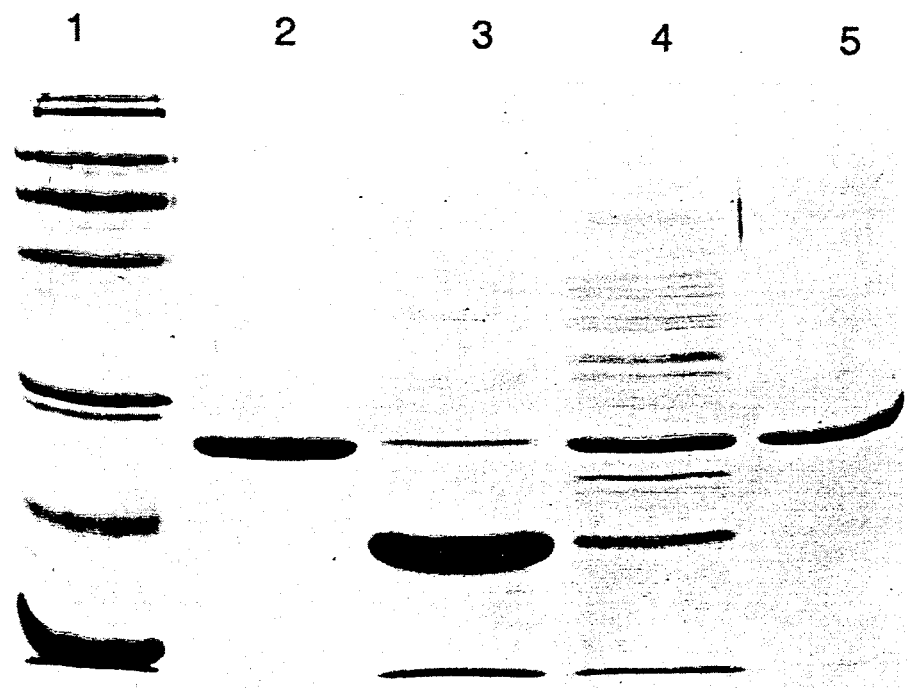
FIG. 5b is a purification profile of recombinant α-trichosanthin. The samples from various stages during purification were analyzed by 12.5% SDS-polyacrylamide gel electrophoresis. Lane 1: Amersham prestained high-range molecular weight standards; 2: purified GLQ223; 3: total soluble protein from *N. benthamiana* infected with pBGC152 transcripts; 4: peak fraction from S-sepharose chromatography; 5: peak fraction from alkyl superose FPLC chromatography.

The plant viral vector of the present invention directs the expression of α-trichosanthin in transfected plants. The open reading frame (ORF) for α-trichosanthin, from the genomic clone pQ21D (88), was placed under the control of the tobacco mosaic virus (TMV) coat protein subgenomic promoter. Infectious RNA from pBGC 152 (FIG. 3) was prepared by in vitro transcription using SP6 DNA-dependent RNA polymerase and were used to mechanically inoculate N. benthamiana. The hybrid virus spread throughout all the non-inoculated upper leaves as verified by transmission electron microscopy (FIG. 4), local lesion infectivity assay, and polymerase chain reaction (PCR) amplification (20; data not shown). The 27 kDa α-trichosanthin accumulated in upper leaves (14 days post inoculation) to levels of at least 2% of total soluble protein and was analyzed by immunoblotting, using GLQ223 (78), a purified T.kirilowii derived α-trichosanthin, as a standard (FIG. 5A). No detectable cross-reacting protein was observed in the non-infected N. benthamiana control plant extracts (FIG. 5A, lane 5). Recombinant α-trichosanthin was easily detected in 7 μg of crude leaf extract using a Coomassie stain (FIG. 5B, lane 3).

Prior investigators have reported a maximum accumulation of a foreign protein in any genetically engineered plant of 2% of the total soluble protein. Although the expression of potentially valuable proteins such as antibodies and human serum albumin has been reported previously (94,95) these were produced in Agrobacterium-mediated transgenic plants. A major difference between this plant viral expression system and previous methods is the quantity of protein produced and the amount of time required to obtain genetically engineered plants. Systemic infection and expression of α-trichosanthin occurred in less than two weeks while it takes several months to create a single transgenic plant.

The α-trichosanthin produced and purified from upper leaves in transfected N. benthamiana (14 days post inoculation) was structurally identical to native α-trichosanthin. The 27 kDa protein cross-reacted with anti-α-trichosanthin antibody and had an identical FPLC purification profile as the GLQ223 standard. Although the C-terminal sequence of the recombinant protein was not analyzed, both GLQ223 and the purified recombinant α-trichosanthin appeared to have identical electrophoretic mobilities (FIG. 5B). The exact C-terminal amino acid of the recombinant α-trichosanthin remains to be determined. The N-terminal sequence, Asp-Val-Ser-Phe-Arg-Leu-Ser was obtained from the purified protein using an automated protein sequenator (96). This result indicated that the putative signal peptide of the preparation was correctly processed at the site indicated in FIG. 1. The removal of the putative signal peptide at this site was consistent with the statistical expectation by the method of von Heijne (97). It is possible that the α-trichosanthin signal peptide contributed to its high level expression by targeting the protein into the extracellular space. The nucleotide sequences surrounding the α-trichosanthin start codon might also have an effect on the efficiency of translation initiation.

It is interesting to note that nucleotides flanking the translation initiating sites of the highly expressed TMV-U1 (5′ TTAAATATGTCT 3′) and ORSV (5′ TGAAATATGTCT 3′) coat protein genes are conserved while the corresponding region in pBGC152/α-trichosanthin (5′ TCGAGGATGATC 3′) shows very little similarity. It is possible that site directed mutagenesis of nucleotides near the translation initiation site of α-trichosanthin might increase its expression.

Figure 6:
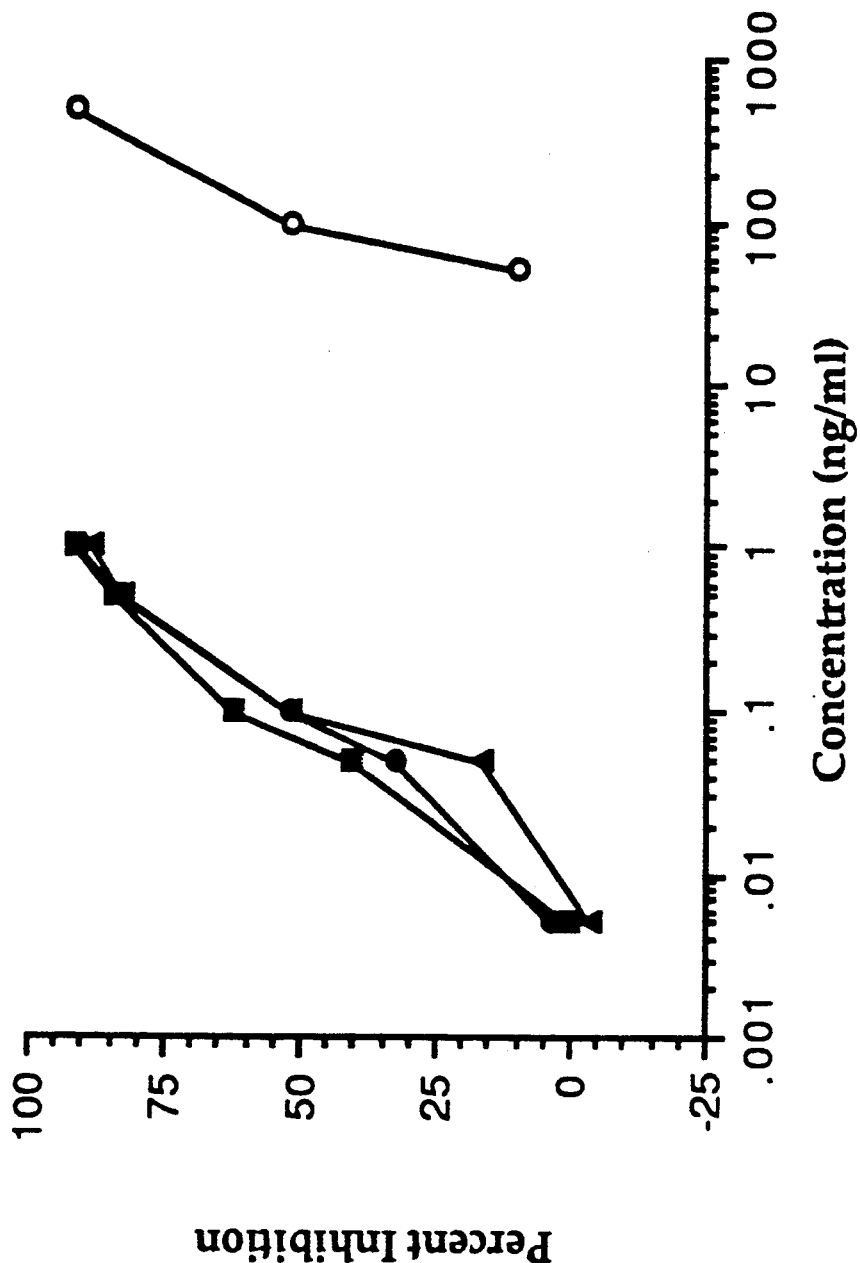
FIG. 6 illustrates the inhibition of protein synthesis in a cell-free rabbit reticulocyte translation assay. Dosage required for 50% inhibition ($ID_{50}$). Purified α-trichosanthin from *N. benthamiana* infected with BGC 152 transcripts (blackened circles and triangles, repetition 1 and 2), GLQ233 (blackened square), and cycloheximide (open circle) were analyzed in varying concentrations for their ability to inhibit protein synthesis in vitro.

The recombinant α-trichosanthin caused a concentration dependent inhibition of protein synthesis in a cell-free rabbit reticulocyte translation assay (FIG. 6). The $ID_{50}$ (dosage required for 50% inhibition) was approximately 0.1 ng/ml, a value comparable to *T. kirilowii* derived α-trichosanthin (GLQ223). Based on the $ID_{50}$ and dose response, the enzyme produced in transfected plants had the same specific activity as the native protein. This result suggests that the fidelity of the viral RNA-dependent RNA polymerase was relatively high since base pair substitutions and deletions in the foreign sequence during viral amplification would lower the specific activity of the recombinant enzyme.

As the disclosed and claimed invention demonstrates, pBGC152 can direct the heterologous expression of biologically active α-trichosanthin in transfected plants. Large scale production of recombinant proteins can be easily obtained using the RNA viral-based system by simply increasing the size and number of inoculated plants. Since tissue containing high concentrations of α-trichosanthin can be harvested two weeks after inoculation this system can be used to rapidly screen the effects of site directed mutations. Identification of important amino acids involved in the inhibition of HIV replication in vivo may help to improve the efficacy of α-trichosanthin as a potential AIDS therapeutic drug.

The following plasmids have been deposited at the American Type Culture Collection (ATCC), Rockville, Md., U.S.A., under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such plasmids is not to be construed as a license to practice the invention in contravention of the rights granted under the authority of any government in accordance with its patent laws.

The deposited cultures have been assigned the indicated ATCC deposit numbers:

| Plasmid | ATCC No. |
|---|---|
| pTB2 | 75280 |
| pTBU5 | 75281 |

While the invention has been disclosed in this patent application by reference to the details of preferred embodiments of the invention, it is to be understood that this disclosure is intended in an illustrative rather than limiting sense, as it is contemplated that modifications will readily occur to those skilled in the art, within the spirit of the invention and the scope of the appended claims.

LISTING OF REFERENCES

1. Grierson, D. et al., Plant Molecular Biology, Blackie, London, pp. 126-146 (1984).
2. Gluzman, Y. et al., Communications in Molecular Biology: Viral Vectors, Cold Spring Harbor Laboratory, New York, pp. 172-189 (1988).
3. Ahlquist, P. and M. Janda, Mol. Cell Biol. 4:2876 (1984)
4. Dawson, W. O. et al., Proc. Nat. Acad. Sci. USA 83:1832 (1986).
5. Lebeurier, 6. et al., Gene 12:139 (1980).
6. Morinaga, T. et al. U.S. Pat. No. 4,855,237.
7. Maniatis, T. et al., Molecular Cloning (1st Ed.) and Sambrook, J. et al. (2nd Ed.), Cold Spring Harbor Laboratory, Cold Spring Harbor (1982, 1989).
8. Molecular Cloning, D. M. Clover, Ed., IRL Press, Oxford (1985).
9. Methods in Enzymology, Vols. 68, 100, 101, 118 and 152-155 (1979, 1983, 1983, 1986 and 1987).
10. Brisson, N. et al., Methods in Enzymology 118:659 (1986).
11. Dawson, W. O. et al., Virology 172:285-292 (1989).
12. Takamatsu, N. et al., EMBO J 6:307-311 (1987).
13. French, R. et al., Science 231:1294-1297 (1986).
14. Takamatsu, N. et al., FEBS Letters 269:73-76 (1990).
15. Miller, J. H., Experiments in Molecular Genetics, Cold Spring Harbor Laboratory, New York (1972).
16. Virology 132:71 (1984).
17. Deom, C. M. et al., Science 237:389 (1987).
18. Noru, Y. et al., Virology 45:577 (1971).
19. Kurisu et al., Virology 70:214 (1976).
20. Fukuda, M. et al., Proc. Nat. Acad. Sci. USA 78:4231 (1981).
21. Lebeurier, G. et al., Proc. Nat. Acad. Sci. USA 74:1913 (1977).
22. Fukuda, M. et al., Virology 101:493 (1980).
23. Meshi, T. et al., Virology 127:52 (1983).
24. Alquist et al., J. Mol. Biol. 153:23 (1981).
25. Hedgpeth, J. M. et al., Mol. Gen. Genet. 163:197 (1978).
26. Bernard, H. M. et al., Gene 5:59 (1979).
27. Remaut, E. P. et al., Gene 15:81 (1981).
28. Grimsley, N. et al., Nature 325:177 (1987).
29. Gardner, R. C. et al., Plant Mol. Biol. 6:221 (1986).
30. Grimsley, N. et al., Proc. Nat. Acad. Sci. USA 83:3282 (1986).
31. Lazarowitz, S. C., Nucl. Acids Res. 16:229 (1988).
32. Donson, J. et al., Virology 162:248 (1988).
33. Hayes, R. J. et al., J. Gen. Virol. 69:891 (1988).
34. Elmer, J. S. et al., Plant Mol. Biol. 10:225 (1988).
35. Gardiner, W. E. et al., EMBO J 7:899 (1988).
36. Huber, M. et al., Biochemistry 24, 6038 (1985).
37. Tanksley et al., Hort Science 23, 387 (1988).
38. Rao, et al., Journal of Heredity 74:34 (1983).
39. Dewey, et al., Cell 44:439-449 (1986).
40. Pearson, O. N., Hort. Science 16:482 (1981).
41. Konvicha et al., Z. Pfanzenzychtung 80:265

LISTING OF REFERENCES

42. Remy et al., Theor. Appl. Genet. 64:249 (1983).
43. Padmaja et al. Cytologia 53:585 (1988).
44. Ebert et al., Cell 56:255 (1989).
45. Dawson, W. O. et al., Phytopathology 78:783 (1988).
46. Goelet, P. et al., Proc. Nat. Acad. Sci. USA 79:5818 (1982).
47. Shaw, W. V., Meth. Enzymology 53:737 (1975).
47a. Logemann, J. et al., Anal. Biochem. 163:16 (1987).
48. Ausubel, F. M. et al., Current Protocols in Mol. Biol., Wiley, N.Y. (1987).
49. Zagursky, R. et al., Gene Anal. Tech. 2:89 (1985).
50. Goelet, P. an Karn, J., J. Mol. Biol. 154:541 (1982).
51. Dougherty, W. G., Virology 131:473 (1983).
52. Kirkegaard, K. and Baltimore, D., Cell 47:433 (1986).
53. Bujarski, J. and Kaesberg, P., Nature 321:528 (1986).
54. King, A. M. Q., in RNA Genetics, E. Domingo et al., Eds., Vol. II, 149-165, CRC Press, Inc., Boca Raton, Fla. (1988).
55. Keen, N. T. et al., Gene 70:191 (1988).
56. Beck, E. et al., Gene 19:327 (1982).
57. Brisson, N. et al., Nature 310:511 (1984).
58. Rogers, S. G. et al., Plant Mol. Biol. Rep. 3:111 (1985).
59. Gooding Jr., G. V. and Herbert T. T., Phytopathology 57:1285 (1967).
60. Feinberg, A. P. and Vogelstein, B., Anal. Biochem. 137:266 (1984).
61. Bradford, M. M., Anal. Biochem. 72:248 (1976).
62. McDonnell, R. E. et al., Plant Mol. Biol. Rep. 5:380 (1987).
63. French, R. and Ahlquist, P., J. Virol. 62:2411 (1988).
64. Kurnagi, M. H. et al., Gene 94:209 (1990).
65. O'Neill, S. D. et al., Mol. Gen. Genet. 221:235 (1990).
66. Hanamoto, T. et al., Agric. Biol. Chem. 51:2019 (1987).
67. Henikoff, S., Gene 28:351 (1984).
68. Nilsson et al., Nucl. Acids Res. 11:8019 (1983).
69. Gergan et al., Nucl. Acids Res. 7:2115 (1979).
70. Higerd et al., J. Bacteriol. 114:1184 (1973).
71. Ounissi, H. et al., Gene 35:271 (1985).
72. Ohashi, H. et al. Appl. Environ. Microbiol. 54:2603 (1988).
73. Dewey, R. E. et al., Cell 44:439 (1986).
74. Wang, Y., Qian, R. -Q., Gu., Z. -W., Jin, S. -W., Zhang, L. -Q., Xia, Z. -X., Tian, G. -Y. & Ni, C. -Z. Pure appl. Chem. 58, 789-798 (1986).
75. Jimenez, A. & Vazquez D. Annu. Rev. Microbiol. 39, 649-672 (1985).
76. Endo, Y., Mitsui, K., Motizuui, M. & Tsurugi, K. J. biol. Chem. 262, 5908-5912 (1987).
77. Maraganore, J. M., Joseph, M. & Bailey, M. C., J. biol. Chem. 262, 11628-11633 (1987).
78. Collins, E. J., Robertus, J. D., LoPresti, M., Stone, K. L., Williams, K. R., Wu, P., Hwang, & Piatak, M., J biol. Ckem. 265, 8665-8669 (1990).
79. McGrath., M. S., Hwang, K. M., Caldwell, S. E., Gaston, I., Luk, K. -C., Wu, P., Ng, V. L., Crowe, S., Daniels, J., Marsh, I., Dienhart, T., Lekas, P. V., Vennari, J. C., Yeung, H. J. & Lifson, D. Proc. natn. Acad. Sci. U.S.A. 86, 2844-2848 (1989).
80. Shaw, P. -C., Yung, M. -H., Zhu, R. -H., Ho, W. K. -K., Ng, T. -B. & Yeung, H. -W. Gene, 97, 267-272 (1991).
81. Ahlquist, P., French, R., Janda, M. & Loesch-Fries, S. Proc. natn. Acad. Sci. U.S.A. 81, 7066-7070 (1984).
82. Miller, W. A., Dreher, T. W. & Hall, T. C. Nature 313, 68-70 (1985).
83. Takamatsu, N., Watanabe, Y., Yanagi, H., Meshi, T., Shiba, T. & Okada, Y. FEBS Lett. 269, 73-76 (1990).
84. Talcamatsu, N., Ishilcawa, M., Meshi, T. & Okada, Y. EMBO J. 6, 307-311 (1987).
85. Dawson, W. O., Lewandowski, D. J., Hilf, M. E., Bubrick, P., Raffo, A. J., Shaw, J. J., Grantham, G. L. & Desjardins, P. R. Virology 172, 285-292 (1989).
86. Donson, J., Kearney, C. M., Hilf, M. E. & Dawson, W. O. Proc. natn. Acad. Sci. U.S.A. 88, 7204-7208 (1991).
87. Chow, T. P., Feldman, R. A., Lovett, M. & Piatak, M. J. biol. Chem. 265, 8670-8674 (1990).
88. Saiki, R. K., Scharf, S., Faloona, F., Mullis, K. B., Horn, G. T., Erlich, H. A. & Amheim, N. Science 230, 1350-1354 (1985).
89. Hiatt, A., Cafferkey, R. & Bowdish, K. Nature 342, 76-78 (1989).
90. Sijmons, P. C., Dekker, B. M. M., Schrammeijer, B., Verwoerd, T. C., van den Elzen, P. J. M. & Hoekema, A. Bio/Technology 8, 217-221 (1990).
91. Hewick, R. M., Hunkapiller, N. W., Hood, L. E. & Dreyer, W. J. J. biol. Chem. 256, 7990-7997 (1981).
92. von Heijne, G. Nucleic Acid Res. 14, 4683-4690 (1986).
93. Dawson, W. O., Beck, D. L., Knorr, D. A. Granthain, G. L. Proc. natn. Acad. Sci. U.S.A. 83, 1832-1836 (1986).
94. Laemmli, U. K. Nature 227, 680-685 (1970).
95. Bradford, M. M. Anal. Biochem. 72, 248-254 (1976).
96. Towbin, H., Staehelin, T., Gordon, J. Proc. Natl. Acad. Sci. U.S.A. 76, 4350-4354 (1979).
97. Piatak, et al., U.S. Pat. No. 5,128,460 (1992).

What is claimed is:

1. A recombinant plant viral nucleic acid derived from a plus sense, single stranded RNA plant virus that naturally has a subgenomic promoter, the recombinant plant viral nucleic acid comprising:

a first viral subgenomic promoter operably joined to a first nucleic acid sequence that codes for a plant viral coat protein wherein the transcription of the first nucleic acid sequence is regulated by the first plant viral subgenomic promoter; and a second plant viral subgenomic promoter operably joined to a second nucleic acid sequence which is not naturally associated with said plus sense single stranded RNA plant virus wherein transcription of the second nucleic acid sequence is regulated by the second plant viral subgenomic promoter;

wherein the first viral subgenomic promoter is heterologous to the second viral subgenomic promoter. enabling the recombinant plant viral nucleic acid to systemically transcribe the second nucleic acid in the host plant.

2. A recombinant plant viral nucleic acid of claim 1 wherein the first plant viral subgenomic promoter is naturally associated with said plus sense single stranded RNA plant virus.

3. A recombinant plant viral nucleic acid of claim 2 wherein the nucleic acid sequence that codes for a plant viral coat protein is naturally associated with said plus sense single stranded RNA plant virus.

4. A recombinant plant viral nucleic acid of claim 2 wherein the second plant viral subgenomic promoter is not naturally associated with said plus sense single stranded RNA plant virus.

5. A recombinant plant viral nucleic acid of claim 1 wherein the first plant viral subgenomic promoter is not naturally associated with said plus sense single stranded RNA plant virus.

6. A recombinant plant viral nucleic acid of claim 5 wherein the nucleic acid sequence that codes for a plant viral coat protein is naturally associated with said plus sense single stranded RNA plant virus.

7. A recombinant plant viral nucleic acid of claim 5 wherein the second plant viral subgenomic promoter is naturally associated with said plus sense single stranded RNA plant virus.

8. A recombinant plant viral nucleic acid of claim 1 further comprising a third viral subgenomic promoter and a the third viral subgenomic promoter is heterologous to each of the first and second viral subgenomic promoters thereby enabling the recombinant plant viral nucleic acid to systemically transcribe the third nucleic acid in the host plant.

9. A recombinant plant viral nucleic acid of claim 1 wherein the plus sense, single stranded RNA plant virus is selected from the group consisting of tobamoviruses, brome mosiac viruses, rice necrosis viruses and gemini viruses.

10. A recombinant plant viral nucleic acid of claim 9 wherein the tobamovirus is a TMV virus.

11. A host plant infected by the recombinant plant viral nucleic acid of claim 1.

12. A host plant infected by the recombinant plant viral nucleic acid of claim 2.

13. A host plant infected by the recombinant plant viral nucleic acid of claim 3.

14. A host plant infected by the recombinant plant viral nucleic acid of claim 4.

15. A host plant infected by the recombinant plant viral nucleic acid of claim 5.

16. A host plant infected by the recombinant plant viral nucleic acid of claim 6.

17. A host plant infected by the recombinant plant viral nucleic acid of claim 7.

18. A host plant infected by the recombinant plant viral nucleic acid of claim 8.

19. A host plant infected by the recombinant plant viral nucleic acid of claim 9.

20. A host plant infected by the recombinant plant viral nucleic acid of claim 10.

21. A process for systemically transcribing a nucleic acid sequence in a host plant comprising:
   (a) infecting a host plant with a recombinant plant viral nucleic acid derived from a plus sense, single stranded RNA plant virus that naturally has a subgenomic promoter, the recombinant plant viral nucleic acid comprising:
   a first viral subgenomic promoter operably joined to a first nucleic acid sequence that codes for a plant viral coat protein wherein the transcription of the first nucleic acid sequence is regulated by the first plant viral subgenomic promoter; and
   a second plant viral subgenomic promoter operably joined to a second nucleic acid sequence which is not naturally associated with said plus sense single stranded RNA plant virus wherein transcription of the second nucleic acid sequence is regulated by the second plant viral subgenomic promoter;
   wherein the first viral subgenomic promoter is heterologous to the second viral subgenomic promoter thereby enabling the recombinant plant viral nucleic acid to systemically transcribe the second nucleic acid in the host plant; and
   (b) growing the infected plant wherein the second nucleic acid sequence is systemically transcribed.

22. A process according to claim 21 which further comprises isolating the transcribed second nucleic acid sequence.

23. A process according to claim 21 comprising the further step of systemically expressing a protein encoded by the second nucleic acid sequence.

24. A process according to claim 23 which further comprises isolating the expressed protein.

25. A process according to claim 21 which further comprises the step of systemically expressing a protein that regulates production of a secondary metabolite within the plant.

26. A process according to claim 25 which further comprises isolating the secondary metabolite.

27. A process according to claim 21 wherein the first plant viral subgenomic promoter is naturally associated with said plus sense single stranded RNA plant virus.

28. A process according to claim 27 wherein the nucleic acid sequence that codes for a plant viral coat protein is naturally associated with said plus sense single stranded RNA plant virus.

29. A process according to claim 21 wherein the second plant viral subgenomic promoter is not naturally associated with said plus sense single stranded RNA plant virus.

30. A process according to claim 21 wherein the first plant viral subgenomic promoter is not naturally associated with said plus sense single stranded RNA plant virus.

31. A process according to claim 30 wherein the nucleic acid sequence that codes for a plant viral coat protein is naturally associated with said plus sense single stranded RNA plant virus.

32. A process according to claim 31 wherein and the second plant viral subgenomic promoter is naturally associated with said plus sense single stranded RNA plant virus.

33. A process of claim 21 wherein the plus sense, single stranded RNA plant virus is selected from the group consisting of tobamoviruses, brome mosiac viruses, rice necrosis viruses and gemini viruses.

34. A process of claim 33 wherein the plus sense, single stranded RNA plant virus is a tobamovirus.

35. A process according to claim 21 wherein a gene product is produced from the systemic transcription of the second nucleic acid sequence, the gene product being selected from the group consisting of IL-1, IL-2, IL-3, IL-4, IL-5, IL-6, IL-7, IL-8, IL-9, IL-10, IL-11, IL-12, EPO, G-CSF, GM-CSF, hPG-CSF, M-CSF, Factor VIII, Factor IX, tPA, hGH, receptors, receptor antagonists, antibodies, neuro-polypeptides, melanin, insulin and vaccines.

36. A process according to claim 21 wherein a gene product is produced from the systemic transcription of the second nucleic acid sequence, the gene product being a biologically inactive polypeptide or protein resulting from anti-sense RNA expression.

37. A DNA vector designated as pTB2 having American Type Culture Collection accession number 75280.

38. A DNA vector designated as pTBU5 having American Type Culture Collection accession number 75281.

* * * * *

UNITED STATES PATENT AND TRADEMARK OFFICE
CERTIFICATE OF CORRECTION

PATENT NO. : 5,316,931
APPLICATION NO. : 07/923692
DATED : May 31, 1994
INVENTOR(S) : Donson et al.

It is certified that error appears in the above-identified patent and that said Letters Patent is hereby corrected as shown below:

Title Page;
In Section (56), Other Publications:
Page 1, delete "Alquist" and insert -- Ahlquist --.
Page 2, first column, in "Deom" reference, delete "Sicence" and insert -- Science --.
Page 3, first column, in "Kirkegaard" reference, delete "REcombination" and insert -- Recombination --.
Page 3, second column, in "French" reference, delete "Alhquist" and insert -- Ahlquist --.
Page 4, second column, in "Donson" reference, delete "tobacoo" and insert -- tobacco --.
Page 4, second column, in "Saiki" reference, delete "Restricition" and insert -- Restriction --.
Page 4, second column, in "Laemmli" reference, delete "Strucutral" and insert -- Structural --.

In Column 2, Line 42, delete "Ahlguist" and insert -- Ahlquist --.

In Column 7, Line 24, delete "vrome" and insert -- brome --.

In Column 10, Line 53, delete "Alquist" and insert -- Ahlquist --.

In Column 21:
Lines 20-21, delete "sequencs" and insert -- sequences --.
Line 61, delete "whih" and insert -- which --.

In Column 23, Line 2, delete "systermic" and insert -- systemic --.

In Column 25:
Line 4, delete "transferrable" and insert -- transferable --.
Line 28, delete "teh" and insert -- the --.

In Column 27, Line 67, delete "assey" and insert -- assay --.

In Column 28:
Line 43, delete "prevously" and insert -- previously --.
Line 44, delete "recomb ination" and insert -- recombination --.

In Column 29, Line 57, delete "benthaniana" and insert -- benthamiana --.

UNITED STATES PATENT AND TRADEMARK OFFICE
CERTIFICATE OF CORRECTION

PATENT NO. : 5,316,931
APPLICATION NO. : 07/923692
DATED : May 31, 1994
INVENTOR(S) : Donson et al.

It is certified that error appears in the above-identified patent and that said Letters Patent is hereby corrected as shown below:

In Column 33:
Line 32, delete "pI ants" and insert -- plants --.
Line 39, delete "speckels" and insert -- speckles --.

In Column 34, Line 63, delete "Hanamoto" and insert -- Hamamoto --

In Column 37:
Line 12, delete "vertors" and insert -- vectors --.
Lines 23 and 42, delete "endonucleuse" and insert -- endonuclease --.
Line 33 "teh" and insert -- the --.

Column 40:
Line 7, delete "transfered" and insert -- transferred --.
Line 23, delete "Bilogically" and insert -- Biologically --.

Column 42, Line 50, delete "Alquist" and insert -- Ahlquist --.

Column 43, Line 35, delete "Kumagi" and insert -- Kumagai --.

Column 61, Line 60, delete "promoter." and insert -- promoter --.

Column 63, Line 6 and Column 64, Line 37, delete "mosaic" and insert -- mosaic --.

Signed and Sealed this

Second Day of October, 2007

JON W. DUDAS
*Director of the United States Patent and Trademark Office*

SEQUENCE LISTING ( 1 ) GENERAL INFORMATION:

( i i i ) NUMBER OF SEQUENCES: 11

( 2 ) INFORMATION FOR SEQ ID NO: 1:

( i ) SEQUENCE CHARACTERISTICS:
      ( A ) LENGTH: 4 amino acids
      ( B ) TYPE: amino acid
      ( D ) TOPOLOGY: linear ( i i ) MOLECULE TYPE: peptide ( i i i ) HYPOTHETICAL: NO ( i v ) ANTI-SENSE: NO ( x i ) SEQUENCE DESCRIPTION: SEQ ID NO: 1:

Pro Xaa Gly Pro
1

( 2 ) INFORMATION FOR SEQ ID NO: 2:

( i ) SEQUENCE CHARACTERISTICS:
( A ) LENGTH: 13 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO: 2:

GGGTACCTGG GCC 13

( 2 ) INFORMATION FOR SEQ ID NO: 3:

( i ) SEQUENCE CHARACTERISTICS:
( A ) LENGTH: 886 base pairs
( B ) TYPE: nucleic acid
( C ) STRANDEDNESS: single
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Chinese cucumber ( v i i ) IMMEDIATE SOURCE:
( B ) CLONE: alpha-trichosanthin ( i x ) FEATURE:
( A ) NAME/KEY: CDS (B) LOCATION: 8. .877
( B ) LOCATION: 8. .877

( x i ) SEQUENCE DESCRIPTION: SEQ ID NO: 3:

```
CTCGAGG ATG ATC AGA TTC TTA GTC CTC TCT TTG CTA ATT CTC ACC CTC      49
        Met Ile Arg Phe Leu Val Leu Ser Leu Leu Ile Leu Thr Leu
         1               5                  10

TTC CTA ACA ACT CCT GCT GTG GAG GGC GAT GTT AGC TTC CGT TTA TCA      97
Phe Leu Thr Thr Pro Ala Val Glu Gly Asp Val Ser Phe Arg Leu Ser
 15                  20                  25                  30

GGT GCA ACA AGC AGT TCC TAT GGA GTT TTC ATT TCA AAT CTG AGA AAA     145
Gly Ala Thr Ser Ser Ser Tyr Gly Val Phe Ile Ser Asn Leu Arg Lys
                 35                  40                  45

GCT CTT CCA AAT GAA AGG AAA CTG TAC GAT ATC CCT CTG TTA CGT TCC     193
Ala Leu Pro Asn Glu Arg Lys Leu Tyr Asp Ile Pro Leu Leu Arg Ser
             50                  55                  60

TCT CTT CCA GGT TCT CAA CGC TAC GCA TTG ATC CAT CTC ACA AAT TAC     241
Ser Leu Pro Gly Ser Gln Arg Tyr Ala Leu Ile His Leu Thr Asn Tyr
         65                  70                  75

GCC GAT GAA ACC ATT TCA GTG GCC ATA GAC GTA ACG AAC GTC TAT ATT     289
Ala Asp Glu Thr Ile Ser Val Ala Ile Asp Val Thr Asn Val Tyr Ile
     80                  85                  90

ATG GGA TAT CGC GCT GGC GAT ACA TCC TAT TTT TTC AAC GAG GCT TCT     337
Met Gly Tyr Arg Ala Gly Asp Thr Ser Tyr Phe Phe Asn Glu Ala Ser
 95                 100                 105                 110
```

| | | | | | | | | | | | | | | | | |
|---|---|---|---|---|---|---|---|---|---|---|---|---|---|---|---|---|
| GCA | ACA | GAA | GCT | GCA | AAA | TAT | GTA | TTC | AAA | GAC | GCT | ATG | CGA | AAA | GTT | 385 |
| Ala | Thr | Glu | Ala | Ala<br>115 | Lys | Tyr | Val | Phe | Lys<br>120 | Asp | Ala | Met | Arg | Lys<br>125 | Val | |
| ACG | CTT | CCA | TAT | TCT | GGC | AAT | TAC | GAA | AGG | CTT | CAA | ACT | GCT | GCG | GGC | 433 |
| Thr | Leu | Pro | Tyr<br>130 | Ser | Gly | Asn | Tyr | Glu<br>135 | Arg | Leu | Gln | Thr | Ala<br>140 | Ala | Gly | |
| AAA | ATA | AGG | GAA | AAT | ATT | CCG | CTT | GGA | CTC | CCA | GCT | TTG | GAC | AGT | GCC | 481 |
| Lys | Ile | Arg<br>145 | Glu | Asn | Ile | Pro | Leu<br>150 | Gly | Leu | Pro | Ala | Leu<br>155 | Asp | Ser | Ala | |
| ATT | ACC | ACT | TTG | TTT | TAC | TAC | AAC | GCC | AAT | TCT | GCT | GCG | TCG | GCA | CTT | 529 |
| Ile | Thr<br>160 | Thr | Leu | Phe | Tyr | Tyr<br>165 | Asn | Ala | Asn | Ser | Ala<br>170 | Ala | Ser | Ala | Leu | |
| ATG | GTA | CTC | ATT | CAG | TCG | ACG | TCT | GAG | GCT | GCG | AGG | TAT | AAA | TTT | ATT | 577 |
| Met<br>175 | Val | Leu | Ile | Gln | Ser<br>180 | Thr | Ser | Glu | Ala | Ala<br>185 | Arg | Tyr | Lys | Phe | Ile<br>190 | |
| GAG | CAA | CAA | ATT | GGG | AAG | CGC | GTT | GAC | AAA | ACC | TTC | CTA | CCA | AGT | TTA | 625 |
| Glu | Gln | Gln | Ile | Gly<br>195 | Lys | Arg | Val | Asp | Lys<br>200 | Thr | Phe | Leu | Pro | Ser<br>205 | Leu | |
| GCA | ATT | ATA | AGT | TTG | GAA | AAT | AGT | TGG | TCT | GCT | CTC | TCC | AAG | CAA | ATT | 673 |
| Ala | Ile | Ile | Ser<br>210 | Leu | Glu | Asn | Ser | Trp<br>215 | Ser | Ala | Leu | Ser | Lys<br>220 | Gln | Ile | |
| CAG | ATA | GCG | AGT | ACT | AAT | AAT | GGA | CAG | TTT | GAA | ACT | CCT | GTT | GTG | CTT | 721 |
| Gln | Ile | Ala<br>225 | Ser | Thr | Asn | Asn | Gly<br>230 | Gln | Phe | Glu | Thr | Pro<br>235 | Val | Val | Leu | |
| ATA | AAT | GCT | CAA | AAC | CAA | CGA | GTC | ATG | ATA | ACC | AAT | GTT | GAT | GCT | GGA | 769 |
| Ile | Asn<br>240 | Ala | Gln | Asn | Gln | Arg<br>245 | Val | Met | Ile | Thr | Asn<br>250 | Val | Asp | Ala | Gly | |
| GTT | GTA | ACC | TCC | AAC | ATC | GCG | TTG | CTG | CTG | AAT | CGA | AAC | AAT | ATG | GCA | 817 |
| Val<br>255 | Val | Thr | Ser | Asn | Ile<br>260 | Ala | Leu | Leu | Leu | Asn<br>265 | Arg | Asn | Asn | Met | Ala<br>270 | |
| GCC | ATG | GAT | GAC | GAT | GTT | CCT | ATG | ACA | CAG | AGC | TTT | GGA | TGT | GGA | AGT | 865 |
| Ala | Met | Asp | Asp | Asp<br>275 | Val | Pro | Met | Thr | Gln<br>280 | Ser | Phe | Gly | Cys | Gly<br>285 | Ser | |
| TAT | GCT | ATT | TAGTAACTCG | AG | | | | | | | | | | | | 886 |
| Tyr | Ala | Ile<br>290 | | | | | | | | | | | | | | |

( 2 ) INFORMATION FOR SEQ ID NO:4:

( i ) SEQUENCE CHARACTERISTICS:
        ( A ) LENGTH: 289 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

| | | | | | | | | | | | | | | |
|---|---|---|---|---|---|---|---|---|---|---|---|---|---|---|
| Met<br>1 | Ile | Arg | Phe | Leu<br>5 | Val | Leu | Ser | Leu | Leu<br>10 | Ile | Leu | Thr | Leu | Phe<br>15 | Leu |
| Thr | Thr | Pro | Ala<br>20 | Val | Glu | Gly | Asp | Val<br>25 | Ser | Phe | Arg | Leu | Ser<br>30 | Gly | Ala |
| Thr | Ser | Ser<br>35 | Ser | Tyr | Gly | Val | Phe<br>40 | Ile | Ser | Asn | Leu | Arg<br>45 | Lys | Ala | Leu |
| Pro | Asn<br>50 | Glu | Arg | Lys | Leu | Tyr<br>55 | Asp | Ile | Pro | Leu | Leu<br>60 | Arg | Ser | Ser | Leu |
| Pro<br>65 | Gly | Ser | Gln | Arg | Tyr<br>70 | Ala | Leu | Ile | His | Leu<br>75 | Thr | Asn | Tyr | Ala | Asp<br>80 |
| Glu | Thr | Ile | Ser | Val<br>85 | Ala | Ile | Asp | Val | Thr<br>90 | Asn | Val | Tyr | Ile | Met<br>95 | Gly |
| Tyr | Arg | Ala | Gly<br>100 | Asp | Thr | Ser | Tyr | Phe<br>105 | Phe | Asn | Glu | Ala | Ser<br>110 | Ala | Thr |
| Glu | Ala | Ala | Lys | Tyr | Val | Phe | Lys | Asp | Ala | Met | Arg | Lys | Val | Thr | Leu |

|  |  | 115 |  |  |  | 120 |  |  |  | 125 |  |  |  |  |
|---|---|---|---|---|---|---|---|---|---|---|---|---|---|---|
| Pro | Tyr | Ser | Gly | Asn | Tyr | Glu | Arg | Leu | Gln | Thr | Ala | Ala | Gly | Lys | Ile |
|  | 130 |  |  |  |  | 135 |  |  |  | 140 |  |  |  |  |

Arg Glu Asn Ile Pro Leu Gly Leu Pro Ala Leu Asp Ser Ala Ile Thr
145                150                155                160

Thr Leu Phe Tyr Tyr Asn Ala Asn Ser Ala Ala Ser Ala Leu Met Val
             165                170                175

Leu Ile Gln Ser Thr Ser Glu Ala Ala Arg Tyr Lys Phe Ile Glu Gln
         180                185                190

Gln Ile Gly Lys Arg Val Asp Lys Thr Phe Leu Pro Ser Leu Ala Ile
         195                200                205

Ile Ser Leu Glu Asn Ser Trp Ser Ala Leu Ser Lys Gln Ile Gln Ile
    210                215                220

Ala Ser Thr Asn Asn Gly Gln Phe Glu Thr Pro Val Val Leu Ile Asn
225                230                235                240

Ala Gln Asn Gln Arg Val Met Ile Thr Asn Val Asp Ala Gly Val Val
             245                250                255

Thr Ser Asn Ile Ala Leu Leu Leu Asn Arg Asn Asn Met Ala Ala Met
         260                265                270

Asp Asp Asp Val Pro Met Thr Gln Ser Phe Gly Cys Gly Ser Tyr Ala
         275                280                285

Ile ( 2 ) INFORMATION FOR SEQ ID NO: 5:

( i ) SEQUENCE CHARACTERISTICS:
        ( A ) LENGTH: 1450 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Oryza sativa ( v i i ) IMMEDIATE SOURCE:
        ( B ) CLONE: alpha-amylase ( i x ) FEATURE:
        ( A ) NAME/KEY: CDS (B) LOCATION: 12. .1316
        ( B ) LOCATION: 12. .1316

( x i ) SEQUENCE DESCRIPTION: SEQ ID NO: 5:

```
CCTCGAGGTG C ATG CAG GTG CTG AAC ACC ATG GTG AAC A CAC TTC TTG         48
             Met Gln Val Leu Asn Thr Met Val Asn Lys His Phe Leu
             1                5                   10

TCC CTT TCG GTC CTC ATC GTC CTC CTT GGC CTC TCC TCC AAC TTG ACA        96
Ser Leu Ser Val Leu Ile Val Leu Leu Gly Leu Ser Ser Asn Leu Thr
    15              20                  25

GCC GGG CAA GTC CTG TTT CAG GGA TTC AAC TGG GAG TCG TGG AAG GAG       144
Ala Gly Gln Val Leu Phe Gln Gly Phe Asn Trp Glu Ser Trp Lys Glu
30              35                  40                  45

AAT GGC GGG TGG TAC AAC TTC CTG ATG GGC AAG GTG GAC GAC ATC GCC       192
Asn Gly Gly Trp Tyr Asn Phe Leu Met Gly Lys Val Asp Asp Ile Ala
                50                  55                  60

GCA GCC GGC ATC ACC CAC GTC TGG CTC CCT CCG CCG TCT CAC TCT GTC       240
Ala Ala Gly Ile Thr His Val Trp Leu Pro Pro Pro Ser His Ser Val
            65                  70                  75
```

| | | | | | | | | | | | | | | | | |
|---|---|---|---|---|---|---|---|---|---|---|---|---|---|---|---|---|
| GGC | GAG | CAA | GGC | TAC | ATG | CCT | GGG | CGG | CTG | TAC | GAT | CTG | GAC | GCG | TCT | 288 |
| Gly | Glu | Gln | Gly | Tyr | Met | Pro | Gly | Arg | Leu | Tyr | Asp | Leu | Asp | Ala | Ser | |
| | | 80 | | | | 85 | | | | | 90 | | | | | |
| AAG | TAC | GGC | AAC | GAG | GCG | CAG | CTC | AAG | TCG | CTG | ATC | GAG | GCG | TTC | CAT | 336 |
| Lys | Tyr | Gly | Asn | Glu | Ala | Gln | Leu | Lys | Ser | Leu | Ile | Glu | Ala | Phe | His | |
| | 95 | | | | 100 | | | | | 105 | | | | | | |
| GGC | AAG | GGC | GTC | CAG | GTG | ATC | GCC | GAC | ATC | GTC | ATC | AAC | CAC | CGC | ACG | 384 |
| Gly | Lys | Gly | Val | Gln | Val | Ile | Ala | Asp | Ile | Val | Ile | Asn | His | Arg | Thr | |
| 110 | | | | 115 | | | | 120 | | | | | 125 | | | |
| GCG | GAG | CAC | AAG | GAC | GGC | CGC | GGC | ATC | TAC | TGC | CTC | TTC | GAG | GGC | GGG | 432 |
| Ala | Glu | His | Lys | Asp | Gly | Arg | Gly | Ile | Tyr | Cys | Leu | Phe | Glu | Gly | Gly | |
| | | | 130 | | | | 135 | | | | | 140 | | | | |
| ACG | CCC | GAC | TCC | CGC | CTC | GAC | TGG | GGC | CCG | CAC | ATG | ATC | TGC | CGC | GAC | 480 |
| Thr | Pro | Asp | Ser | Arg | Leu | Asp | Trp | Gly | Pro | His | Met | Ile | Cys | Arg | Asp | |
| | | | 145 | | | | 150 | | | | | 155 | | | | |
| GAC | CCC | TAC | GGC | CAT | GGC | ACC | GGC | AAC | CCG | GAC | ACC | GGC | GCC | GAC | TTC | 528 |
| Asp | Pro | Tyr | Gly | Asp | Gly | Thr | Gly | Asn | Pro | Asp | Thr | Gly | Ala | Asp | Phe | |
| | | 160 | | | | 165 | | | | | 170 | | | | | |
| GCC | GCC | GCG | CCG | GAC | ATC | GAC | CAC | CTC | AAC | AAG | CGC | GTC | CAG | CGG | GAG | 576 |
| Ala | Ala | Ala | Pro | Asp | Ile | Asp | His | Leu | Asn | Lys | Arg | Val | Gln | Arg | Glu | |
| 175 | | | | 180 | | | | | 185 | | | | | | | |
| CTC | ATT | GGC | TGG | CTC | GAC | TGG | CTC | AAG | ATG | GAC | ATC | GGC | TTC | GAC | GCG | 624 |
| Leu | Ile | Gly | Trp | Leu | Asp | Trp | Leu | Lys | Met | Asp | Ile | Gly | Phe | Asp | Ala | |
| 190 | | | | 195 | | | | | 200 | | | | | 205 | | |
| TGG | CGC | CTC | GAC | TTC | GCC | AAG | GGC | TAC | TCC | GCC | GAC | ATG | GCA | AAC | ATC | 672 |
| Trp | Arg | Leu | Asp | Phe | Ala | Lys | Gly | Tyr | Ser | Ala | Asp | Met | Ala | Lys | Ile | |
| | | | | 210 | | | | 215 | | | | | 220 | | | |
| TAC | ATC | GAC | GCC | ACC | GAG | CCG | AGC | TTC | GCC | GTG | CCC | GAG | ATA | TCG | ACG | 720 |
| Tyr | Ile | Asp | Ala | Thr | Glu | Pro | Ser | Phe | Ala | Val | Ala | Glu | Ile | Trp | Thr | |
| | | | 225 | | | | 230 | | | | | 235 | | | | |
| TCC | ATG | GCG | AAC | GGC | GGG | GAC | GGC | AAG | CCG | AAC | TAC | GAC | CAG | AAC | GCG | 768 |
| Ser | Met | Ala | Asn | Gly | Gly | Asp | Gly | Lys | Pro | Asn | Tyr | Asp | Gln | Asn | Ala | |
| | | 240 | | | | 245 | | | | | 250 | | | | | |
| CAC | CGG | CAG | GAG | CTG | GTC | AAC | TGG | GTC | GAT | CGT | GTC | GGC | GGC | GCC | AAC | 816 |
| His | Arg | Gln | Glu | Leu | Val | Asn | Trp | Val | Asp | Arg | Val | Gly | Gly | Ala | Asn | |
| 255 | | | | 260 | | | | | 265 | | | | | | | |
| ACC | AAC | GGC | ACG | GCG | TTC | GAC | TTC | ACC | ACC | AAG | GGC | ATC | CTC | AAC | GTC | 864 |
| Ser | Asn | Gly | Thr | Ala | Phe | Asp | Phe | Thr | Thr | Lys | Gly | Ile | Leu | Asn | Val | |
| 270 | | | | 275 | | | | 280 | | | | | 285 | | | |
| GCC | GTG | GAG | GGC | GAG | CTG | TGG | CGC | CTC | CGC | GGC | GAG | GAC | GGC | AAG | GCG | 912 |
| Ala | Val | Glu | Gly | Glu | Leu | Trp | Arg | Leu | Arg | Gly | Glu | Asp | Gly | Lys | Ala | |
| | | | 290 | | | | 295 | | | | | 300 | | | | |
| CCC | GGC | ATG | ATC | GGG | TGC | TGG | CCG | GCC | AAG | GCG | ACG | ACC | TTC | GTC | GAC | 960 |
| Pro | Gly | Met | Ile | Gly | Trp | Trp | Pro | Ala | Lys | Ala | Thr | Thr | Phe | Val | Asp | |
| | | | 305 | | | | 310 | | | | | 315 | | | | |
| AAC | CAC | GAC | ACC | GGC | TCG | ACG | CAG | CAC | CTG | TGG | CCG | TTC | CCC | TCC | GAC | 1008 |
| Asn | His | Asp | Thr | Gly | Ser | Thr | Gln | His | Leu | Trp | Pro | Phe | Pro | Ser | Asp | |
| | | 320 | | | | 325 | | | | | 330 | | | | | |
| AAG | GTC | ATG | CAG | GGC | TAC | GCA | TAC | ATC | CTC | ACC | CAC | CCC | GGC | AAC | CCA | 1056 |
| Lys | Val | Met | Gln | Gly | Tyr | Ala | Tyr | Ile | Leu | Thr | His | Pro | Gly | Asn | Pro | |
| | 335 | | | | 340 | | | | | 345 | | | | | | |
| TGC | ATC | TTG | TAC | GAC | CAT | TTC | TTC | GAT | TGG | GGT | CTC | AAG | GAG | GAG | ATC | 1104 |
| Cys | Ile | Phe | Tyr | Asp | His | Phe | Phe | Asp | Trp | Gly | Leu | Lys | Glu | Glu | Ile | |
| 350 | | | | | 355 | | | | 360 | | | | | 365 | | |
| GAG | CGC | CTG | GTG | TCA | ATC | AGA | AAC | CGG | CAG | GGG | ATC | CAC | CCG | GCG | AGC | 1152 |
| Glu | Arg | Leu | Val | Ser | Ile | Arg | Asn | Arg | Gln | Gly | Ile | His | Pro | Ala | Ser | |
| | | | | 370 | | | | 375 | | | | | 380 | | | |
| GAG | CTG | CGC | ATC | ATG | GAA | GCT | GAC | AGC | GAT | CTC | TAC | CTC | GCG | GAG | ATC | 1200 |
| Glu | Leu | Arg | Ile | Met | Glu | Ala | Asp | Ser | Asp | Leu | Tyr | Leu | Ala | Glu | Ile | |
| | | | | 385 | | | | 390 | | | | | | 395 | | |
| GAT | GGC | AAG | GTG | ATC | ACA | AAG | ATT | GGA | CCA | AGA | TAC | GAC | GTC | GAA | CAC | 1248 |
| Asp | Gly | Lys | Val | Ile | Thr | Lys | Ile | Gly | Pro | Arg | Tyr | Asp | Val | Glu | His | |

```
                    400                    405                         410
CTC  ATC  CCC  GAA  GGC  TTC  CAG  GTC  GTC  GCG  CAC  GGT  GAT  GGC  TAC  GCA         1296
Leu  Ile  Pro  Glu  Gly  Phe  Gln  Val  Val  Ala  His  Gly  Asp  Gly  Tyr  Ala
     415                 420                          425

ATC  TGG  GAG  AAA  ATC  TGAGCGCACG  ATGACGAGAC  TCTCAGTTTA  GCAGATTTAA              1351
Ile  Trp  Glu  Lys  LIe
430                 435

CCTGCGATTT  TTACCCTGAC  CGGTATACGT  ATATACGTGC  CGGCAACGAG  CTGTATCCGA                1411

TCCGAATTAC  GGATGCAATT  GTCCACGAAG  TCCTCGAGG                                         1450
```

( 2 ) INFORMATION FOR SEQ ID NO: 6:

( i ) SEQUENCE CHARACTERISTICS:
        ( A ) LENGTH: 434 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 6:

```
Met  Gln  Val  Leu  Asn  Thr  Met  Val  Asn  Lys  His  Phe  Leu  Ser  Leu  Ser
 1                    5                    10                       15

Val  Leu  Ile  Val  Leu  Leu  Gly  Leu  Ser  Ser  Asn  Leu  Thr  Ala  Gly  Gln
               20                    25                       30

Val  Leu  Phe  Gln  Gly  Phe  Asn  Trp  Glu  Ser  Trp  Lys  Glu  Asn  Gly  Gly
          35                    40                       45

Trp  Tyr  Asn  Phe  Leu  Met  Gly  Lys  Val  Asp  Asp  Ile  Ala  Ala  Ala  Gly
     50                    55                       60

Ile  Thr  His  Val  Trp  Leu  Pro  Pro  Ser  His  Ser  Val  Gly  Glu  Gln
65                    70                    75                           80

Gly  Tyr  Met  Pro  Gly  Arg  Leu  Tyr  Asp  Leu  Asp  Ala  Ser  Lys  Tyr  Gly
               85                    90                       95

Asn  Glu  Ala  Gln  Leu  Lys  Ser  Leu  Ile  Glu  Ala  Phe  His  Gly  Lys  Gly
               100                   105                      110

Val  Gln  Val  Ile  Ala  Asp  Ile  Val  Ile  Asn  His  Arg  Thr  Ala  Glu  His
          115                   120                      125

Lys  Asp  Gly  Arg  Gly  Ile  Tyr  Cys  Leu  Phe  Glu  Gly  Gly  Thr  Pro  Asp
     130                   135                      140

Ser  Arg  Leu  Asp  Trp  Gly  Pro  His  Met  Ile  Cys  Arg  Asp  Asp  Pro  Tyr
145                   150                   155                          160

Gly  Asp  Gly  Thr  Gly  Asn  Pro  Asp  Thr  Gly  Ala  Asp  Phe  Ala  Ala  Ala
               165                   170                      175

Pro  Asp  Ile  Asp  His  Leu  Asn  Lys  Arg  Val  Gln  Arg  Glu  Leu  Ile  Gly
               180                   185                      190

Trp  Leu  Asp  Trp  Leu  Lys  Met  Asp  Ile  Gly  Phe  Asp  Ala  Trp  Arg  Leu
          195                   200                      205

Asp  Phe  Ala  Lys  Gly  Tyr  Ser  Ala  Asp  Met  Ala  Lys  Ile  Tyr  Ile  Asp
     210                   215                      220

Ala  Thr  Glu  Pro  Ser  Phe  Ala  Val  Ala  Glu  Ile  Trp  Thr  Ser  Met  Ala
225                   230                   235                          240

Asn  Gly  Gly  Asp  Gly  Lys  Pro  Asn  Tyr  Asp  Gln  Asn  Ala  His  Arg  Gln
               245                   250                      255

Glu  Leu  Val  Asn  Trp  Val  Asp  Arg  Val  Gly  Gly  Ala  Asn  Ser  Asn  Gly
               260                   265                      270

Thr  Ala  Phe  Asp  Phe  Thr  Thr  Lys  Gly  Ile  Leu  Asn  Val  Ala  Val  Glu
          275                   280                      285

Gly  Glu  Leu  Trp  Arg  Leu  Arg  Gly  Glu  Asp  Gly  Lys  Ala  Pro  Gly  Met
     290                   295                      300
```

```
Ile  Gly  Trp  Trp  Pro  Ala  Lys  Ala  Thr  Thr  Phe  Val  Asp  Asn  His  Asp
305                 310                      315                      320

Thr  Gly  Ser  Thr  Gln  His  Leu  Trp  Pro  Phe  Pro  Ser  Asp  Lys  Val  Met
                325                      330                      335

Gln  Gly  Tyr  Ala  Tyr  Ile  Leu  Thr  His  Pro  Gly  Asn  Pro  Cys  Ile  Phe
                340                      345                      350

Tyr  Asp  His  Phe  Phe  Asp  Trp  Gly  Leu  Lys  Glu  Glu  Ile  Glu  Arg  Leu
          355                      360                      365

Val  Ser  Ile  Arg  Asn  Arg  Gln  Gly  Ile  His  Pro  Ala  Ser  Glu  Leu  Arg
          370                      375                      380

Ile  Met  Glu  Ala  Asp  Ser  Asp  Leu  Tyr  Leu  Ala  Glu  Ile  Asp  Gly  Lys
385                      390                      395                      400

Val  Ile  Thr  Lys  Ile  Gly  Pro  Arg  Tyr  Asp  Val  Glu  His  Leu  Ile  Pro
                405                      410                      415

Glu  Gly  Phe  Gln  Val  Val  Ala  His  Gly  Asp  Gly  Tyr  Ala  Ile  Trp  Glu
                420                      425                      430

Lys  Ile
```

( 2 ) INFORMATION FOR SEQ ID NO:7:

( i ) SEQUENCE CHARACTERISTICS:
        ( A ) LENGTH: 709 base pairs
        ( B ) TYPE: nucleic acid
        ( G ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:
        ( B ) CLONE: alpha-hemoglobin ( i x ) FEATURE:
        ( A ) NAME/KEY: transitpeptide (B)
            LOCATION: 26..241
        ( B ) LOCATION: 26..241

( i x ) FEATURE:
        ( A ) NAME/KEY: CDS
        ( B ) LOCATION: 245..670

( x i ) SEQUENCE DESCRIPTION: SEQ ID NO: 7:

```
CTCGAGGGCA  TCTGATCTTT  CAAGAATGGC  ACAAATTAAC  AACATGGCAC  AAGGGATACA        60

AACCCTTAAT  CCCAATTCCA  ATTTCCATAA  ACCCCAAGTT  CCTAAATCTT  CAAGTTTTCT       120

TGTTTTTGGA  TGTAAAAAAC  TGAAAAATTC  AGCAAATTCT  ATGTTGGTTT  TGAAAAAAGA       180

TTCAATTTTT  ATGCAAAAGT  TTTGTTCCTT  TAGGATTTCA  GCAGGTGGTA  GAGTTTCTTG       240

CATG  GTG  CTG  TCT  CCT  GCC  GAC  AAG  ACC  AAC  GTC  AAG  GCC  GCC  TGG  GGC      289
      Val  Leu  Ser  Pro  Ala  Asp  Lys  Thr  Asn  Val  Lys  Ala  Ala  Trp  Gly
        1              5                      10                         15

AAG  GTT  GGC  GCG  CAC  GCT  GGC  GAG  TAT  GGT  GCG  GAG  GCC  CTG  GAG  AGG       337
Lys  Val  Gly  Ala  His  Ala  Gly  Glu  Tyr  Gly  Ala  Glu  Ala  Leu  Glu  Arg
                    20                      25                      30

ATG  TTC  CTG  TCC  TTC  CCC  ACC  ACC  AAG  ACC  TAC  TTC  CCG  CAC  TTC  GAC       385
Met  Phe  Leu  Ser  Phe  Pro  Thr  Thr  Lys  Thr  Tyr  Phe  Pro  His  Phe  Asp
                    35                      40                      45

CTG  AGC  CAC  GGC  TCT  GCC  CAG  GTT  AAG  GGC  CAC  GGC  AAG  AAG  GTG  GCC       433
Leu  Ser  His  Gly  Ser  Ala  Gln  Val  Lys  Gly  His  Gly  Lys  Lys  Val  Ala
```

```
            50                      55                      60
GAC GCG CTG ACC AAC GCC GTG GCG CAC GTG GAC GAC ATG CCC AAC GCG    481
Asp Ala Leu Thr Asn Ala Val Ala His Val Asp Asp Met Pro Asn Ala
        65                      70                  75

CTG TCC GCC CTG AGC GAC CTG CAC GCG CAC AAG CTT CGG GTG GAC CCG    529
Leu Ser Ala Leu Ser Asp Leu His Ala His Lys Leu Arg Val Asp Pro
80                      85                      90                  95

GTC AAC TTC AAG CTC CTA AGC CAC TGC CTG CTG GTG ACC CTG GCC GCC    577
Val Asn Phe Lys Leu Leu Ser His Cys Leu Leu Val Thr Leu Ala Ala
                    100                     105                     110

CAC CTC CCC GCC GAG TTC ACC CCT GCG GTG CAC GCC TCC CTG GAC AAG    625
His Leu Pro Ala Glu Phe Thr Pro Ala Val His Ala Ser Leu Asp Lys
                115                     120                     125

TTC CTG GCT TCT GTG AGC ACC GTG CTG ACC TCC AAA TAC CGT TAAGCTGGAG 677
Phe Leu Ala Ser Val Ser Thr Val Leu Thr Ser Lys Tyr Arg
            130                     135                 140

CCTCGGTAGC CGTTCCTCCT GCCCGGTCGA CC                                709
```

( 2 ) INFORMATION FOR SEQ ID NO:8:

( i ) SEQUENCE CHARACTERISTICS:
        ( A ) LENGTH: 141 amino acids
        ( B ) TYPE: amino acid
        ( D ) TOPOLOGY: linear ( i i ) MOLECULE TYPE: protein ( i x ) SEQUENCE DESCRIPTION: SEQ ID NO:8:

```
Val Leu Ser Pro Ala Asp Lys Thr Asn Val Lys Ala Ala Trp Gly Lys
 1               5                  10                  15

Val Gly Ala His Ala Gly Glu Tyr Gly Ala Glu Ala Leu Glu Arg Met
                20                      25                      30

Phe Leu Ser Phe Pro Thr Thr Lys Thr Tyr Phe Pro His Phe Asp Leu
            35                      40                      45

Ser His Gly Ser Ala Gln Val Lys Gly His Gly Lys Lys Val Ala Asp
        50                      55                      60

Ala Leu Thr Asn Ala Val Ala His Val Asp Asp Met Pro Asn Ala Leu
65                      70                      75                  80

Ser Ala Leu Ser Asp Leu His Ala His Lys Leu Arg Val Asp Pro Val
                85                      90                      95

Asn Phe Lys Leu Leu Ser His Cys Leu Leu Val Thr Leu Ala Ala His
            100                     105                     110

Leu Pro Ala Glu Phe Thr Pro Ala Val His Ala Ser Leu Asp Lys Phe
        115                     120                     125

Leu Ala Ser Val Ser Thr Val Leu Thr Ser Lys Tyr Arg
        130                     135                     140
```

( 2 ) INFORMATION FOR SEQ ID NO:9:

( i ) SEQUENCE CHARACTERISTICS:
        ( A ) LENGTH: 743 base pairs
        ( B ) TYPE: nucleic acid
        ( C ) STRANDEDNESS: single
        ( D ) TOPOLOGY: linear ( i i ) MOLECULE TYPE: cDNA to mRNA ( i i i ) HYPOTHETICAL: NO ( i v ) ANTI-SENSE: NO ( v i ) ORIGINAL SOURCE:
        ( A ) ORGANISM: Homo sapiens ( v i i ) IMMEDIATE SOURCE:

(B) CLONE: beta-hemoglobin (ix) FEATURE:
 (A) NAME/KEY: transitpeptide (B)
  LOCATION: 26..241
 (B) LOCATION: 26..241

(ix) FEATURE:
 (A) NAME/KEY: CDS
 (B) LOCATION: 245..685

(xi) SEQUENCE DESCRIPTION: SEQ ID NO: 9:

```
CTCGAGGGGA TCTGATCTTT CAAGAATGGC ACAAATTAAC AACATGGCAC AAGGGATACA    60

AACCCTTAAT CCCAATTCCA ATTTCCATAA ACCCCAAGTT CCTAAATCTT CAAGTTTTCT   120

TGTTTTTGGA TCTAAAAAAC TGAAAAATTC AGCAAATTCT ATGTTGGTTT TGAAAAAAGA   180

TTCAATTTTT ATGCAAAAGT TTTGTTCCTT TAGGATTTCA GCAGGTGGTA GAGTTTCTTG   240
```

```
GATG GTG CAC CTG ACT CCT GAG GAG AAG TCT GCC GTT ACT GCC CTG TGG    289
     Val His Leu Thr Pro Glu Glu Lys Ser Ala Val Thr Ala Leu Trp
     1             5                  10                     15

GGC AAG GTG AAC GTG GAT GAA GTT GGT GGT GAG GCC CTG GGC AGG CTG     337
Gly Lys Val Asn Val Asp Glu Val Gly Gly Glu Ala Leu Gly Arg Leu
                20                  25                  30

CTG GTG GTC TAC CCT TGG ACC CAG AGG TTC TTT GAG TCC TTT GGG GAT     385
Leu Val Val Tyr Pro Trp Thr Gln Arg Phe Phe Glu Ser Phe Gly Asp
             35                  40                  45

CTG TCC ACT CCT GAT GCT GTT ATG GGC AAC CCT AAG GTG AAG GCT CAT     433
Leu Ser Thr Pro Asp Ala Val Met Gly Asn Pro Lys Val Lys Ala His
         50                  55                  60

GGC AAG AAA GTG CTG GGT GCC TTT AGT GAT GGC CTG GCT CAC CTG GAC     481
Gly Lys Lys Val Leu Gly Ala Phe Ser Asp Gly Leu Ala His Leu Asp
     65                  70                  75

AAC CTC AAG GGC ACC TTT GCC ACC CTG AGT GAG CTG CAC TGT GAC AAG     529
Asn Leu Lys Gly Thr Phe Ala Thr Leu Ser Glu Leu His Cys Asp Lys
 80                  85                  90                  95

CTG CAC GTG GAT CCT GAG AGC TTC AGG CTC CTA GGC AAC GTG CTG GTC     577
Leu His Val Asp Pro Glu Ser Phe Arg Leu Leu Gly Asn Val Leu Val
                100                 105                 110

TGT GTG CTG GCG CAT CAC TTT GGC AAA GAA TTC ACC CCA CCA GTG CAG     625
Cys Val Leu Ala His His Phe Gly Lys Glu Phe Thr Pro Pro Val Gln
             115                 120                 125

GCT GCC TAT CAG AAA GTG GTG GCT GGT GTG GCT AAT GCC CTG GCC CAC     673
Ala Ala Tyr Gln Lys Val Val Ala Gly Val Ala Asn Ala Leu Ala His
         130                 135                 140

AAG TAT CAC TAAGCTCGCT TTCTTGCTGT CCAATTTCTA TTAAAGGTTC             722
Lys Tyr His
         145

CTTTGTGGGG TCGAGGTCGA C                                             743
```

(2) INFORMATION FOR SEQ ID NO: 10:

(i) SEQUENCE CHARACTERISTICS:
  (A) LENGTH: 146 amino acids
  (B) TYPE: amino acid
  (D) TOPOLOGY: linear (ii) MOLECULE TYPE: protein (xi) SEQUENCE DESCRIPTION: SEQ ID NO: 10:

```
Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
                20                  25                  30
```

-continued

```
Val  Val  Tyr  Pro  Trp  Thr  Gln  Arg  Phe  Phe  Glu  Ser  Phe  Gly  Asp  Leu
          35                       40                      45

Ser  Thr  Pro  Asp  Ala  Val  Met  Gly  Asn  Pro  Lys  Val  Lys  Ala  His  Gly
     50                       55                      60

Lys  Lys  Val  Leu  Gly  Ala  Phe  Ser  Asp  Gly  Leu  Ala  His  Leu  Asp  Asn
65                       70                      75                           80

Leu  Lys  Gly  Thr  Phe  Ala  Thr  Leu  Ser  Glu  Leu  His  Cys  Asp  Lys  Leu
               85                       90                           95

His  Val  Asp  Pro  Glu  Ser  Phe  Arg  Leu  Leu  Gly  Asn  Val  Leu  Val  Cys
               100                      105                     110

Val  Leu  Ala  His  His  Phe  Gly  Lys  Glu  Phe  Thr  Pro  Pro  Val  Gln  Ala
          115                      120                      125

Ala  Tyr  Gln  Lys  Val  Val  Ala  Gly  Val  Ala  Asn  Ala  Leu  Ala  His  Lys
     130                      135                     140

Tyr  His
145
```

( 2 ) INFORMATION FOR SEQ ID NO:11:

( i ) SEQUENCE CHARACTERISTICS:
        ( A ) LENGTH: 17 amino acids
        ( B ) TYPE: amino acid
        ( D ) TOPOLOGY: linear ( i i ) MOLECULE TYPE: peptide ( v ) FRAGMENT TYPE: N-terminal ( v i ) ORIGINAL SOURCE:
        ( A ) ORGANISM: alkalophilic Bacillus sp.
        ( B ) STRAIN: 38-2

( v i i ) IMMEDIATE SOURCE:
        ( B ) CLONE: beta-cyclodextrin ( x i ) SEQUENCE DESCRIPTION: SEQ ID NO: 11:

```
Ala  Pro  Asp  Thr  Ser  Val  Ser  Asn  Lys  Gln  Asn  Phe  Ser  Thr  Asp  Val
1                   5                        10                      15

Ile
```